(12) United States Patent
Taugerbeck et al.

(10) Patent No.: US 7,326,447 B2
(45) Date of Patent: Feb. 5, 2008

(54) BENZOCHROMENE DERIVATIVES

(75) Inventors: Andreas Taugerbeck, Darmstadt (DE);
Melanie Klasen-Memmer, Heuchelheim (DE)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 205 days.

(21) Appl. No.: 10/546,801

(22) PCT Filed: Jan. 28, 2004

(86) PCT No.: PCT/EP2004/000731

§ 371 (c)(1),
(2), (4) Date: Aug. 24, 2005

(87) PCT Pub. No.: WO2004/076438

PCT Pub. Date: Sep. 10, 2004

(65) Prior Publication Data

US 2006/0177603 A1 Aug. 10, 2006

(30) Foreign Application Priority Data

Feb. 25, 2003 (DE) ................. 103 08 266

(51) Int. Cl.
*C09K 19/34* (2006.01)
*C09K 19/32* (2006.01)
*C09K 19/30* (2006.01)
*C09K 19/52* (2006.01)
*C07D 311/78* (2006.01)
*C07D 311/80* (2006.01)
*C07D 311/82* (2006.01)

(52) U.S. Cl. ............ 428/1.1; 252/299.01; 252/299.61; 252/299.62; 252/299.63; 549/280; 549/388; 549/390; 549/393

(58) Field of Classification Search ........... 252/299.61, 252/299.62, 299.01, 299.63; 428/1.1; 549/280, 549/388, 390, 393
See application file for complete search history.

(56) References Cited

U.S. PATENT DOCUMENTS 5,648,021 A 7/1997 Wingen et al.

FOREIGN PATENT DOCUMENTS

| FR | 95 364 | 8/1970 |
| JP | 10 236992 | 9/1998 |
| JP | 2001 026587 | 1/2001 |

OTHER PUBLICATIONS

CAPLUS 2006:882355.*
Fedorov A Y et al: "Aryllead Triacetates in the Synthesis of Oxaphenanthrene Derivatives" Tetrahedron Letters, Elsevier Science Publishers, Amsterdam, NL, vol. 42, No. 34, Aug. 20, 2001.
Harrowven D C et al: "A New Cascade Radical Reaction for the Synthesis of Biaryls and Triaryls From Benzyl Iodoaryl Ethers" Tetrahedron Letters, Elsevier Science Publsihers, Amsterdam, NL, vol. 42, No. 5, Jan. 29, 2001, pp. 961-964.
Neumeister, Joachim et al: "Abnormal Products in the Exhaustive Ozone Oxidation of Phenanthrene in Hydrochloric Acid/Methanol" Chemische Berichte.
Shishido, Kozo et al: The Competition Between Electrocyclic Reaction and "1,5!sigmatropic Reaction in the Thermolysis of 1,1-Disubstituted Benzocyclobutenes" Chemistry Letters.
Patent Abstracts of Japan vol. 2000, No. 16, May 8, 2001.
Patent Abstracts of Japan vol. 1998, No. 14, Dec. 31, 1998.

* cited by examiner

*Primary Examiner*—Shean C Wu
(74) *Attorney, Agent, or Firm*—Millen, White, Zelano & Branigan, P.C.

(57) ABSTRACT

The present invention relates to benzochromene derivatives of the formula I $$R^1 \!-\!\! \left[ A^1 \right] \!\!-\!\! Z^1 \!\!-\!\!\!\Big]_n \!\!\begin{array}{c} L^1 \quad Y\!-\!O \quad L^2 \\ \phantom{X} \\ \end{array}\!\!\Big[\!\!-\!\! Z^2 \!-\!\! \left[ A^2 \right] \!\!-\!\!\Big]_m \!\!\!-\! R^2 \quad \text{I}$$

in which the various parameters are as defined in the text, and to liquid-crystal media which comprise these compounds, and to the use of the media in electro-optical displays, in particular in VAN LCDs.

20 Claims, No Drawings

BENZOCHROMENE DERIVATIVES

The present invention relates to benzochromene derivatives, preferably mesogenic benzochromene derivatives, in particular liquid-crystalline benzochromene derivatives, and to liquid-crystalline media comprising these benzochromene derivatives. The present invention furthermore relates to liquid-crystal displays, in particular liquid-crystal displays addressed by means of an active matrix (AMDs or AM LCDs ("active matrix addressed liquid crystal displays")) and very particularly so-called VAN ("vertically aligned nematic") liquid-crystal displays, an embodiment of ECB ("electrically controlled birefringence") liquid-crystal displays, in which nematic liquid crystals of negative dielectric anisotropy ($\Delta\epsilon$) are used.

In liquid-crystal displays of this type, the liquid crystals are used as dielectrics whose optical properties change reversibly on application of an electric voltage. Electro-optical displays which use liquid crystals as media are known to the person skilled in the art. These liquid-crystal displays use various electro-optical effects. The most common of these are the TN ("twisted nematic") effect, with a homogeneous, virtually planar initial alignment of the liquid-crystal director and a nematic structure twisted by about 90°, the STN ("supertwisted nematic") effect and the SBE ("super-twisted birefringence effect") effect, with a nematic structure twisted by 180° or more. In these and similar electro-optical effects, liquid-crystalline media of positive dielectric anisotropy ($\Delta\epsilon$) are used.

Besides the said electro-optical effects, which require liquid-crystal media of positive dielectric anisotropy, there are other electro-optical effects which use liquid-crystal media of negative dielectric anisotropy, such as, for example, the ECB effect and its sub-forms DAP ("deformation of aligned phases"), VAN and CSH ("colour super homeotropics").

An electro-optical effect having excellent, low, viewing-angle dependence of the contrast uses axially symmetric micropixels (ASMs). In this effect, the liquid crystal in each pixel is surrounded cylindrically by a polymer material. This mode is particularly suitable for combination with addressing through plasma channels. Thus, in particular, large-area PA ("plasma addressed") LCDs having good viewing-angle dependence of the contrast can be achieved.

The IPS ("in plane switching") effect, which has been increasingly employed recently, can use both dielectrically positive and dielectrically negative liquid-crystal media, similar to guest/host displays, which are able to employ dyes either in dielectrically positive or in dielectrically negative media, depending on the display mode used.

Since the operating voltage in liquid-crystal displays in general, i.e. including in displays based on these effects, should be as low as possible, use is made of liquid-crystal media having a large absolute value of the dielectric anisotropy, which generally predominantly and usually even very substantially consist of liquid-crystal compounds having a dielectric anisotropy having the corresponding sign, i.e. consist of compounds of positive dielectric anisotropy in the case of dielectrically positive media and of compounds of negative dielectric anisotropy in the case of dielectrically negative media. In the respective types of media (dielectrically positive or dielectrically negative), at most significant amounts of dielectrically neutral liquid-crystal compounds are typically employed. Liquid-crystal compounds having the sign of the dielectric anisotropy opposite to the dielectric anisotropy of the medium are generally employed in extremely small amounts, or not at all.

An exception here is formed by liquid-crystalline media for MIM ("metal-insulator-metal") displays (Simmons, J. G., Phys. Rev. 155 No. 3, pp. 657-660 and Niwa, J. G. et al., SID 84 Digest, pp. 304-307, June 1984), in which the liquid-crystal media are addressed by means of an active matrix of thin-film transistors. In this type of addressing, which utilises the non-linear characteristic line of diode switching, it is not possible, in contrast to TFT displays, to charge a storage capacitor together with the electrodes of the liquid-crystal display elements (pixels). A reduction in the effect of voltage drop during the addressing cycle therefore requires the highest possible base value of the dielectric constant. In dielectrically positive media, as employed, for example, in MIM-TN displays, the dielectric constant perpendicular to the molecular axis ($\epsilon_{195}$) must therefore be as large as possible, since it determines the base capacitance of the pixel. To this end, as described, for example, in WO 93/01253, EP 0 663 502 and DE 195 21 483, compounds of negative dielectric anisotropy are simultaneously employed in addition to dielectrically positive compounds in the dielectrically positive liquid-crystal media.

A further exception is formed by STN displays in which, for example in accordance with DE 41 00 287, dielectrically positive liquid-crystal media comprising dielectrically negative liquid-crystal compounds are employed in order to increase the steepness of the electro-optical characteristic line.

The pixels of the liquid-crystal displays can be addressed directly, time-sequentially, i.e. in time multiplex mode, or by means of a matrix of active elements having nonlinear electric characteristic lines.

The most common AMDs to date use discrete active electronic switching elements, such as, for example, three-pole switching elements, such as MOS ("metal oxide silicon") transistors or thin-film transistors (TFTs) or varistors or 2-pole switching elements, such as, for example, MIM ("metal insulator metal") diodes, ring diodes or back-to-back diodes. In TFTs, various semiconductor materials, predominantly silicon, but also cadmium selenide, are used. In particular, amorphous silicon or polycrystalline silicon is used.

In accordance with the present application, preference is given to liquid-crystal displays having an electric field perpendicular to the liquid-crystal layer and liquid-crystal media of negative dielectric anisotropy ($\Delta\epsilon<0$). In these displays, the edge alignment of the liquid crystals is homeotropic. In the fully switched-through state, i.e. on application of a correspondingly high electric voltage, the liquid-crystal director is aligned parallel to the layer plane.

Cyclic lactones of the formula

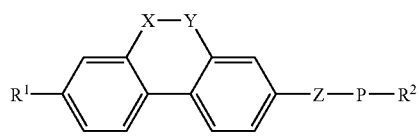

in which

—X—Y— is —CO—O— or —O—CO— are disclosed in JP 2001-026 587 (A). These compounds are characterised by broad smectic phases and are proposed for use in ferroelectric liquid-crystal mixtures in JP 2001-026 587 (A).

U.S. Pat. No. 5,648,021 discloses fluorinated phenanthrenes of the formula

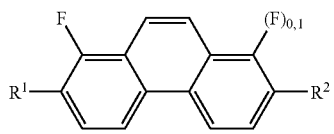

and fluorinated 9,10-dihydrophenanthrenes of the formula

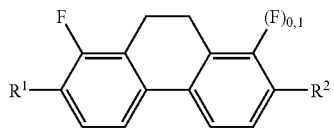

These also have broad smectic phases and are likewise proposed for use in ferroelectric liquid-crystal mixtures.

DE 100 64 995 presents fluorinated phenanthrenes of the formula

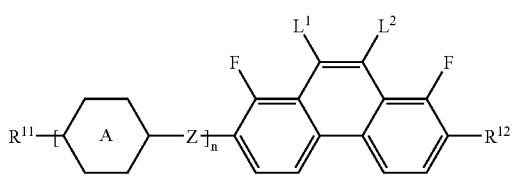

in which $L^1$ and $L^2$ are each, independently of one another, H or F, and proposes them for use in nematic liquid-crystal mixtures, in particular for ECB displays. The example compounds in which $L^1$ and $L^2$ are both H and which contain one alkyl end group and one alkoxy end group have an only slightly negative Δε, whereas the example compounds in which $L^1$ and $L^2$ are both F and which contain one alkoxy end group, although having a more negative Δε, generally have greater rotational viscosity, significantly lower solubility and in addition in most cases inadequate UV stability.

It is thus evident that there is both a demand for further mesogenic compounds and also, in particular, a demand for liquid-crystal media of negative dielectric anisotropy having a large absolute value of the dielectric anisotropy, a value of the optical anisotropy (Δn) corresponding to the particular application, a broad nematic phase, good stability to UV, heat and electric voltage and low rotational viscosity.

This is achieved through the use of the mesogenic compounds of the formula I according to the invention

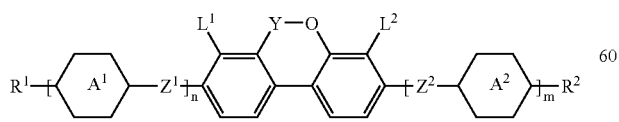

in which

Y is —CO—, —CS—, —CH$_2$—, —CF$_2$— or —CHF—, preferably —CF$_2$—, $L^1$ and $L^2$ are each, independently of one another, H, F, Cl or —CN, preferably H or F, preferably at least one of $L^1$ and $L^2$ is F, particularly preferably $L^1$ and $L^2$ are both F,

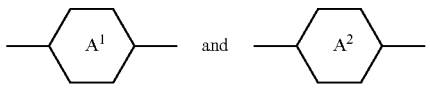

are each, independently of one another, and, if present more than once, also independently of one another, (a) a trans-1,4-cyclohexylene radical, in which, in addition, one or two non-adjacent CH$_2$ groups may be replaced by —O— and/or —S—, (b) a 1,4-cyclohexenylene radical, (c) a 1,4-phenylene radical, in which, in addition, one or two non-adjacent CH groups may be replaced by N, or (d) a radical selected from the group consisting of 1,4-bicyclo-[2.2.2]octylene, 1,3-bicyclo[1.1.1]pentylene, spiro[3.3]-heptane-2,4-diyl, piperidine-1,4-diyl, naphthalene-2,6-diyl, decahydronaphthalene-2,6-diyl and 1,2,3,4-tetrahydro-naphthalene-2,6-diyl, preferably

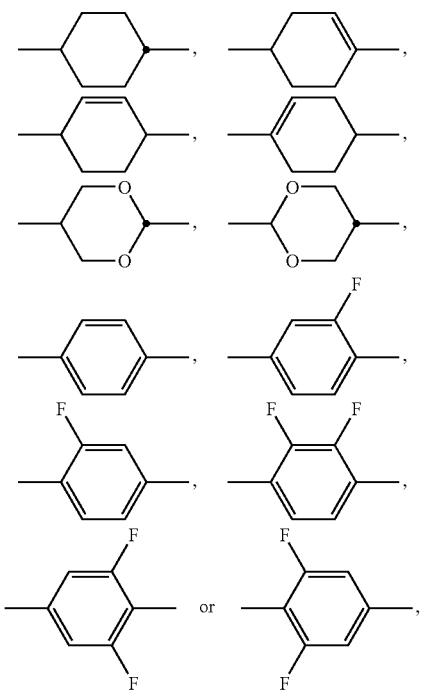

$R^1$ and $R^2$ are each, independently of one another, H, halogen, —CN, —SCN, —SF$_5$, —CF$_3$, —CHF$_2$, —CH$_2$F, —OCF$_3$, —OCHF$_2$, or an alkyl group having from 1 to 15 carbon atoms which is monosubstituted by CN or CF$_3$ or at least monosubstituted by halogen and in which, in addition, one or more CH$_2$ groups may each, independently of one another, be replaced by —O—, —S—, —CH=CH—, —CF=CF—, —CF=CH—, —CH=CF—,

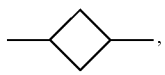

—CO—, —CO—O—, —O—CO— or —O—CO—O— in such a way that neither O nor S atoms are linked directly to one another,
preferably one of
$R^1$ and $R^2$ is alkyl or alkoxy having from 1 to 12 carbon atoms, alkoxyalkyl, alkenyl or alkenyloxy having from 2 to 12 carbon atoms and the other, independently of the first, is likewise alkyl or alkoxy having from 1 to 12 carbon atoms, alkoxyalkyl, alkenyl or alkenyloxy having from 2 to 12 carbon atoms or alternatively F, Cl, Br, —CN, —SCN, —$SF_5$, —$CF_3$, —$CHF_2$, —$CH_2F$, —$OCF_3$ or —$OCHF_2$,
$Z^1$ and $Z^2$ are each, independently of one another, a single bond, —$CH_2$—$CH_2$—, —$CF_2$—$CF_2$—, —$CF_2$—$CH_2$—, —$CH_2$—$CF_2$—, —CH=CH—, —CF=CF—, —CF=CH—, —CH=CF—, —C≡C—, —COO—, —OCO—, —$CH_2$O—, —O$CH_2$—, —$CF_2$O—, —O$CF_2$—, or a combination of two of these groups, where no two O atoms are bonded to one another, preferably —$(CH_2)_4$—, —$CH_2$—$CH_2$—, —$CF_2$—$CF_2$—, —CH=CH—, —CF=CF—, —C≡C—, —$CH_2$O—, —$CF_2$O— or a single bond,
particularly preferably —$CH_2$O—, —$CH_2$—$CH_2$—, —$CF_2$—$CF_2$—, —CF=CF—, —$CF_2$O— or a single bond, and
n and m are each 0, 1 or 2, where
n+m is 0, 1, 2 or 3, preferably 0, 1 or 2, particularly preferably 0 or 1,
with the proviso that, if Y is —CO—, at least one of $L^1$ and $L^2$ is not H.

Particular preference is given to liquid-crystal compounds of the formula I of the sub-formulae 1-1 to 1-3

I-1
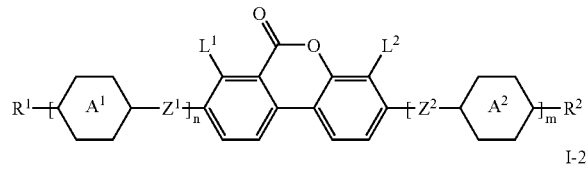

I-2
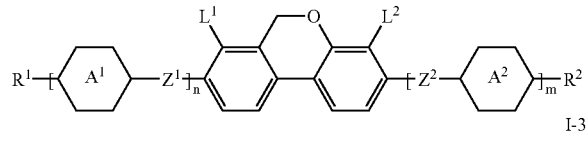

I-3
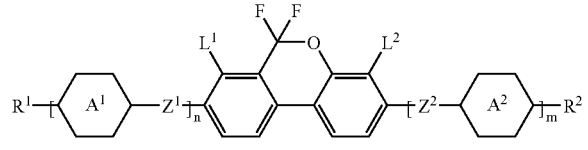

in which the parameters are as defined above under the formula I, and
$L^1$ and $L^2$ are preferably both F.

Preference is given to compounds of the formula 1, preferably selected from the group consisting of the compounds of the formulae I-1 to I-3, in which the sum n+m is 0 or 1, preferably 0.
A preferred embodiment is represented by the compounds of the formula I in which the sum n+m is 1 and preferably m or n is,

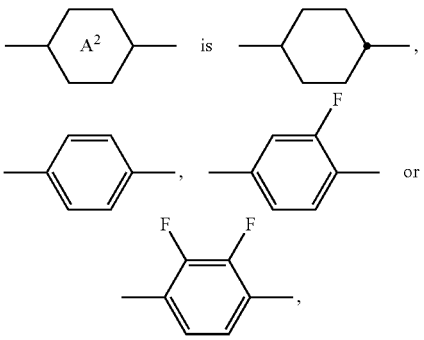

$Z^2$ is preferably —$(CH_2)_4$—, —$CH_2$—$CH_2$—, —$CF_2$—$CF_2$—, —CH=CH—, —CF=CF—, —C≡C—, —O—$CH_2$—, —O—$CF_2$— or a single bond, particularly preferably —O—$CH_2$—, —$CH_2$—$CH_2$—, —$CF_2$—$CF_2$—, —CF=CF—, —O—$CF_2$— or a single bond,
and $L^1$, $L^2$, $R^1$ and $R^2$ are as defined above under the formula I, and $L^1$ and $L^2$ are preferably both F.

Particular preference is given to compounds of the formula I, preferably selected from the group consisting of the compounds of the formulae I-1 to I-3, in which
n and m are both 0, and
$L^1$, $L^2$, $R^1$ and $R^2$ are as defined above under the corresponding formula, and $L^1$ and $L^2$ are preferably both F.

Compounds of the formula I containing branched wing groups $R^1$ and/or $R^2$ may occasionally be of importance owing to better solubility in the usual liquid-crystalline base materials, but in particular as chiral dopants if they are optically active. Smectic compounds of this type are suitable as components of ferroelectric materials. Compounds of the formula I having $S_A$ phases are suitable, for example, for thermally addressed displays.

If $R^1$ and/or $R^2$ is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetra-decyl, pentadecyl, methoxy, octyloxy, nonyloxy, decyloxy, undecyloxy, dodecyloxy, tridecyloxy or tetradecyloxy.

Oxaalkyl or alkoxyalkyl is preferably straight-chain 2-oxapropyl (=methoxy-methyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ and/or $R^2$ is an alkyl radical in which one $CH_2$ group has been replaced by —CH=CH—, this may be straight-chain or branched. It is preferably straight-chain and has from 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or-5-enyl, hept-1-, -2-, -3-, -4-, -5-or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ and/or $R^2$ is an alkyl radical in which one $CH_2$ group has been replaced by —O— and one has been replaced by —CO—, these are preferably adjacent. These thus contain an acyloxy group —CO—O— or an oxycarbonyl group —O—CO—. These are preferably straight-chain and have from 2 to 6 carbon atoms. Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxyca rbonylmethyl, 2-(methoxyca rbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ and/or $R^2$ is an alkyl radical in which one $CH_2$ group has been replaced by unsubstituted or substituted —CH=CH— and an adjacent $CH_2$ group has been replaced by CO or CO—O or O—CO, this may be straight-chain or branched. It is preferably straight-chain and has from 4 to 13 carbon atoms. Accordingly, it is in particular acryloyloxymethyl, 2-acryl-oyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If $R^1$ and/or $R^2$ is an alkyl or alkenyl radical which is monosubstituted by CN or $CF_3$, this radical is preferably straight-chain. The substitution by CN or $CF_3$ is in any desired position.

If $R^1$ and/or $R^2$ is an alkyl or alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the o-position.

Branched groups generally contain not more than one chain branch. Preferred branched radicals $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexyloxy, 1-methylhexyloxy and 1-methyl-heptyloxy.

If $R^1$ and/or $R^2$ is an alkyl radical in which two or more $CH_2$ groups have been replaced by —O— and/or —CO—O—, this may be straight-chain or branched. It is preferably branched and has from 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-bis-carboxyhexyl, 7,7-biscarboxyheptyl, 8,8-b isca rboxyoctyl, 9,9-biscarboxy-nonyl, 10,10-biscarboxydecyl, bis(methoxycarbonyl)methyl, 2,2-bis-(methoxycarbonyl)ethyl, 3,3-bis(methoxycarbonyl)propyl, 4,4-bis(methoxy-carbonyl)butyl, 5,5-bis(methoxycarbonyl)pentyl, 6,6-bis(methoxycarbonyl)-hexyl, 7,7-bis(methoxycarbonyl) heptyl, 8,8-bis(methoxycarbonyl)octyl, bis(ethoxycarbonyl) methyl, 2,2-bis(ethoxycarbonyl)ethyl, 3,3-bis(ethoxycarbonyl)propyl, 4,4-bis(ethoxycarbonyl)butyl or 5,5-bis (ethoxycarbonyl)-hexyl.

Particular preference is given to compounds of the formula I in which n=0 or 1 and m=0 and $R^1$ is methyl, ethyl, propyl, butyl, pentyl, vinyl, 1E-propenyl, 1E-butenyl or 1E-pentenyl, and to media comprising these compounds. Of these compounds, the alkyl-substituted compounds are particularly preferably employed.

The compounds of the formula I are prepared in accordance with the following schemes (Schemes I to XX).

The cyclic lactones can be prepared in accordance with Scheme I by intramolecular cyclisation of aryl phenyl esters which have been halogenated in a suitable manner by coupling reactions of the Ullmann type (Houben Weyl, Methoden der Organischen Chemie [Methods of Organic Chemistry], New York, 1993). They can alternatively be obtained by palladium-catalysed intramolecular cross-coupling reactions as shown in Scheme II and Scheme III.

Alternatively, the cross-coupling can also be carried out in a first step with the correspondingly protected phenols and carboxylic acid esters, as shown in Scheme IIIa using the example of a Negishi reaction (Negishi, E. et al., J. Org. Chem. (1977) 42, pp. 1821-1823).

Scheme I

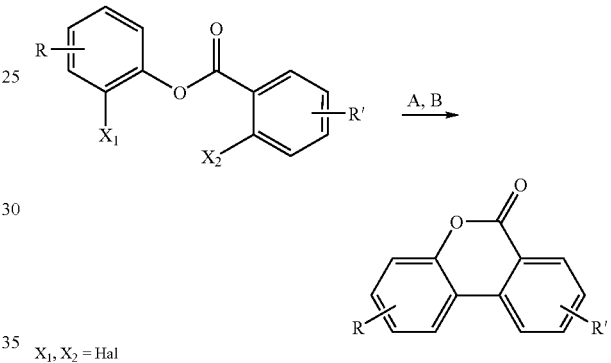

$X_1, X_2$ = Hal in which, as in Schemes Ia to Id, II, III, IIIa, IV to XX, unless explicitly stated otherwise, R and R' are each, independently of one another, as defined above for

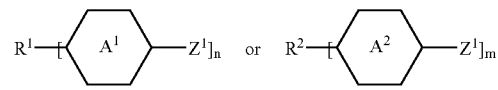

under the formula I, and

Hal is halogen, preferably Br or 1.

A: Hasan, I. et al., Chem. Rev. (2002), 102, pp. 1359-1469,

B: Hennings, D. D. et al., Org. Lett. (1999), 1, pp. 1205-1208.

The ester precursors are synthesised by standard reactions (Houben-Weyl) from commercially available 4-bromo-3-fluoro-1-iodobenzene or (in the case where R=methyl from 4-bromo-2-fluorotoluene, or from 4-bromo-2-fluorophenol (ABCR, Karlsruhe, Germany)).

Alkyl side chains are advantageously introduced into the precursors by Sonogashira coupling as shown in Scheme Ia.

Precursors containing alkoxy side chains are advantageously obtained in accordance with Scheme Ib.

The two types of intermediate obtained in accordance with Scheme Ia or Ib can, as shown in Scheme Ic by way of example for the alkyl compounds, be converted either into the phenol or into the carboxylic acid and subsequently esterified.
Scheme Ia
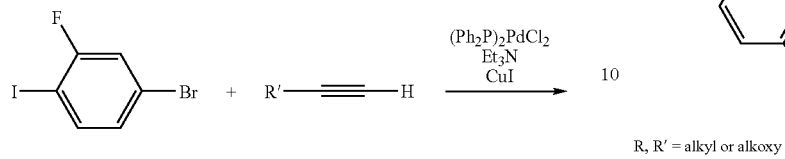
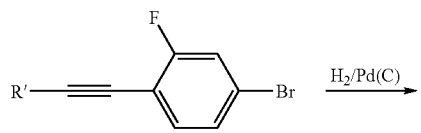
Scheme Ib
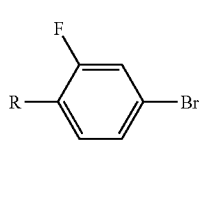
Scheme Ic
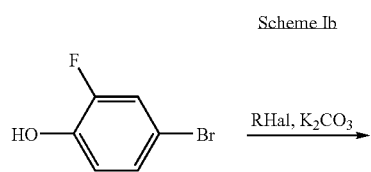
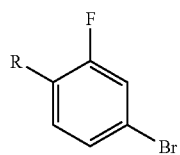 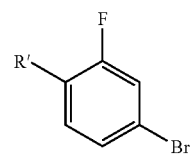
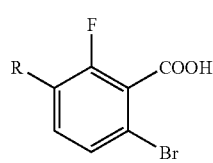 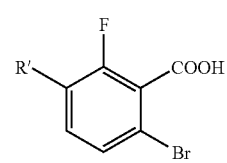
-continued
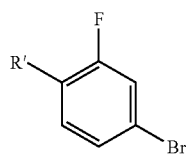
R, R' = alkyl or alkoxy
The bromophenol can be protected and converted into the boronic acid in accordance with Scheme Id for subsequent Suzuki couplings.
Scheme Id
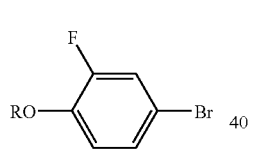
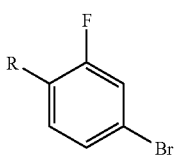 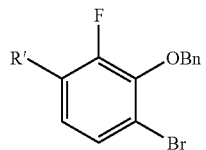
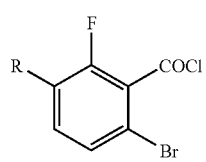 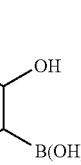
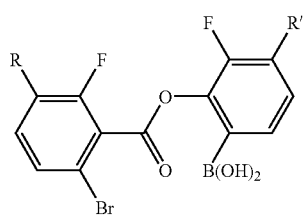

Scheme II

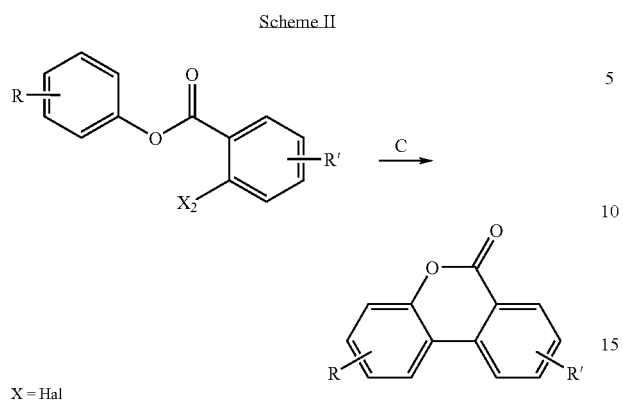

X = Hal

C: Bringmann, G. et al., Org. Synth. (2002), 79, pp. 72-83.

Scheme III

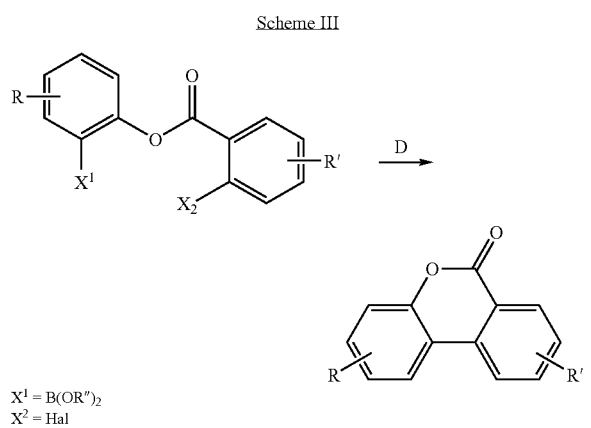

$X^1$ = B(OR")$_2$
$X^2$ = Hal

D: Alo, B. I. et al., J. Org. Chem. (1991), 56, pp. 3763-3768.

The lactones (Ia) can, as shown in Scheme IV, be converted, analogously to EP 1 061 113, into the benzochromenes (1b) or alternatively, using Lawesson's reagent followed by reaction with DAST, into the difluorobenzochromenes (1c) (Bunelle, W. H. et al., J. Org. Chem. (1990), 55, pp. 768-770).

Alternatively, the lactones (1a) can, in accordance with Scheme V (Ringom, R. and Bennecke, T., Acta. Chem. Scand. (1999), 53, pp. 41-47), be reacted with LiAlH$_4$ in THF and subsequently reacted with DAST to give the fluorobenzochromenes (1d).

The above-mentioned alternative synthesis in which the cross-coupling is carried out in a first step with the correspondingly protected phenols and carboxylic acid esters is shown in Scheme IIIa on p. 16 using the example of a Negishi reaction.

Scheme IIIa

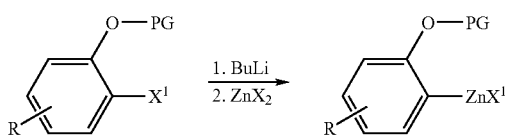

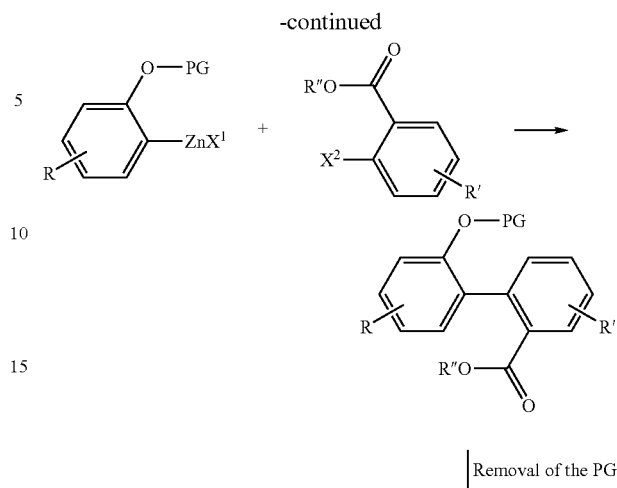

in which

PG is a protecting group,

X is halogen, preferably Br, $X^1$ and $X^2$, independently of one another, are halogen, $X^1$ is preferably Cl, Br or I, particularly preferably Br or I, very particularly preferably Br, R" is alkyl, preferably methyl, and R and R' are each, independently of one another, as defined above for Scheme I.

After removal of the protecting group, the lactones can be obtained, for example, by simple heating in an inert solvent or by treatment with an acid or base.

Scheme IV

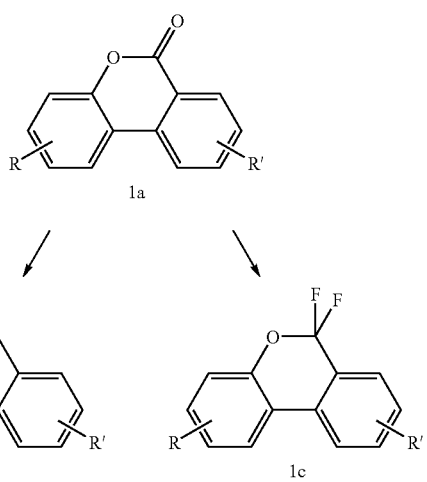

Scheme V
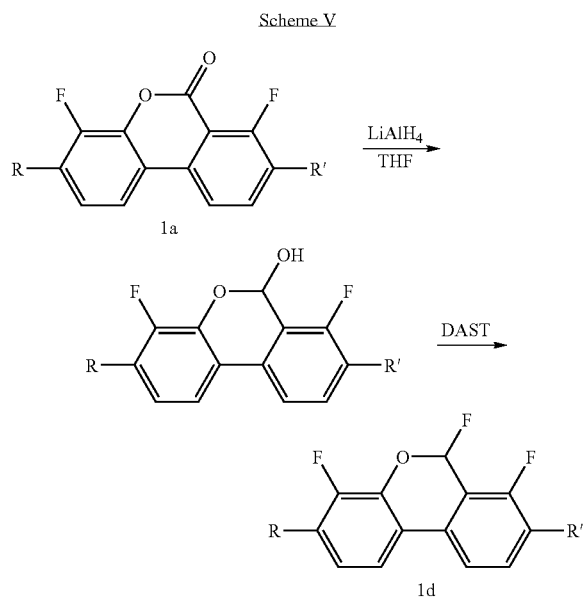
Compounds of the formula I in which
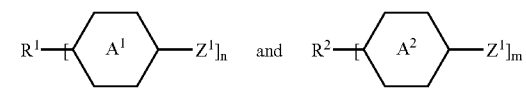  and
are $R^1$, $R^2$,
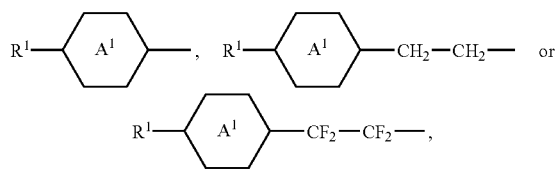  or
in which the
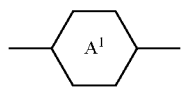
rings may also be heterocyclic rings,
can be obtained in accordance with Schemes VI to XX.
Scheme VI
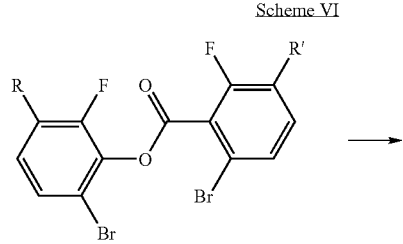
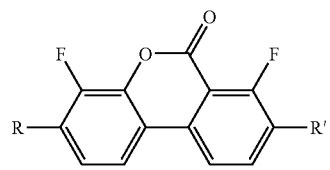
Scheme VII
Scheme VIII
Scheme IX
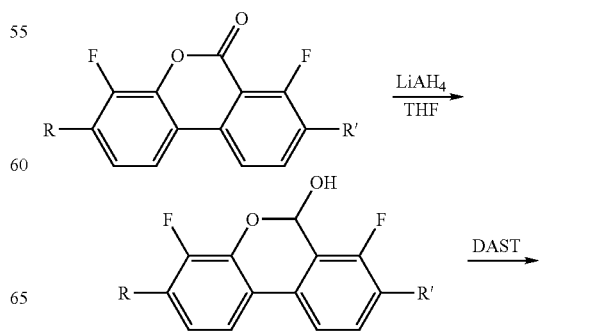

-continued

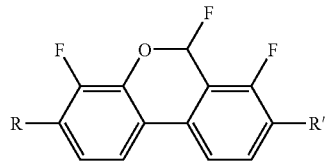

4-Bromo-3-fluoro-1-iodobenzene and 4-bromo-2-fluorophenol are likewise suitable as synthetic building blocks for a multiplicity of derivatives which can be converted into the corresponding target compounds analogously to the reaction sequences shown in Schemes I-V.

Cyclohexyl derivatives are obtained, for example, in accordance with Scheme X. Metallation of 4-bromo-3-fluoro-1-iodobenzene using n-butyllithium and addition onto cyclohexanones gives phenylcyclohexanols, from which 4-bromo-2-fluoro-1-cyclohexylbenzene derivatives are obtained after elimination of water and hydrogenation.

Scheme X

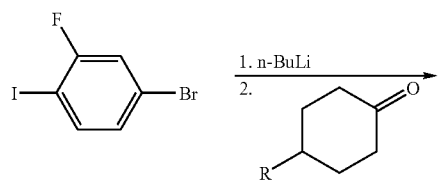

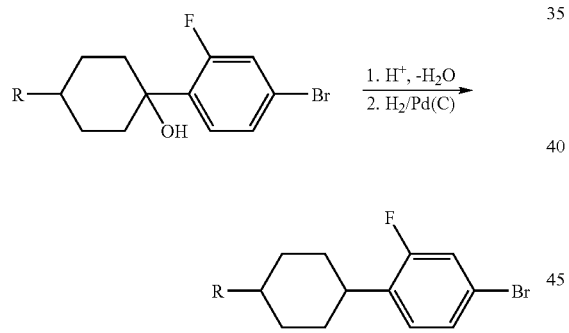

Aryl derivatives are obtained, for example, in accordance with Scheme XI. Direct Suzuki coupling of 4-bromo-3-fluoro-1-iodobenzene with the corresponding boronic acids enables the preparation of 1-aryl-4-bromo-2-fluoro derivatives.

Scheme XI

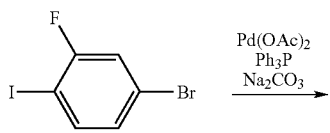

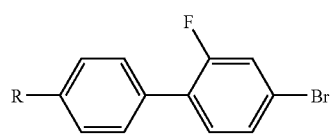

Sonogashira coupling of 4-bromo-3-fluoro-1-iodobenzene with phenylacetylenes gives, as shown in Scheme XII, 4-bromo-2-fluorotolans. These can, as shown in Scheme XIII, either be hydrogenated to give ethylene-bridged compounds or converted into diketones by the method of V. O. Rogatchov, V. D. Filimonov, M. S. Yusubov, Synthesis (2001), 7, 1001-1003, from which tetrafluoroethylene-bridged compounds are obtained by reaction with sulfur tetrafluoride.

Scheme XII

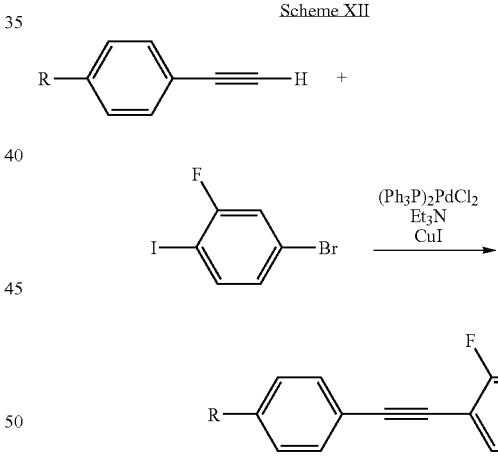

Scheme XIII

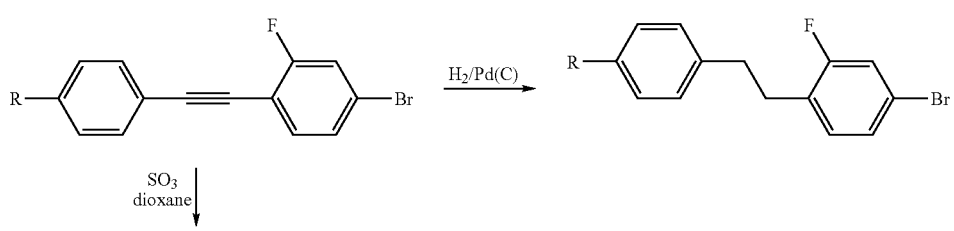

-continued

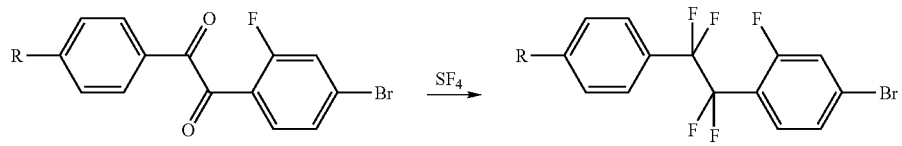

From 4-bromo-2-fluorophenol, hydroxyl compounds and triflates can be obtained as synthetic building blocks in accordance with Scheme XIV.

4-Bromo-2-fluorophenol is protected here using a suitable protecting group "PG" (for example benzyl); corresponding reaction in accordance with Schemes I to V and subsequent removal of the protecting group (for example by hydrogenation for benzyl as PG) enables the preparation of phenols and from these triflates (trifluoromethanesulfonates, TfO-).

Scheme XIV

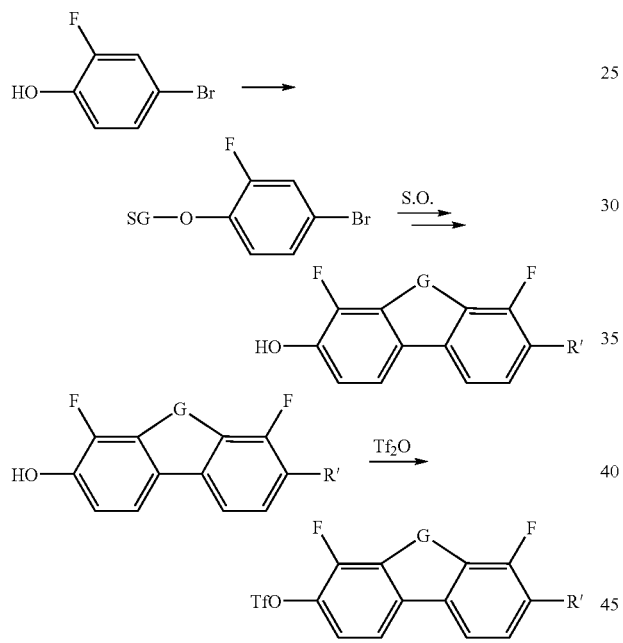

in which, as in Schemes XV to XX,
G is Y—O or O—Y, and
Y is as defined above under the formula I.

The phenols obtained in this way can be converted into esters and ethers in accordance with Scheme XV.

Scheme XV

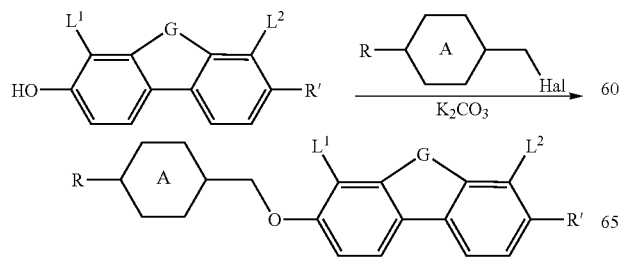

-continued

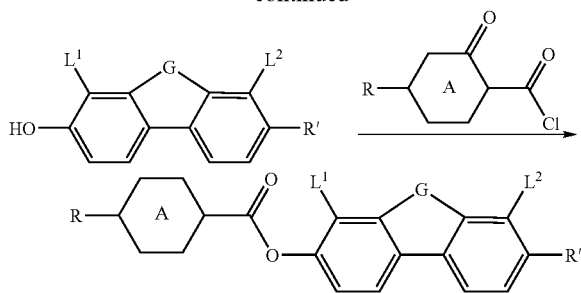

in which R, as in Schemes XVI to XX, is as defined for $R^1$ under the formula I.

$CF_2O$-bridged compounds are obtained in accordance with WO 02/48 073 and WO 01/64 667, as shown in Scheme XVI.

Scheme XVI

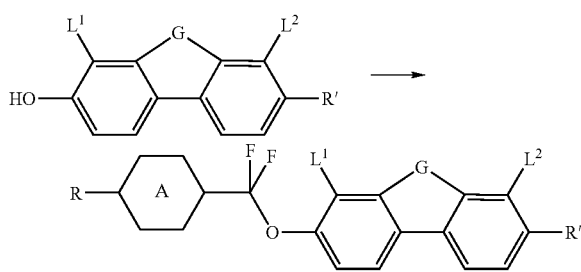

Suzuki coupling of the triflates obtained in accordance with Scheme XIV with etheneboronic acids enables the preparation of stilbenes (Scheme XVII).

Scheme XVII

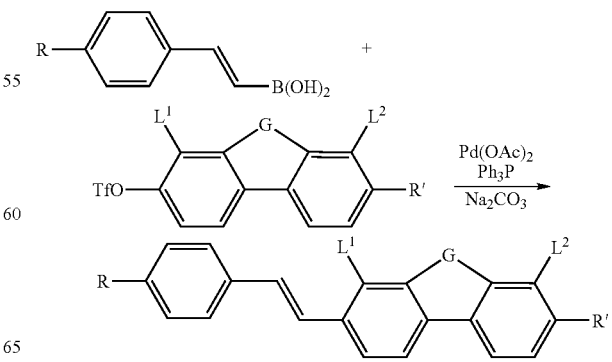

Difluorostilbenes are accessible analogously by Stille reaction as described by L. Lu, D. J. Burton, Tetrahedron Lett. 1997, 38, 7673-7676, (Scheme XVIII).

Scheme XVIII

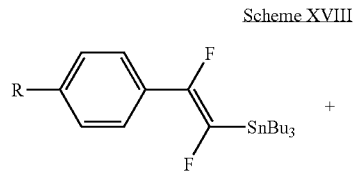

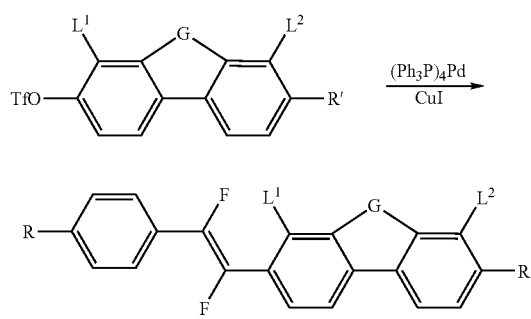

Carbonylation of triflates by the method of S. Cacchi, P. G. Ciattini, E. Morera, G. Ortar, Tetrahedron Lett. (1986), 27, 3931-3934 gives carboxylic acid esters (Scheme XIX). After saponification to the corresponding carboxylic acids, reaction thereof with-phenols enables the preparation of, for example, phenyl esters.

Scheme XIX

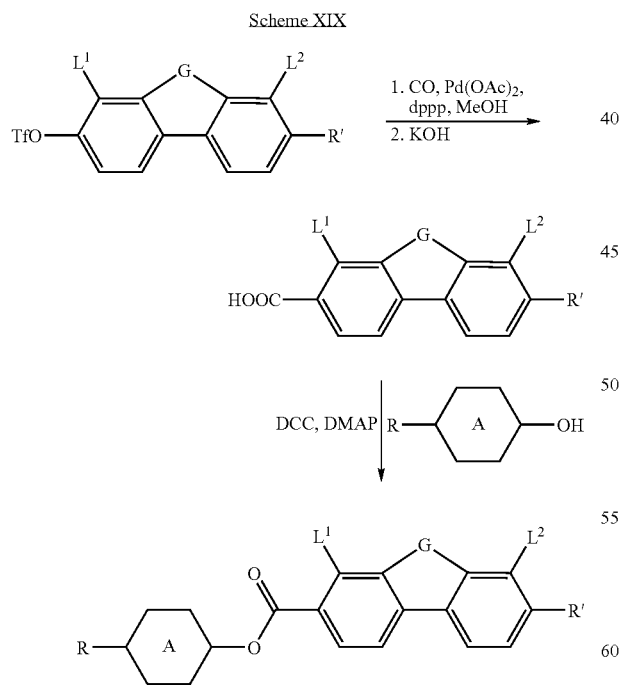

The carboxylic acid esters obtained in accordance with Scheme XIX can be converted into difluorobenzyl ethers in accordance with WO 02/480 73 and WO 01/64 667, as shown in Scheme XX.

Scheme XX

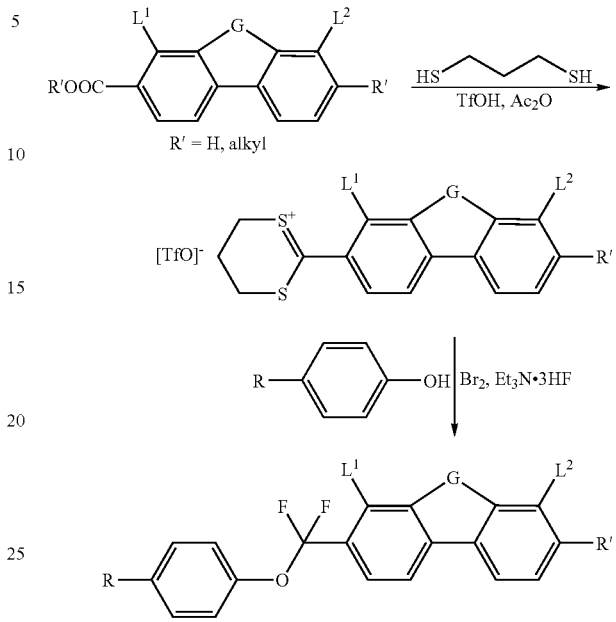

Examples of structures of preferred compounds of the formula I, in which R and $R^1$ have the respective meaning given for $R^1$ and $R^2$ respectively under the formula I, are given on the following pages.

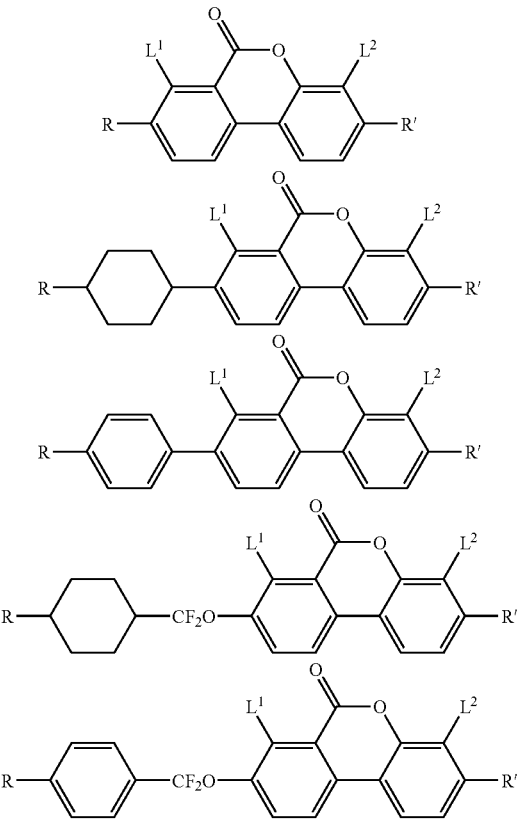

-continued
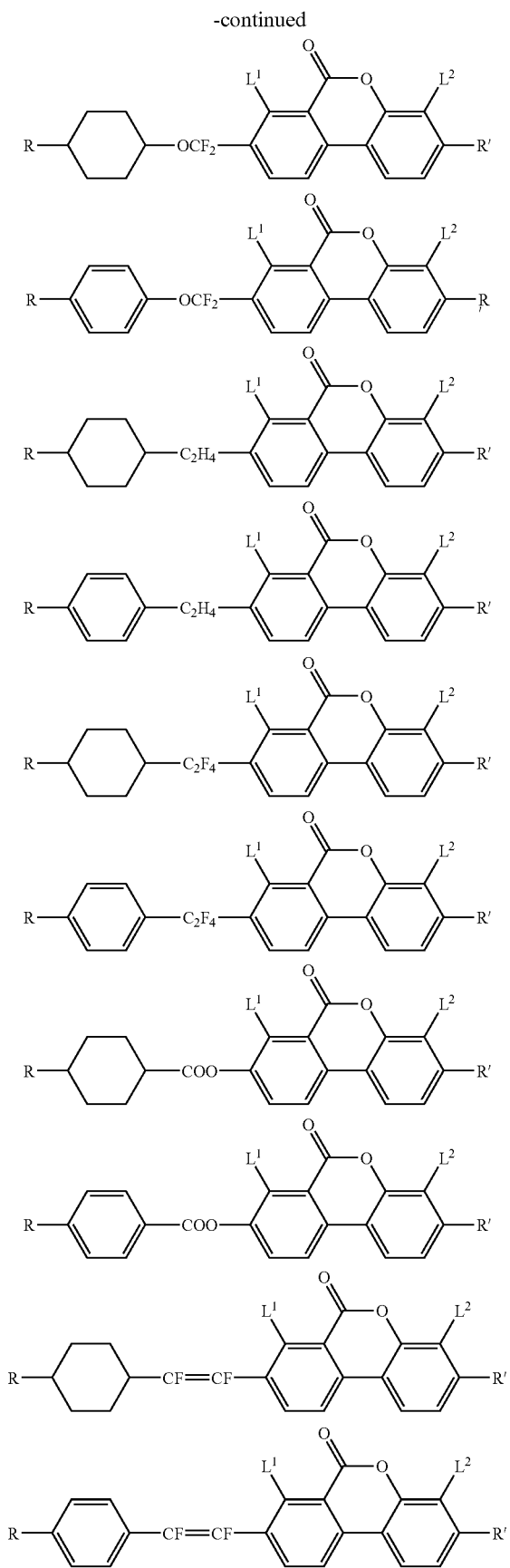
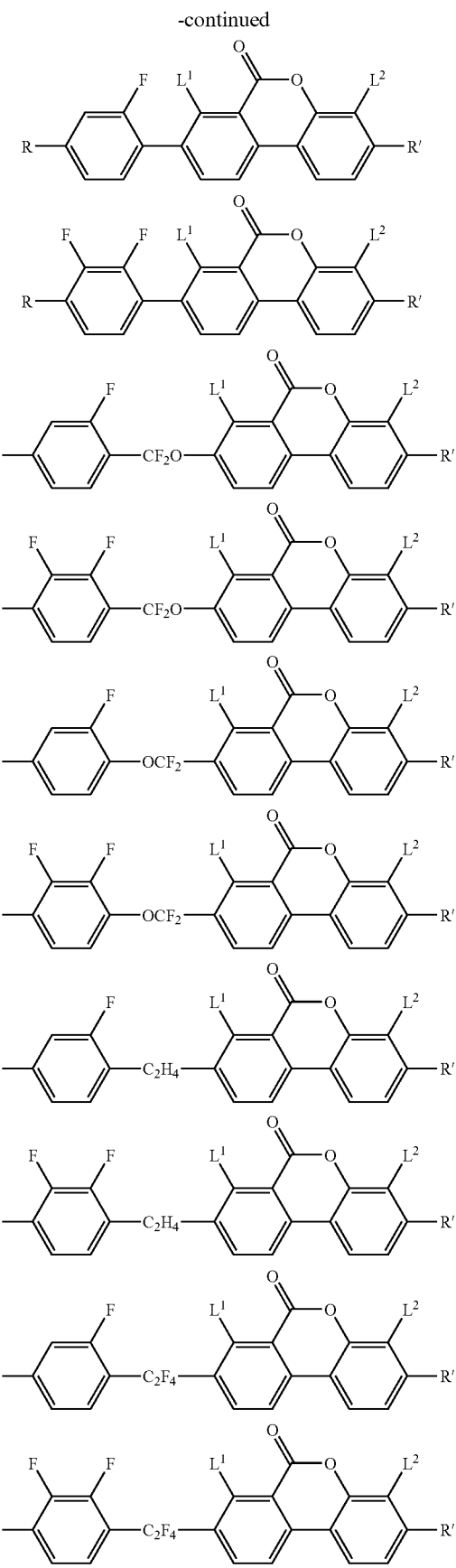

-continued
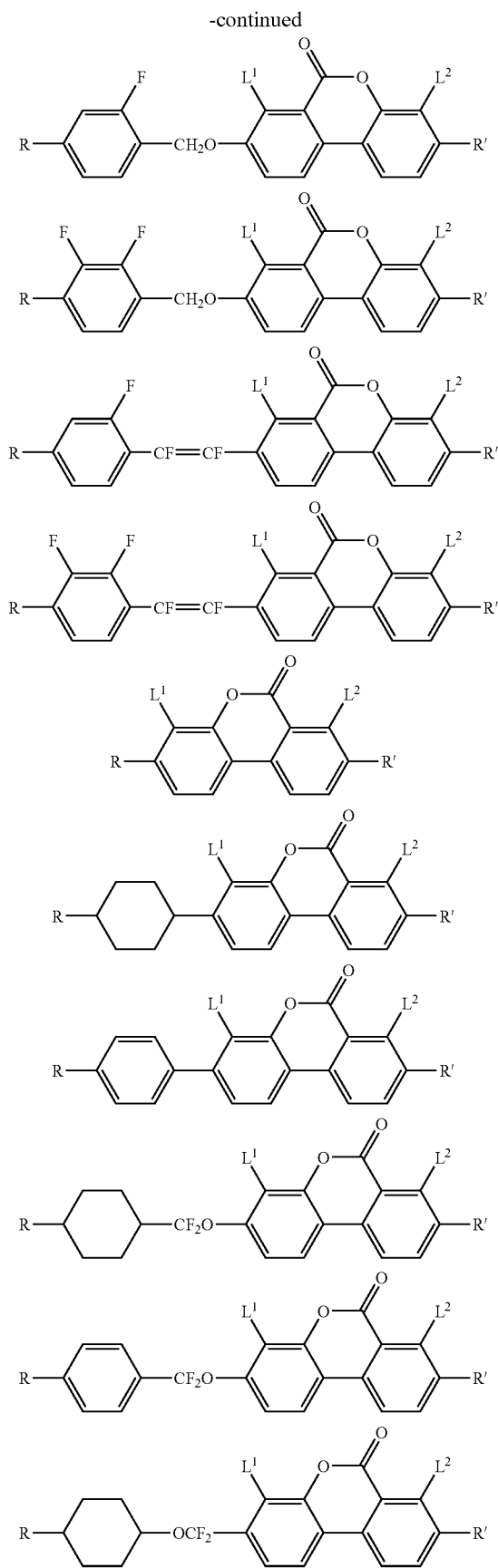
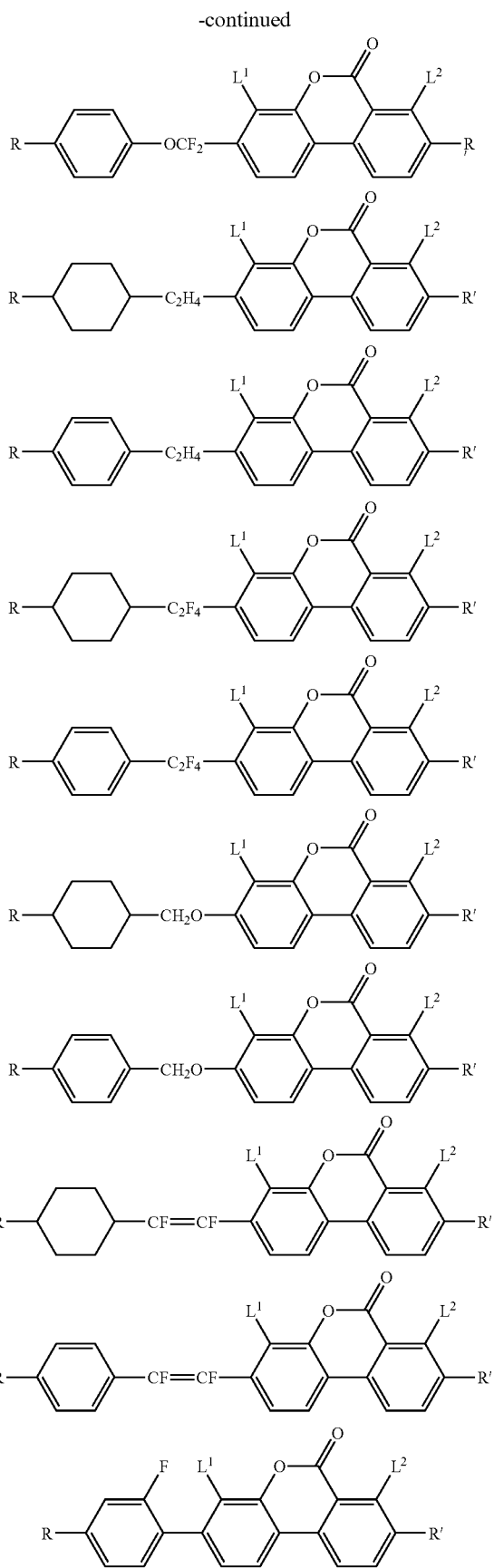

-continued
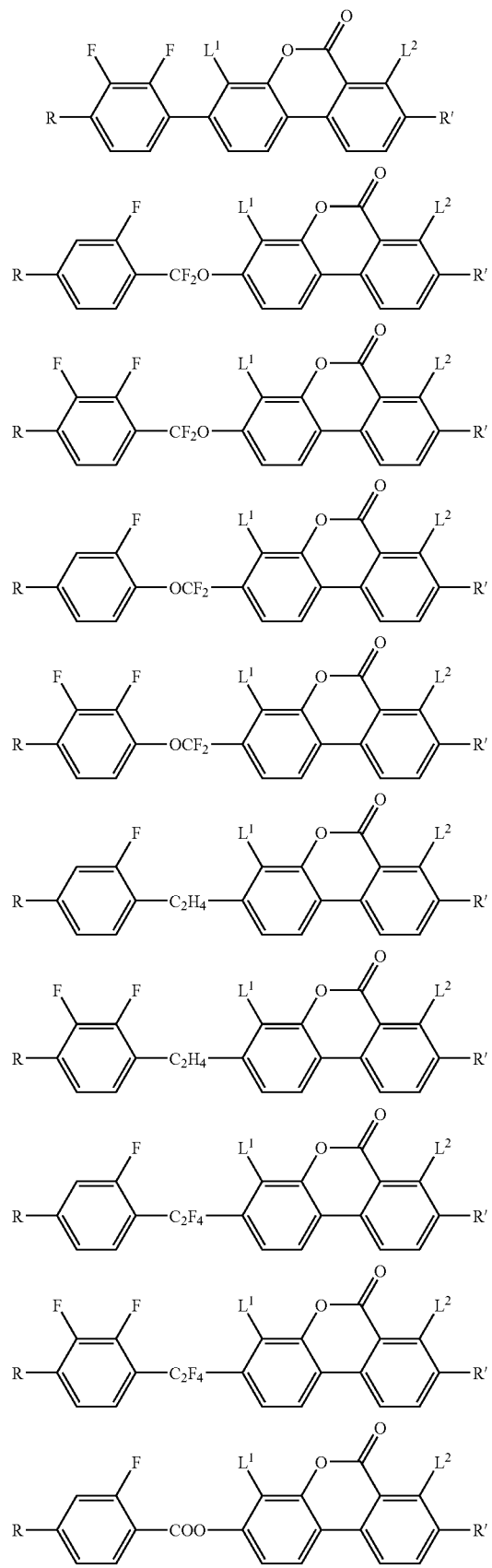
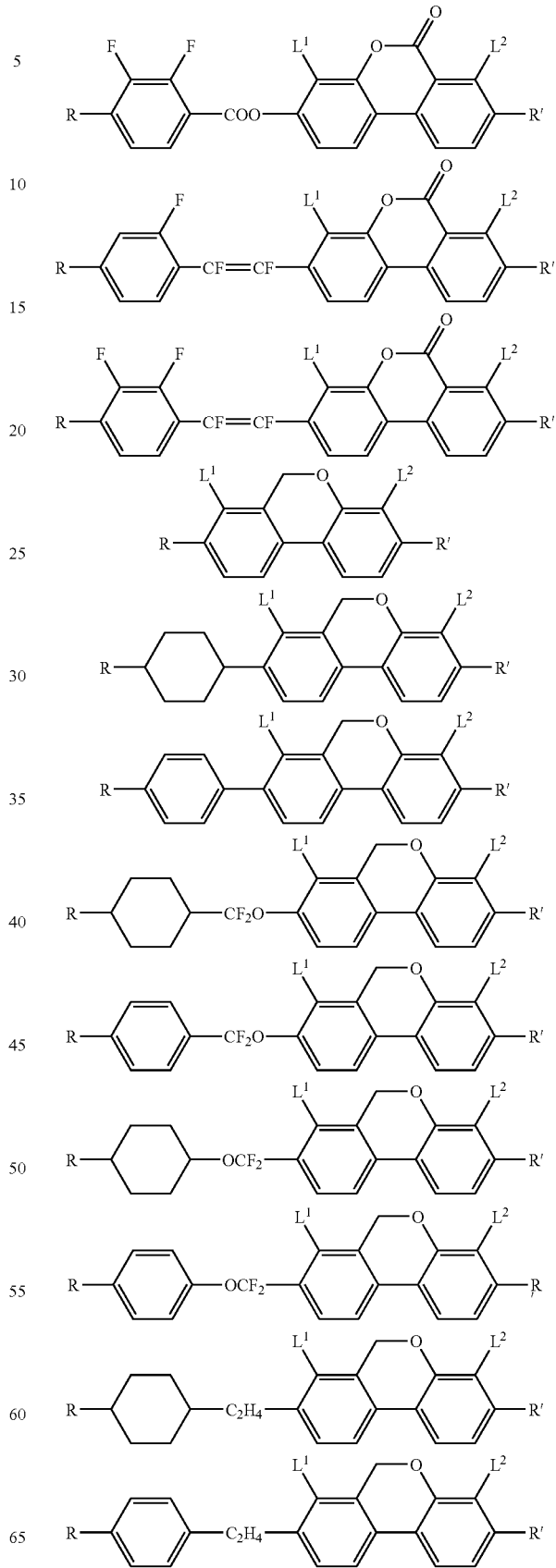

-continued
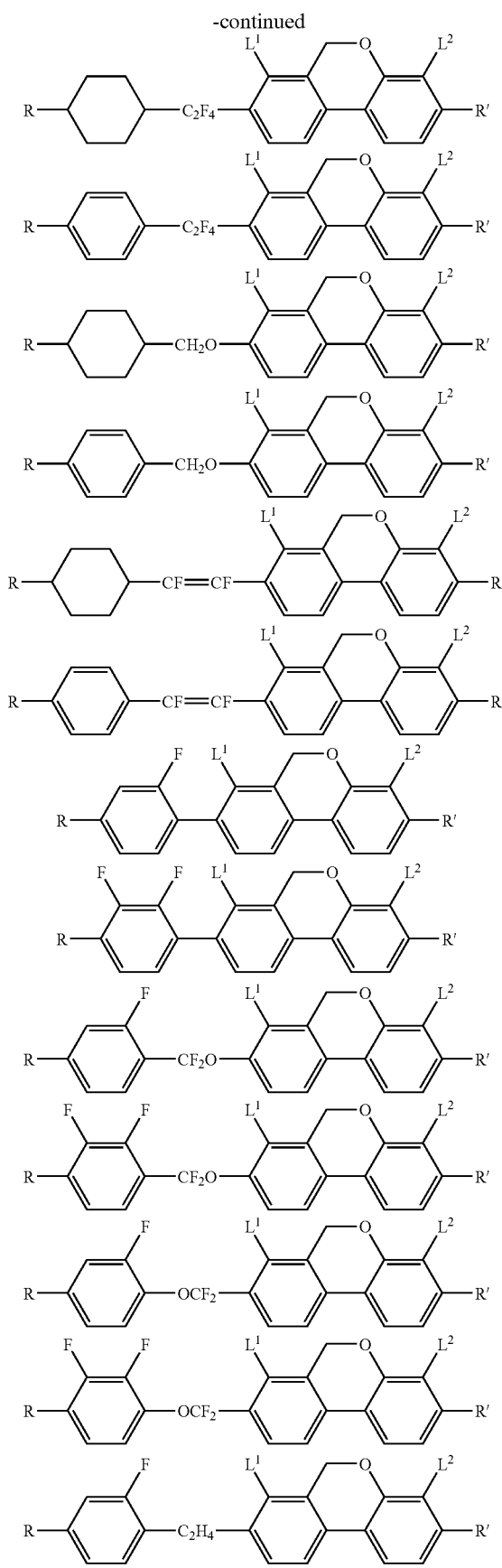
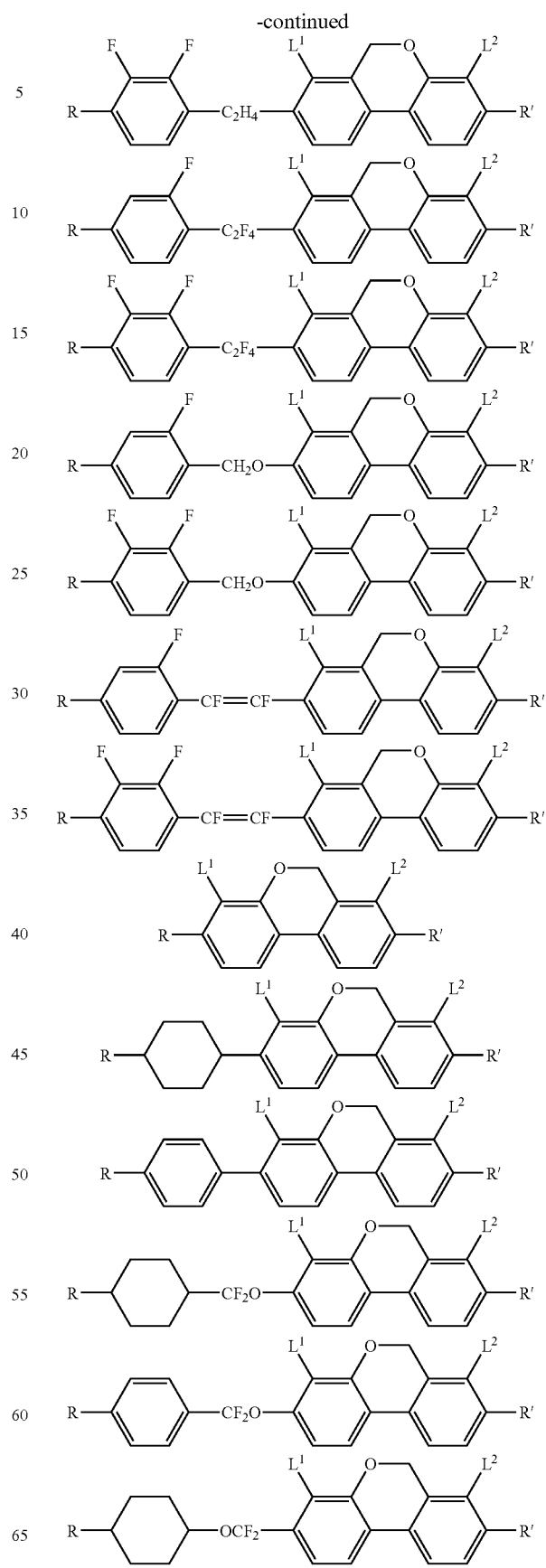

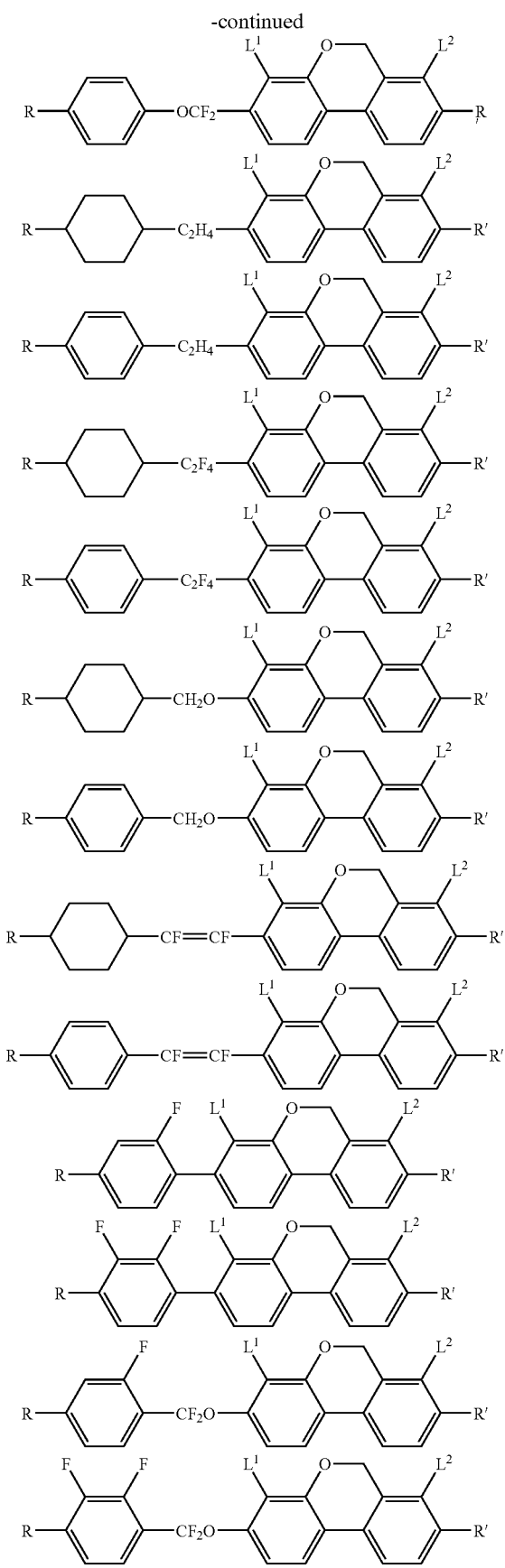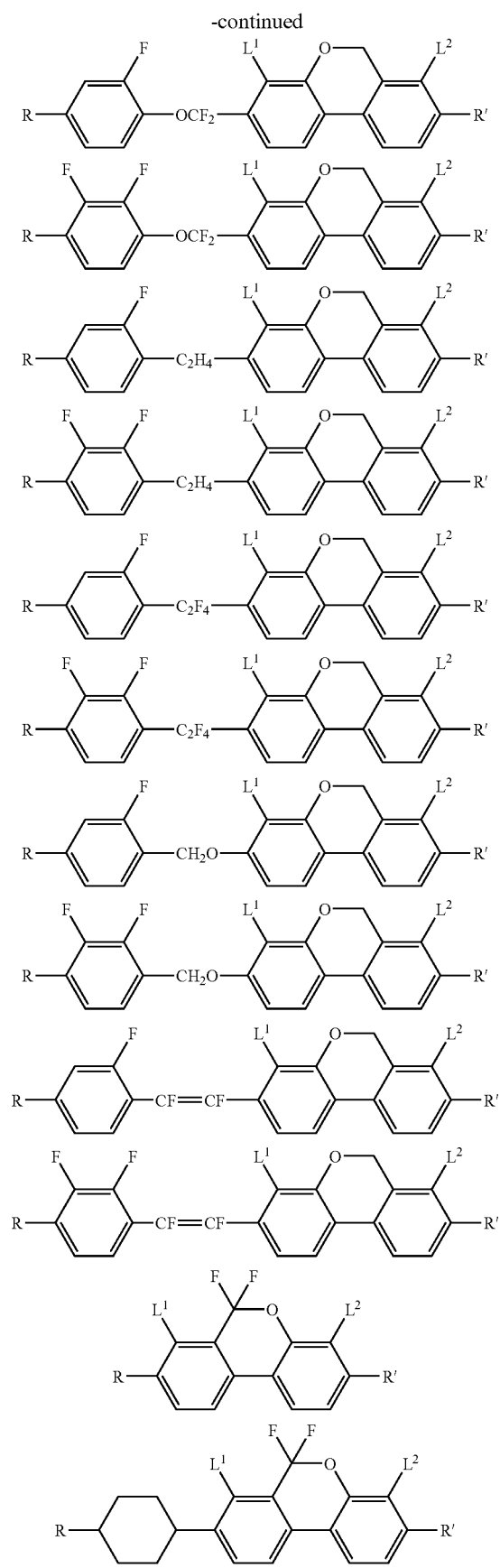

-continued
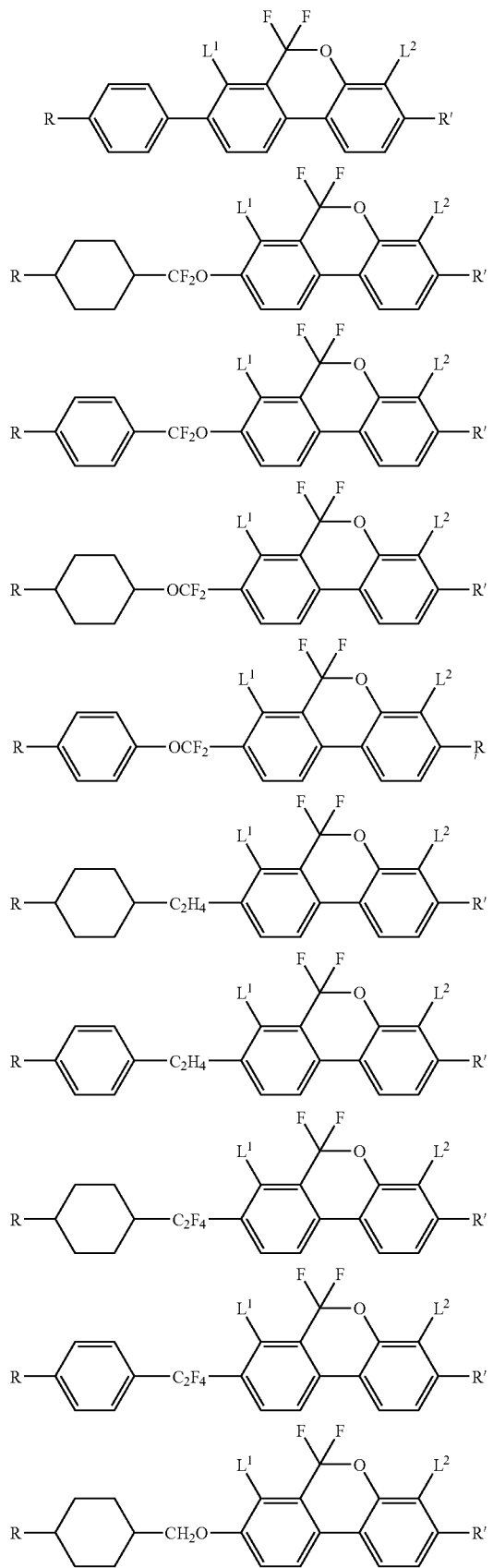
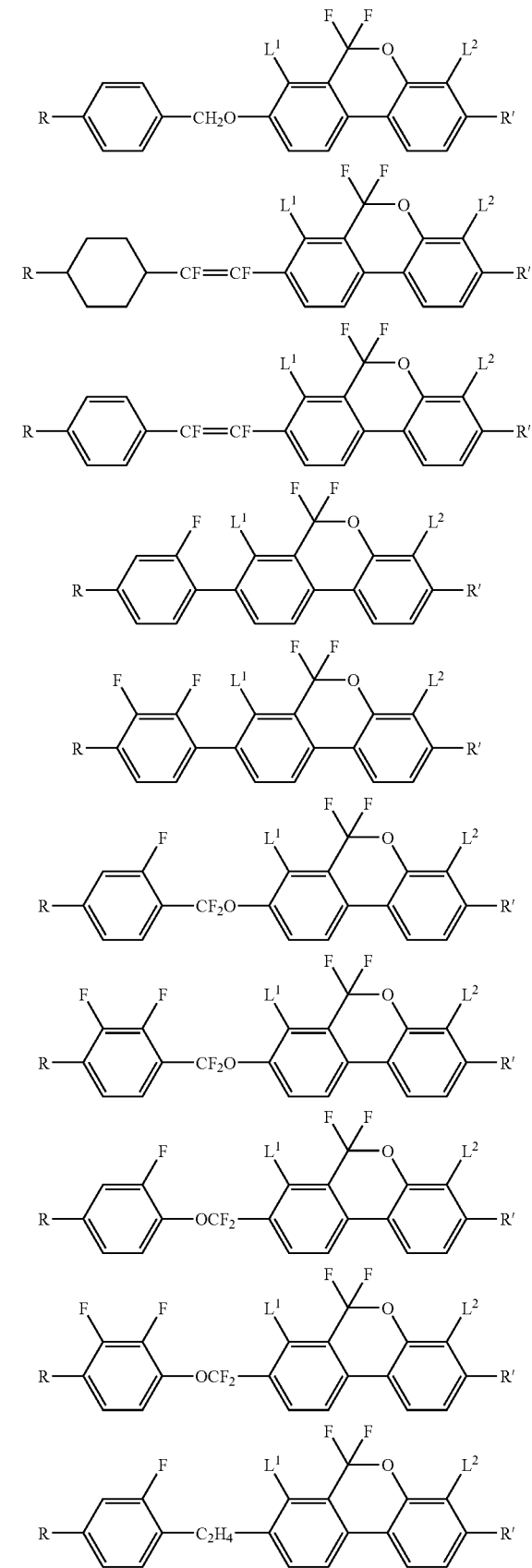

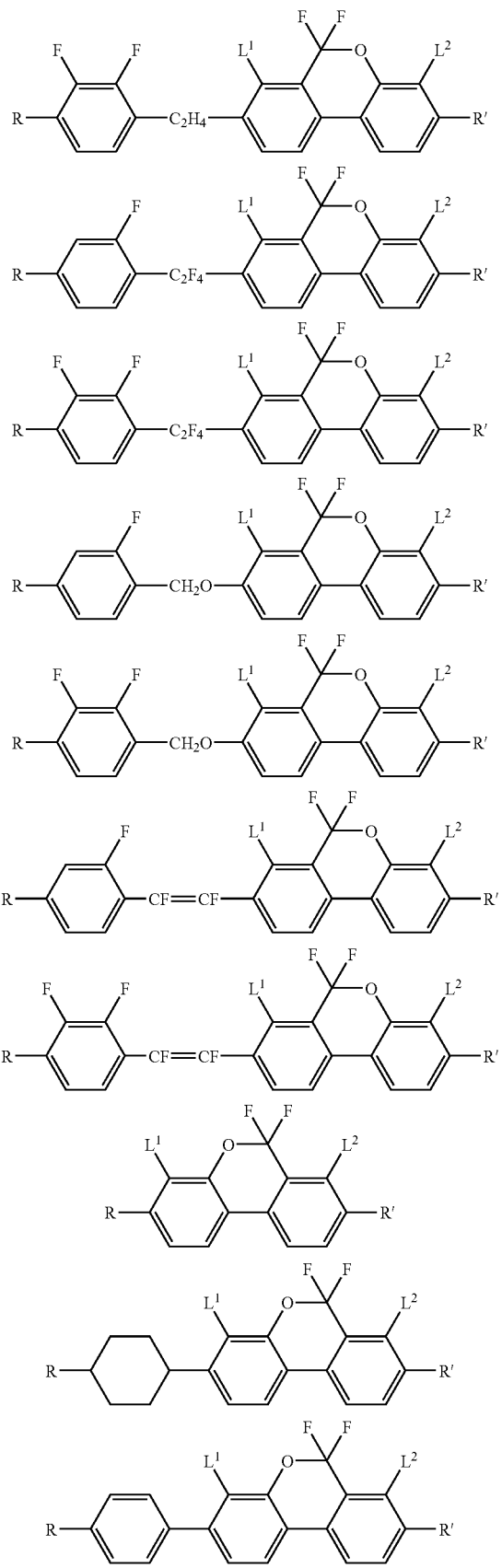
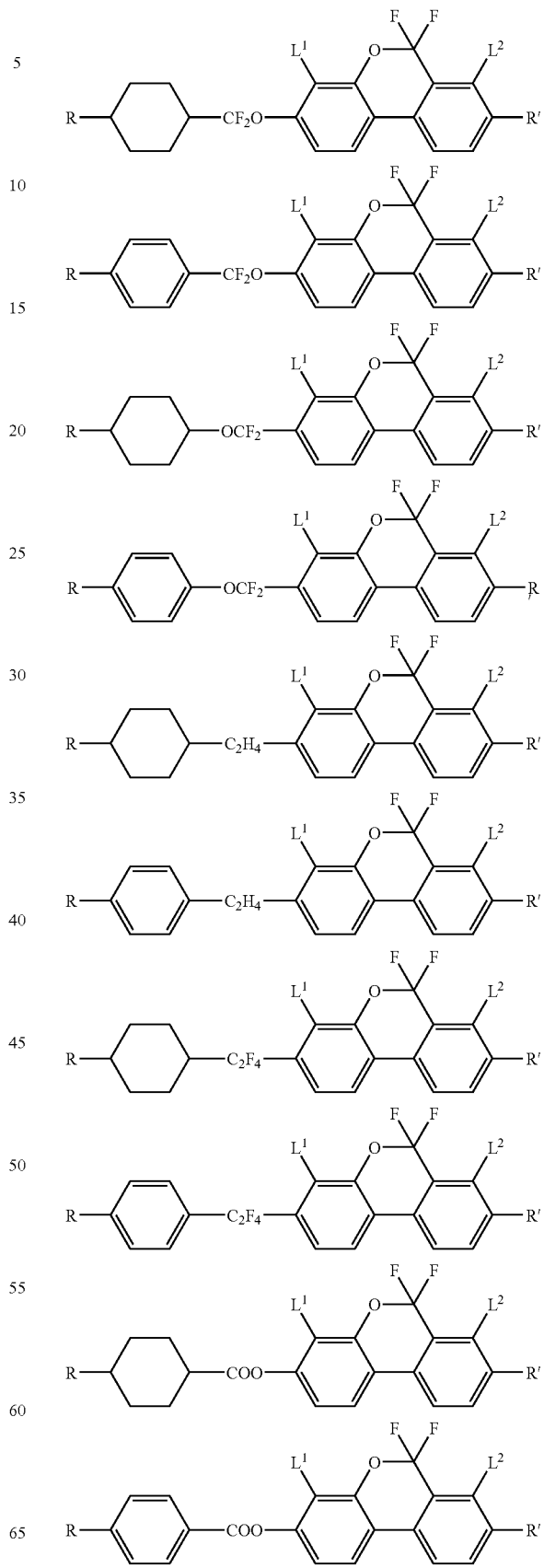

-continued
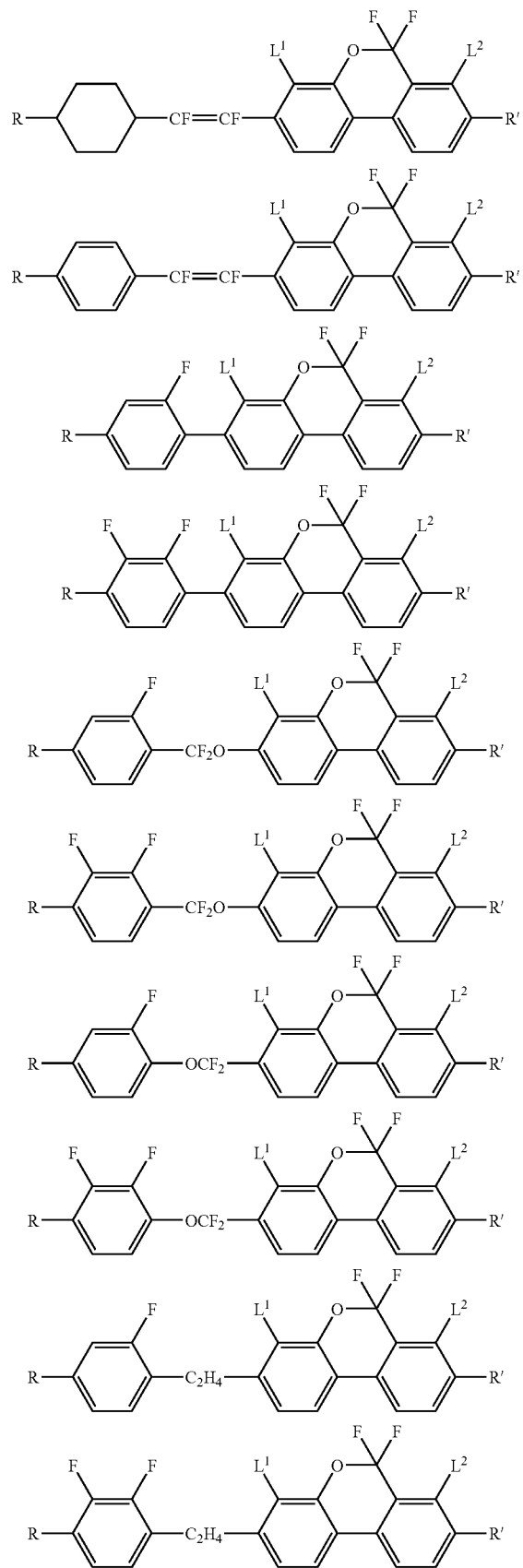
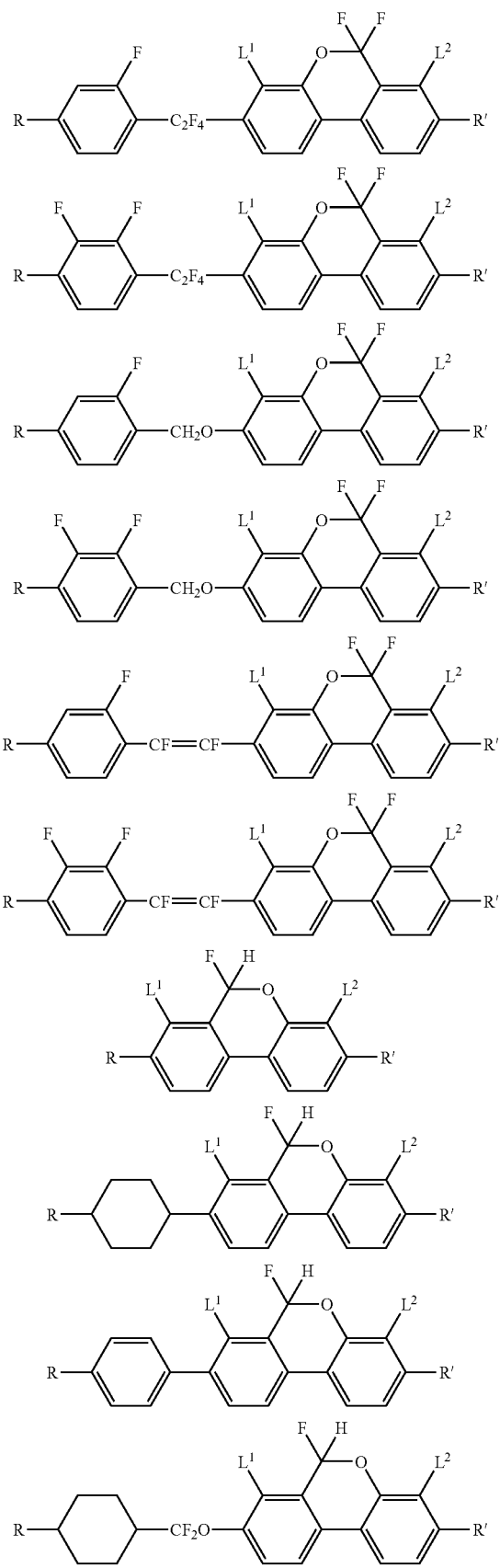

-continued
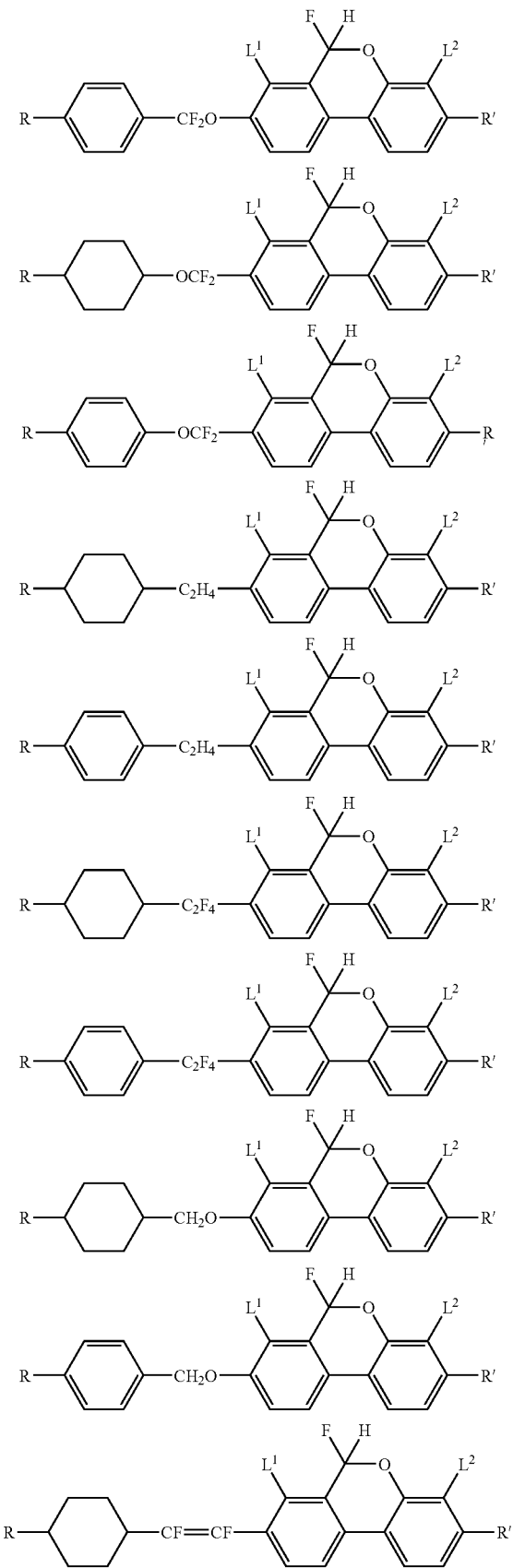
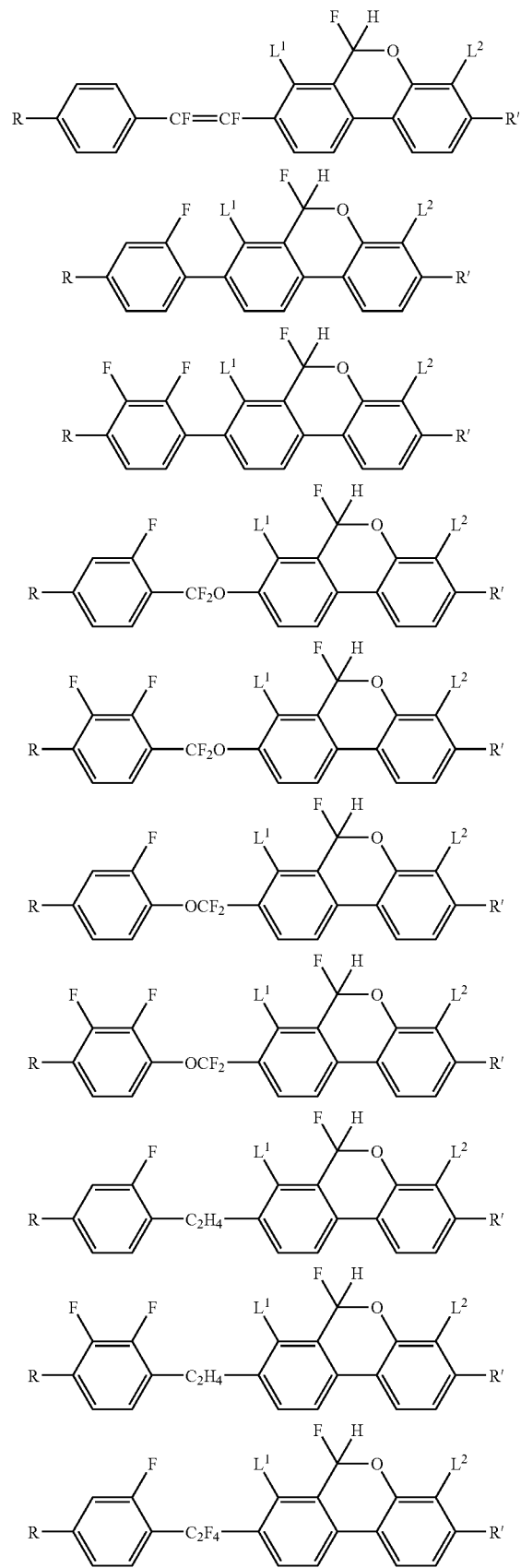

-continued
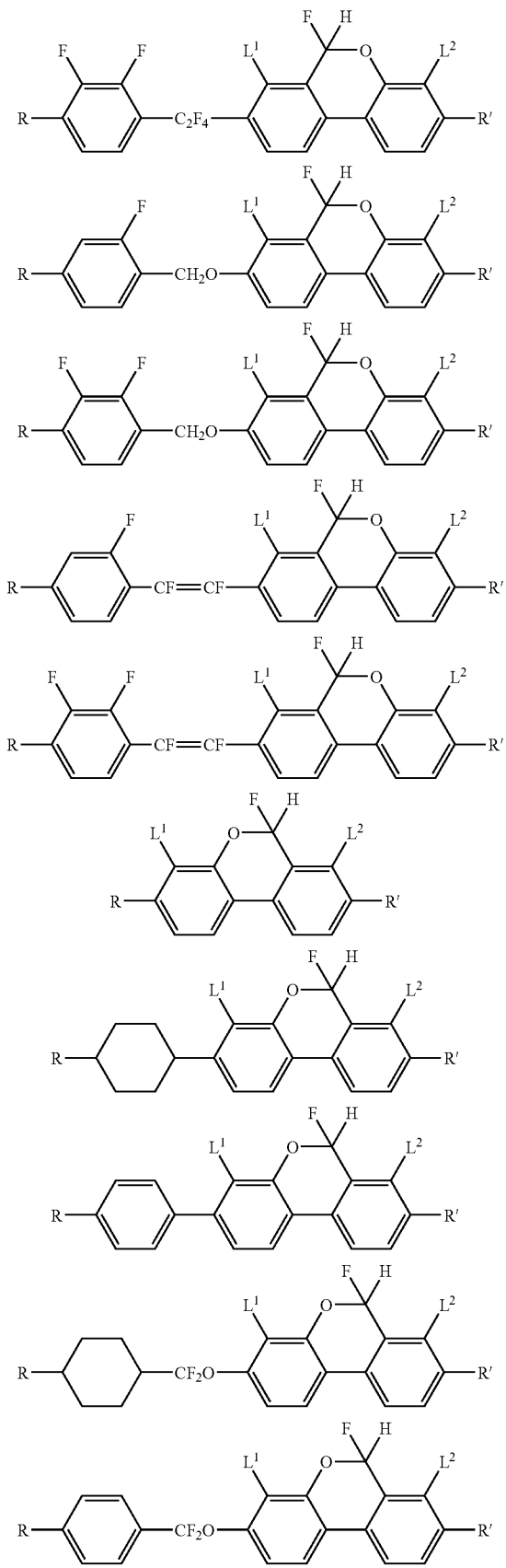
-continued
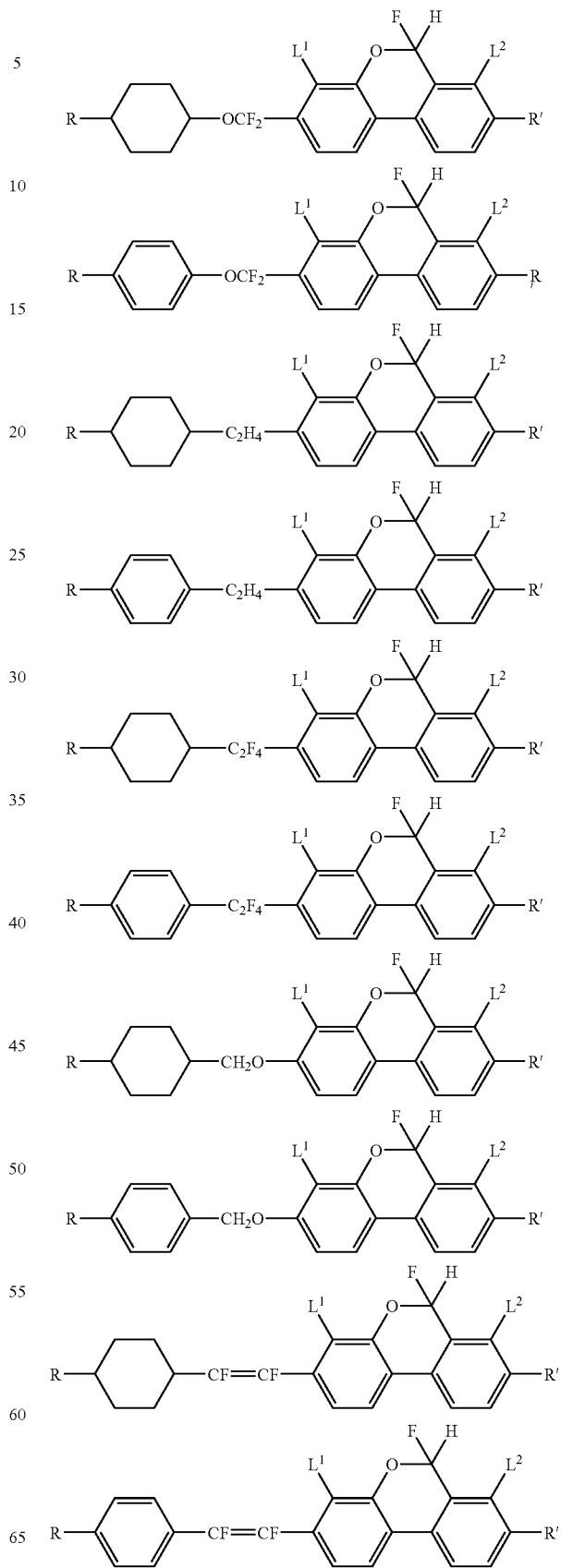

-continued

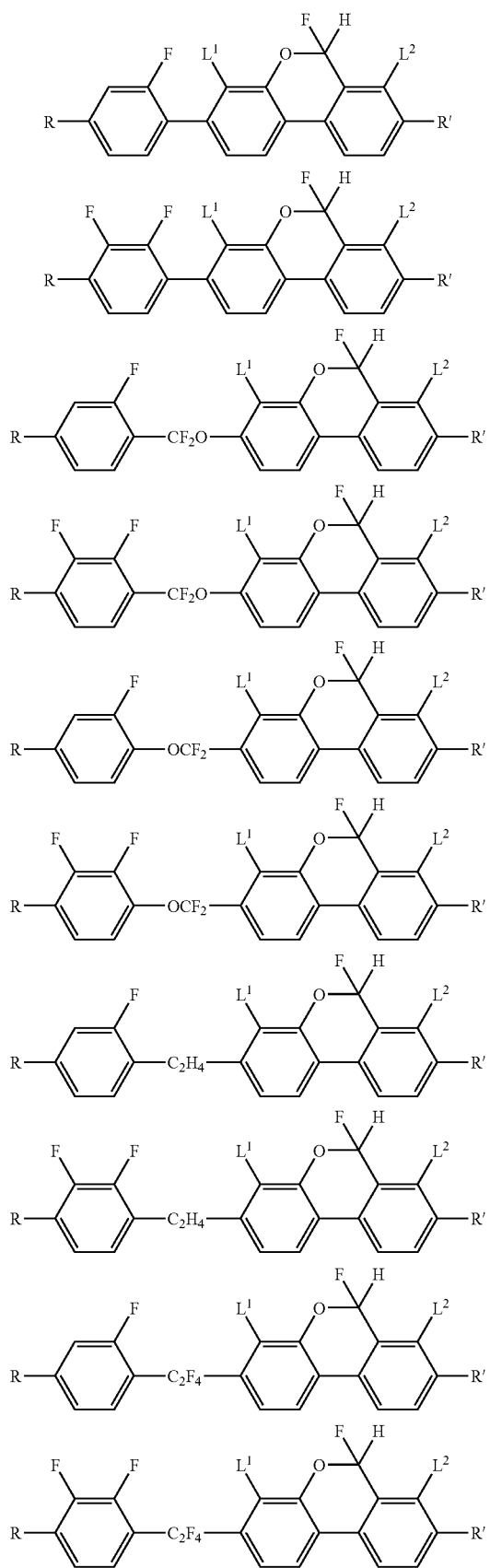

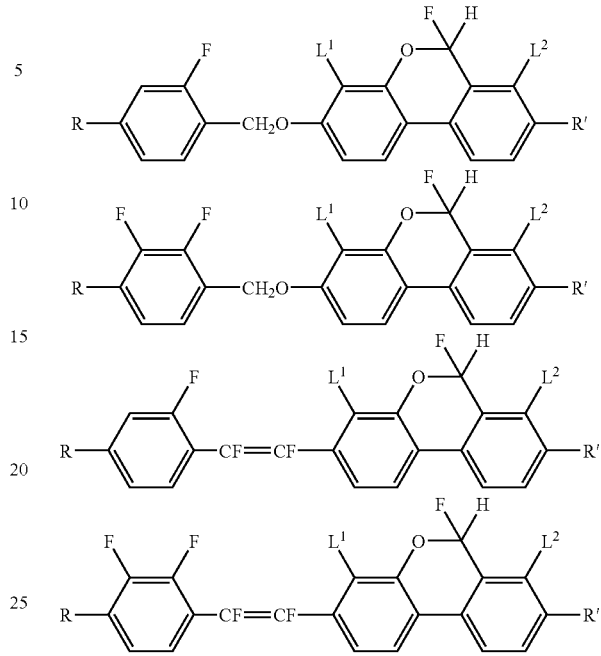

The liquid-crystal media according to the invention comprise one or more compounds of the formula I.

In a preferred embodiment, the liquid-crystal media in accordance with the present invention comprise a) one or more dielectrically negative compound(s) of the formula I

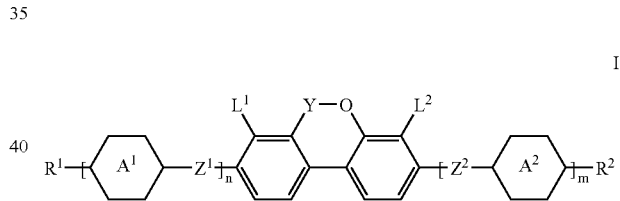

I in which

Y is —CO—, —CS—, —CH$_2$—, —CF$_2$— or —CHF—, preferably —CF$_2$—,

L$^1$ and L$^2$ are each, independently of one another, H, F, Cl or —CN, preferably H or F, preferably at least one of L$^1$ and L$^2$ is F, particularly preferably L$^1$ and L$^2$ are both F,

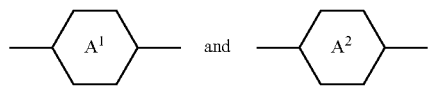

are each, independently of one another, and, if present more than once, also independently of one another, (a) a trans-1,4-cyclohexylene radical, in which, in addition, one or two non-adjacent CH$_2$ groups may be replaced by —O— and/or —S—, (b) a 1,4-cyclohexenylene radical, (c) a 1,4-phenylene radical, in which, in addition, one or two non-adjacent CH groups may be replaced by N, or (d) a radical selected from the group consisting of 1,4-bicyclo[2.2.2]octylene, 1,3-bicyclo[1.1.1]pentylene, spiro[3.3]heptane-2,4-diyl, piperidine-1,4-diyl, naphthalene-2,6-diyl, decahydronaphthalene-2,6-diyl and 1,2,3,4-tetrahydronaphthalene-2,6-diyl, preferably

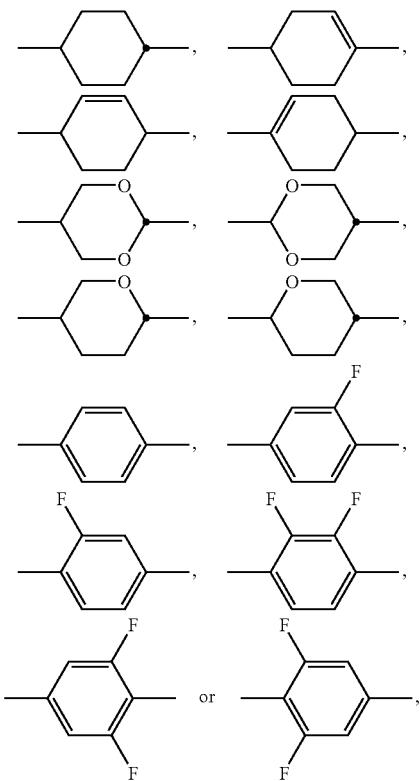

$R^1$ and $R^2$ are each, independently of one another, H, halogen, —CN, —SCN, —SF$_5$, —CF$_3$, —CHF$_2$, —CH$_2$F, —OCF$_3$, —OCHF$_2$, or an alkyl group having from 1 to 15 carbon atoms which is monosubstituted by CN or CF$_3$ or at least monosubstituted by halogen and in which, in addition, one or more CH$_2$ groups may each, independently of one another, be replaced by —O—, —S—, —CH=CH—, —CF=CF—, —CF=CH—, —CH=CF—,

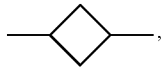

—CO—, —CO—O—, —O—CO— or —O—CO—O— in such a way that neither O nor S atoms are linked directly to one another,
preferably one of
$R^1$ and $R^2$ is alkyl or alkoxy having from 1 to 12 carbon atoms, alkoxyalkyl, alkenyl or alkenyloxy having from 2 to 12 carbon atoms and the other, independently of the first, is likewise alkyl or alkoxy having from 1 to 12 carbon atoms, alkoxyalkyl, alkenyl or alkenyloxy having from 2 to 12 carbon atoms or alternatively F, Cl, Br, —CN, —SCN, —SF$_5$, —CF$_3$, —CHF$_2$, —CH$_2$F, —OCF$_3$ or —OCHF$_2$,
$Z^1$ and $Z^2$ are each, independently of one another, a single bond, —CH$_2$—CH$_2$—, —CF$_2$—CF$_2$—, —CF$_2$—CH$_2$—, —CH$_2$—CF$_2$—, —CH=CH—, —CF=CF—, —CF=CH—, —CH=CF—, —C≡C—, —COO—, —OCO—, —CH$_2$O—, —OCH$_2$—, —CF$_2$O—, —OCF$_2$—, or a combination of two of these groups, where no two O atoms are bonded to one another,
preferably —(CH$_2$)$_4$—, —CH$_2$—CH$_2$—, —CF$_2$—CF$_2$—, —CH=CH—, —CF=CF—, —C≡C—, —CH$_2$O—, —CF$_2$O— or a single bond,
particularly preferably —CH$_2$O—, —CH$_2$—CH$_2$—, —CF$_2$—CF$_2$—, —CF=CF—, —CF$_2$O— or a single bond, and
n and m are each 0, 1 or 2, where
n+m is 0, 1, 2 or 3, preferably 0, 1 or 2, particularly preferably 0 or 1,
b) one or more dielectrically negative compound(s) of the formula II

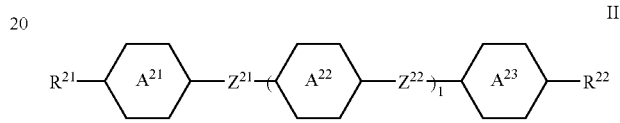

in which
$R^{21}$ and $R^{22}$ are each, independently of one another, as defined above for $R^1$ under the formula I,
$Z^{21}$ and $Z^{22}$ are each, independently of one another, as defined above for $Z^1$ under the formula I,
at least one of the rings present

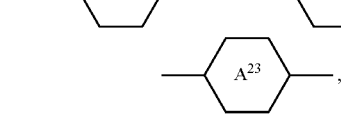

preferably

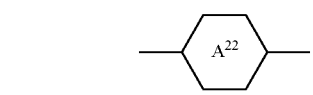

and

is

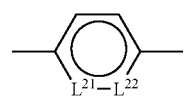

and the others are each, independently of one another,

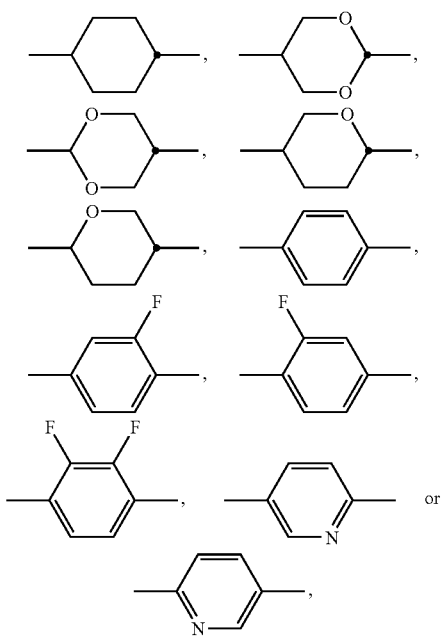

preferably

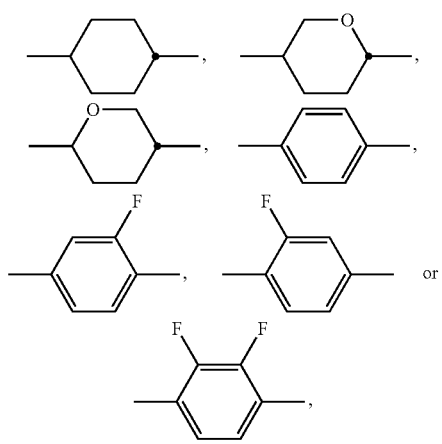

particularly preferably

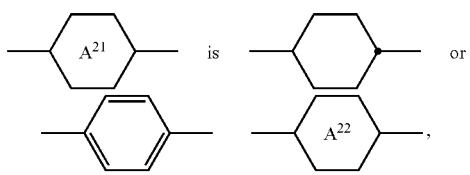

if present, is

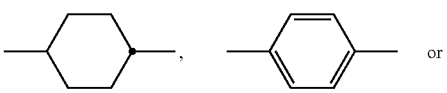

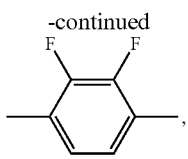

very particularly preferably one of

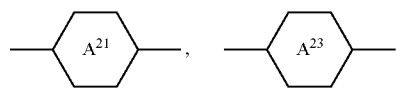

and, if present,

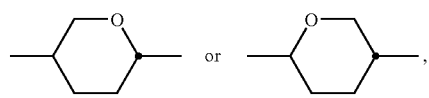

preferably

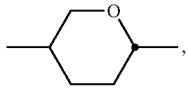

$L^{21}$ and $L^{22}$ are both C—F or one of the two is N and the other is C—F, preferably both are C—F, and l is 0, 1 or 2, preferably 0 or 1;

and optionally c) one or more dielectrically neutral compound(s) of the formula III

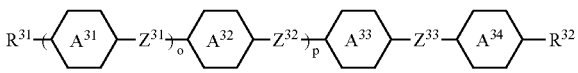

III in which $R^{31}$ and $R^{32}$ are each, independently of one another, as defined above for $R^1$ under the formula I, and $Z^{31}$, $Z^{32}$ and $Z^{33}$ are each, independently of one another, —CH$_2$CH$_2$—, —CH═CH—, —COO— or a single bond,

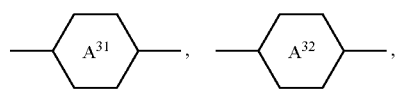

-continued

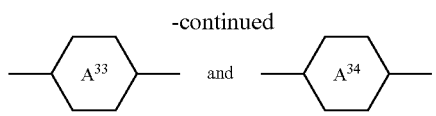

are each, independently of one another,

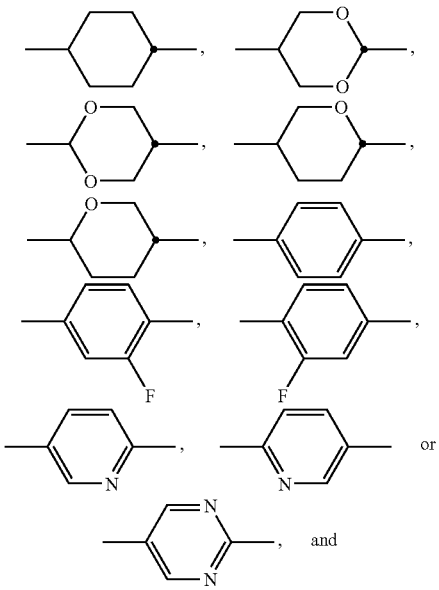

o and p, independently of one another, are 0 or 1, but preferably $R^{31}$ and $R^{32}$ are each, independently of one another, alkyl or alkoxy having 1-5 carbon atoms or alkenyl having 2-5 carbon atoms,

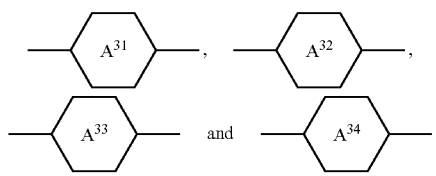

are each, independently of one another,

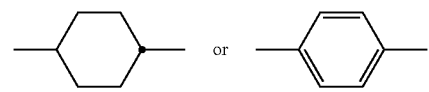

and very particularly preferably at least two of these rings are

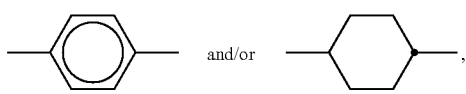

where very particularly preferably two adjacent rings, preferably

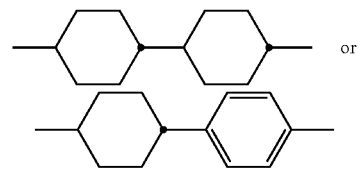

are linked directly.

The liquid-crystal media preferably comprise one or more compounds of the formula I which do not contain a biphenyl unit.

The liquid-crystal media particularly preferably comprise one or more compounds of the formula I
in which two adjacent rings, preferably

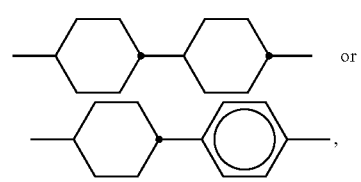

are linked directly.

In a preferred embodiment, which may be identical with the embodiments just described, the liquid-crystal media comprise one or more compounds selected from the group consisting of the compounds of the formula I-3.

The liquid-crystal medium preferably comprises one or more compounds selected from the group consisting of the compounds of the formulae II-1 to II-3

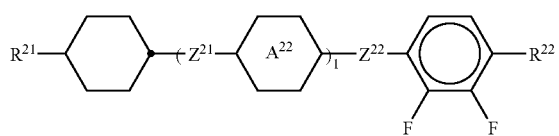

II-1

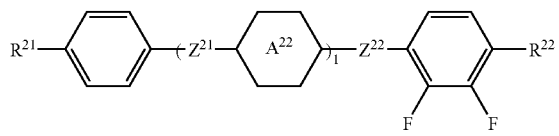

II-2

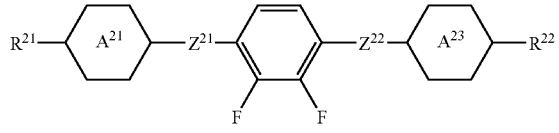

II-3 in which
$R^{21}$, $R^{22}$, $Z^{21}$, $Z^{22}$,

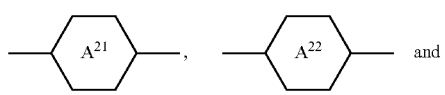

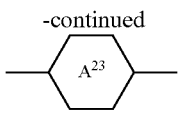

and I are each as defined above under the formula II. $R^{21}$ is preferably alkyl, preferably having 1-5 carbon atoms, $R^{21}$ is preferably alkyl or alkoxy, preferably each having from 1 to 5 carbon atoms, and $Z^{22}$ and $Z^{21}$, if present, are preferably a single bond.

The liquid-crystal medium particularly preferably comprises one or more compounds selected from the group consisting of the compounds of the formulae III-1 to III-3:

III-1

III-2

III-3 in which $R^{31}$, $R^{32}$, $R^{31}$, $Z^{32}$

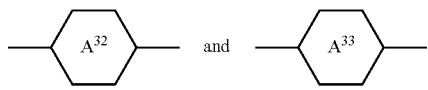

are each as defined above under the formula III.

The liquid-crystal medium especially preferably comprises one or more compounds selected from the group consisting of the compounds of the formulae III-1a to III-1d, III-1e, III-2a to III-2g, III-3a to III-3d and III-4a:

III-1a n-$C_nH_{2n+1}$—⬡—⬡—O—n-$C_mH_{2m+1}$

III-1b n-$C_nH_{2n+1}$—⬡—⬡—n-$C_mH_{2m+1}$

III-1c n-$C_nH_{2n+1}$—⬡—⬡—$(CH_2)_o$—CH=$CH_2$

III-1d $CH_2$=CH—$(CH_2)_o$—⬡—⬡—$(CH_2)_p$—CH=$CH_2$ in which n and m are each, independently of one another, from 1 to 5, and o and p are each, independently both thereof and of one another, from 0 to 3,

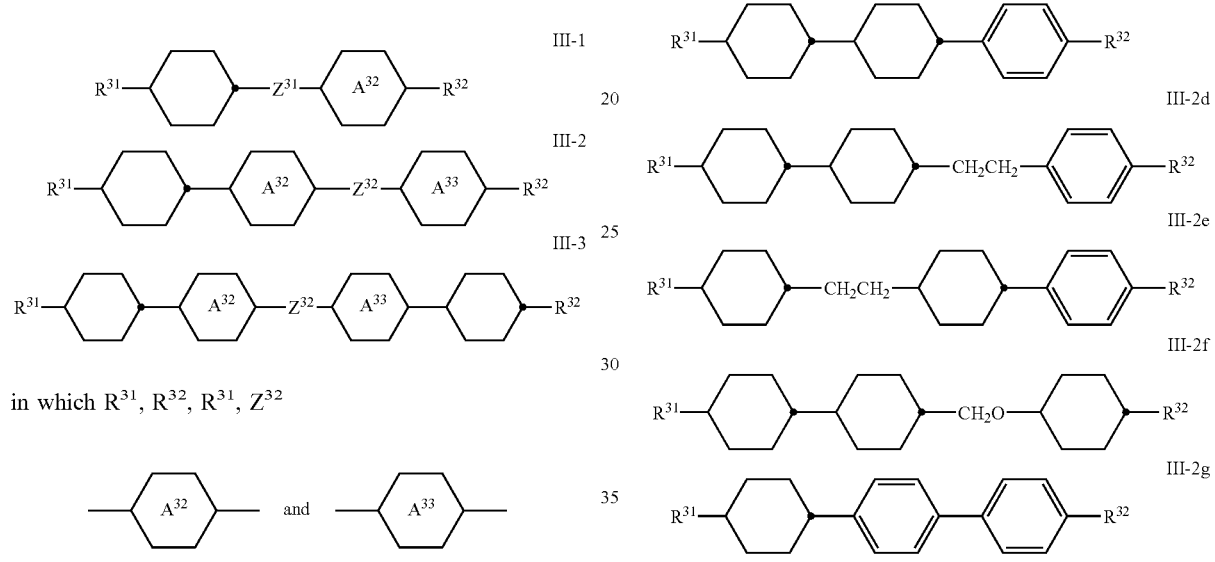

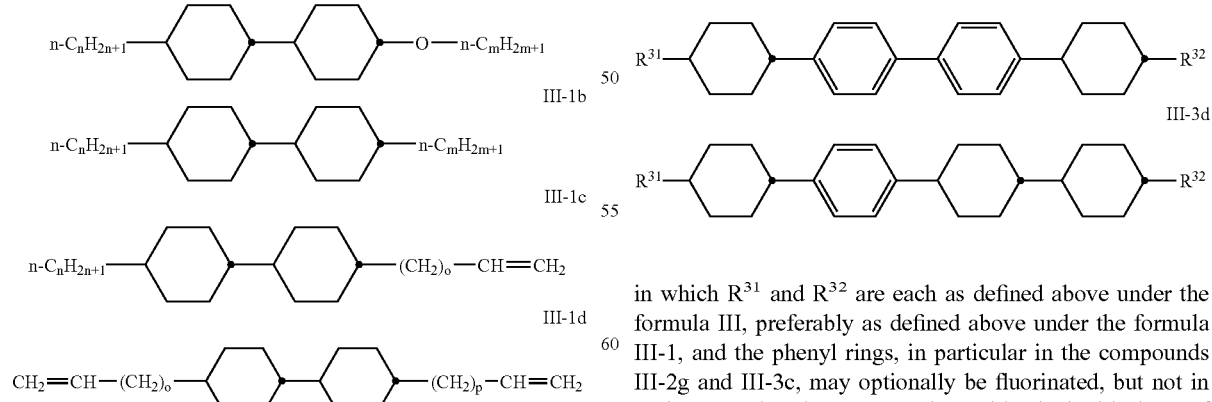

in which $R^{31}$ and $R^{32}$ are each as defined above under the formula III, preferably as defined above under the formula III-1, and the phenyl rings, in particular in the compounds III-2g and III-3c, may optionally be fluorinated, but not in such a way that the compounds are identical with those of the formula II and its sub-formulae. $R^{31}$ is preferably n-alkyl having from 1 to 5 carbon atoms, particularly preferably having from 1 to 3 carbon atoms, and $R^{32}$ is preferably n-alkyl or n-alkoxy having from 1 to 5 carbon atoms or alkenyl having from 2 to 5 carbon atoms. Of these, especial preference is given to compounds of the formulae III-1a to III-1d.

Preferred fluorinated compounds of the formulae III-2g and III-3c are the compounds of the formulae III-2g' and III-3c'

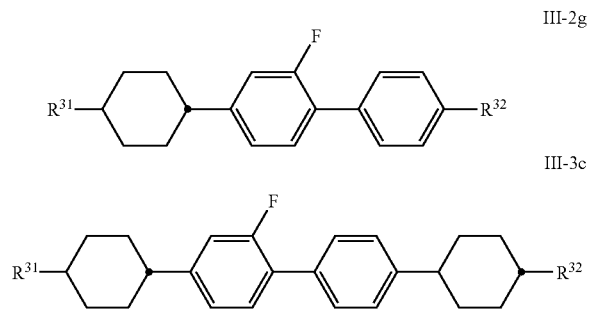

in which $R^{31}$ and $R^{32}$ are each as defined above under the formula III, preferably as defined above under the formula III-2g or III-3c.

In the present application, unless expressly stated otherwise, the term compounds is taken to mean both one compound and a plurality of compounds.

The liquid-crystal media according to the invention preferably have nematic phases of in each case from at least −20° C. to 80° C., preferably from −30° C. to 85° C. and very particularly preferably from −40° C. to 100° C. The term "have a nematic phase" here is taken to mean firstly that no smectic phase and no crystallisation are observed at low temperatures at the corresponding temperature and secondly also that no clearing occurs on heating from the nematic phase. The investigation at low temperatures is carried out in a flow viscometer at the corresponding temperature and checked by storage in test cells having a layer thickness corresponding to the electro-optical application for at least 100 hours. The storage stability ($t_{store}$ (T)) at the corresponding temperature (T) is quoted as the time up to which all three test cells show no change. At high temperatures, the clearing point is measured in capillaries by conventional methods.

Furthermore, the liquid-crystal media according to the invention are characterised by low optical anisotropy values.

The term "alkyl" preferably covers straight-chain and branched alkyl groups having from 1 to 7 carbon atoms, in particular the straight-chain groups methyl, ethyl, propyl, butyl, pentyl, hexyl and heptyl. Groups having from 2 to 5 carbon atoms are generally preferred.

The term "alkenyl" preferably covers straight-chain and branched alkenyl groups having from 2 to 7 carbon atoms, in particular the straight-chain groups. Particularly preferred alkenyl groups are $C_2$- to $C_7$-1 E-alkenyl, $C_4$- to $C_7$-3E-alkenyl, $C_5$- to $C_7$-4-alkenyl, $C_6$- to $C_7$-5-alkenyl and $C_7$-6-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups having a terminal fluorine, i.e. fluoromethyl, 2-fluoroethyl, 3-fluoropropyl, 4-fluoro-butyl, 5-fluoropentyl, 6-fluorohexyl and 7-fluoroheptyl. However, other positions of the fluorine are not excluded.

The term "oxaalkyl" or "alkoxyalkyl" preferably covers straight-chain radicals of the formula $C_nH_{2n+1}$—O—$(CH_2)_m$, in which n and m are each, independently of one another, from 1 to 6. n is preferably 1 and m is preferably from 1 to 6.

Compounds containing a vinyl end group and compounds containing a methyl end group have low rotational viscosity.

In the present application, the term dielectrically positive compounds means compounds having a $\Delta\epsilon$ of >1.5, dielectrically neutral compounds means those in which $-1.5 \leq \Delta\epsilon \leq 1.5$, and dielectrically negative compounds means those having a $\Delta\epsilon$ of <−1.5. The dielectric anisotropy of the compounds is determined here by dissolving 10% of the compounds in a liquid-crystalline host and determining the capacitance of this mixture at 1 kHz in at least one test cell with a layer thickness of about 20 μm having a homeotropic surface alignment and at least one test cell with a layer thickness of about 20 μm having a homogeneous surface alignment. The measurement -voltage is typically from 0.5 V to 1.0 V, but is always less than the capacitive threshold of the respective liquid-crystal mixture.

The host mixture used for determining the applicationally relevant physical parameters is ZLI-4792 from Merck KGaA, Germany. As an exception, the determination of the dielectric anisotropy of dielectrically negative compounds is carried out using ZLI-2857, likewise from Merck KGaA, Germany. The values for the respective compound to be investigated are obtained from the change in the properties, for example the dielectric constants, of the host mixture after addition of the compound to be investigated and extrapolation to 100% of the compound employed.

The concentration employed for the compound to be investigated is 10%. If the solubility of the compound to be investigated is inadequate for this purpose, the concentration employed is, by way of exception, halved, i.e. reduced to 5%, 2.5%, etc., until the concentration is below the solubility limit.

The term threshold voltage usually relates to the optical threshold for 10% relative contrast ($V_{10}$). In relation to the liquid-crystal mixtures of negative .dielectric anisotropy, however, the term threshold voltage is used in the present application for the capacitive threshold voltage ($V_0$), also known as the Freedericksz threshold, unless explicitly stated otherwise.

All concentrations in this application, unless explicitly stated otherwise, are given in percent by weight and relate to the corresponding mixture as a whole. All physical properties are and have been determined in accordance with "Merck Liquid Crystals, Physical Properties of Liquid Crystals", status November 1997, Merck KGaA, Germany, and apply to a temperature of 20° C., unless explicitly stated otherwise. An is determined at 589 nm and $\Delta\epsilon$ at 1 kHz.

In the case of the liquid-crystal media of negative dielectric anisotropy, the threshold voltage was determined as the capacitive threshold $V_0$ in cells with a liquid-crystal layer aligned homeotropically by means of lecithin.

The liquid-crystal media according to the invention may, if necessary, also comprise further additives and optionally also chiral dopants in the conventional amounts. The amount of these additives employed is in total from 0% to 10%, based on the amount of the mixture as a whole, preferably from 0.1% to 6%. The concentrations of the individual compounds employed are in each case preferably from 0.1 to 3%. The concentration of these and similar additives is not taken into account when indicating the concentrations and the concentration ranges of the liquid-crystal compounds in the liquid-crystal media.

The compositions consist of a plurality of compounds, preferably from 3 to 30, particularly preferably from 6 to 20 and very particularly preferably from 10 to 16 compounds, which are mixed in a conventional manner. In general, the desired amount of the components used in lesser amount is dissolved in the components making up the principal constituent, advantageously at elevated temperature. If the selected temperature is above the clearing point of the principal constituent, the completion of the dissolution process is particularly easy to observe. However, it is also possible to prepare the liquid-crystal mixtures in other conventional ways, for example using premixes or from a so-called "multibottle" system.

By means of suitable additives, the liquid-crystal phases according to the invention can be modified in such a way that they can be employed in any type of display and in particular of ECB display and IPS display that has been disclosed hitherto.

The examples below serve to illustrate the invention without representing a restriction. In the examples, the melting point T(C,N), the transition from the smectic (S) phase to the nematic (N) phase T(S,N) and the clearing point T(N,I) of a liquid-crystal substance are indicated in degrees Celsius. The various smectic phases are characterised by corresponding suffixes.

The percentages above and below are, unless explicitly stated otherwise, percent by weight, and the physical properties are the values at 20° C., unless explicitly stated otherwise.

All the temperature values indicated in this application are ° C. and all temperature differences are correspondingly differential degrees, unless explicitly stated otherwise.

In the synthesis examples and schemes, the abbreviations have the following meanings:

| | |
|---|---|
| BuLi | n-butyllithium, |
| DAST | diethylaminosulfur trifluoride, |
| DCC | dicyclohexylcarbodiimide, |
| DMAP | dimethylaminopyridine, |
| DMF | N,N-dimethylformamide, |
| dppf | 1,1'-bis(diphenylphosphino)ferrocene, |
| dppp | 1,3-bis(diphenylphosphino)propane, |
| LDA | lithium diisopropylamide, |
| MBT | MBT ether, methyl tert-butyl ether and |
| THF | tetrahydrofuran. |

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively. The coding in Table B is self-evident. In Table A, only the acronym for the parent structure is indicated. In individual cases, the acronym for the parent structure is followed, separated by a hyphen, by a code for the substituents $R^1$, $R^2$, $L^1$, $L^2$ and $L^3$:

| Code for $R^1$, $R^2$, $L^1$, $L^2$, $L^3$ | $R^1$ | $R^2$ | $L^1$ | $L^2$ | $L^3$ |
|---|---|---|---|---|---|
| nm | $C_nH_{2n+1}$ | $C_mH_{2m+1}$ | H | H | H |
| nOm | $C_nH_{2n+1}$ | $OC_mH_{2m+1}$ | H | H | H |
| nO•m | $OC_nH_{2n+1}$ | $C_mH_{2m+1}$ | H | H | H |
| nmFF | $C_nH_{2n+1}$ | $C_mH_{2m+1}$ | F | H | F |
| nOmFF | $C_nH_{2n+1}$ | $OC_mH_{2m+1}$ | F | H | F |
| nO•mFF | $OC_nH_{2n+1}$ | $C_mH_{2m+1}$ | F | H | F |
| nO•OmFF | $OC_nH_{2n+1}$ | $OC_mH_{2m+1}$ | F | H | F |
| n | $C_nH_{2n+1}$ | CN | H | H | H |
| nN•F | $C_nH_{2n+1}$ | CN | F | H | H |
| nN•F•F | $C_nH_{2n+1}$ | CN | F | F | H |
| nF | $C_nH_{2n+1}$ | F | H | H | H |
| nF•F | $C_nH_{2n+1}$ | F | F | H | H |
| nF•F•F | $C_nH_{2n+1}$ | F | F | F | H |
| nCl | $C_nH_{2n+1}$ | Cl | H | H | H |
| nCl•F | $C_nH_{2n+1}$ | Cl | F | H | H |
| nCl•F•F | $C_nH_{2n+1}$ | Cl | F | F | H |
| nmF | $C_nH_{2n+1}$ | $C_mH_{2m+1}$ | F | H | H |
| nCF$_3$ | $C_nH_{2n+1}$ | CF$_3$ | H | H | H |
| nOCF$_3$ | $C_nH_{2n+1}$ | OCF$_3$ | H | H | H |
| nOCF$_3$•F | $C_nH_{2n+1}$ | OCF$_3$ | F | H | H |
| nOCF$_3$•F•F | $C_nH_{2n+1}$ | OCF$_3$ | F | F | H |
| nOCF$_2$ | $C_nH_{2n+1}$ | OCHF$_2$ | H | H | H |
| nOCF$_2$•F•F | $C_nH_{2n+1}$ | OCHF$_2$ | F | F | H |
| nS | $C_nH_{2n+1}$ | NCS | H | H | H |
| rVsN | $C_rH_{2r+1}$—CH=CH—$C_sH_{2s}$— | CN | H | H | H |
| nEsN | $C_rH_{2r+1}$—O—$C_sH_{2s}$— | CN | H | H | H |
| nAm | $C_nH_{2n+1}$ | COO$C_mH_{2m+1}$ | H | H | H |
| nF•Cl | $C_nH_{2n+1}$ | F | Cl | H | H |

TABLE A
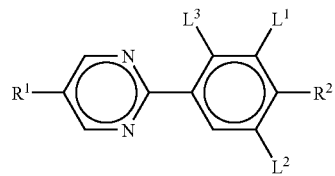
PYP
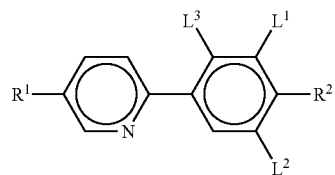
PYRP
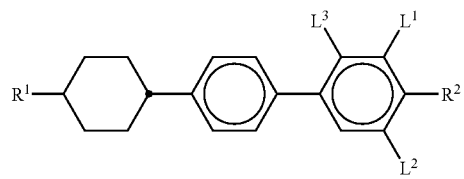
BCH
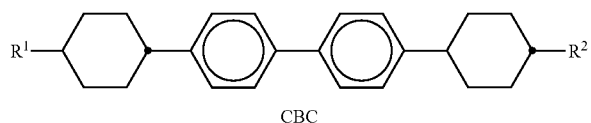
CBC
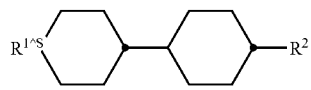
CCH
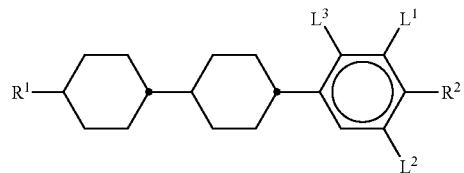
CCP
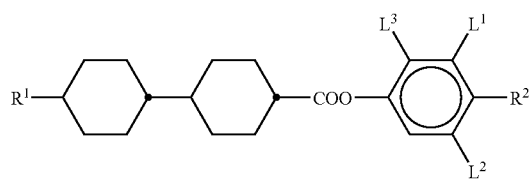
CP TABLE A-continued
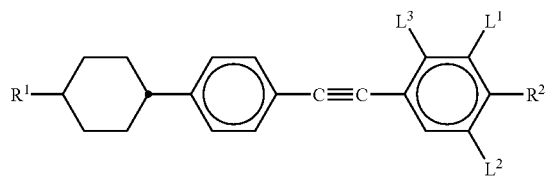
CPTP
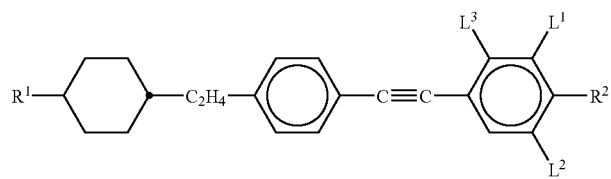
CEPTP
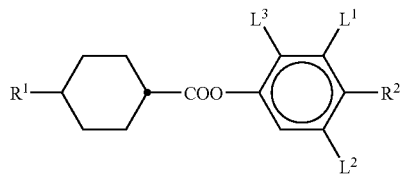
D
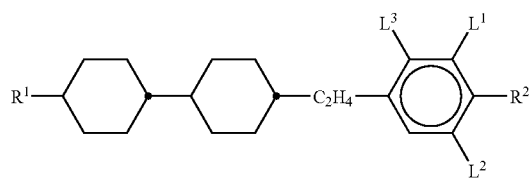
ECCP
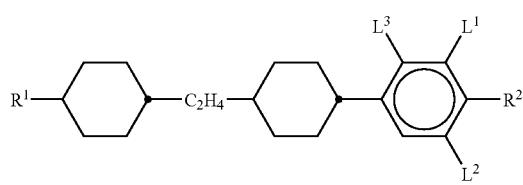
CECP
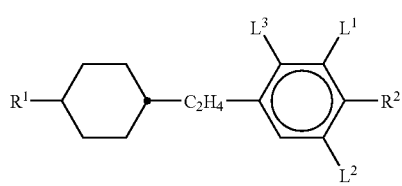
EPCH
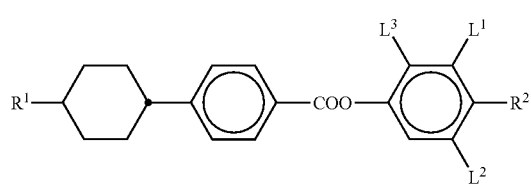
HP TABLE A-continued
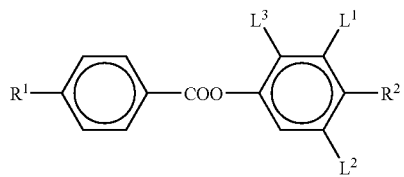
ME
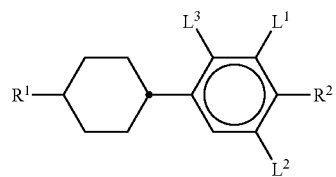
PCH
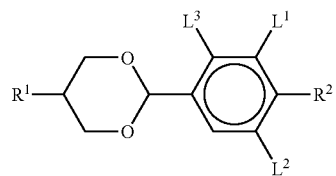
PDX
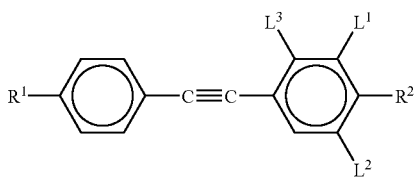
PTP
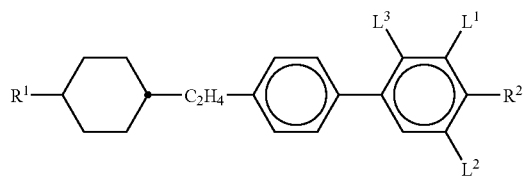
BECH
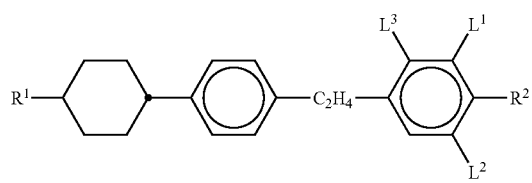
EBCH
CPC TABLE A-continued
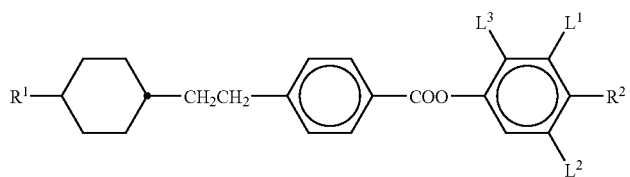
EHP
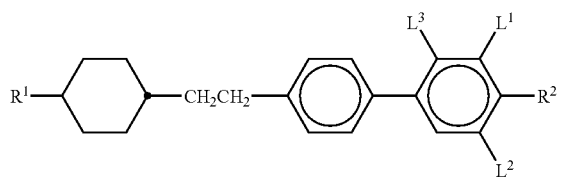
BEP
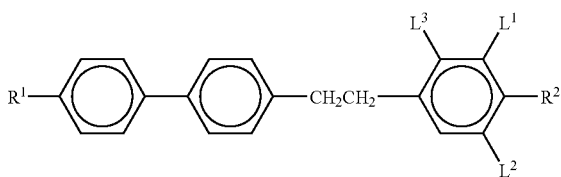
ET
TABLE B
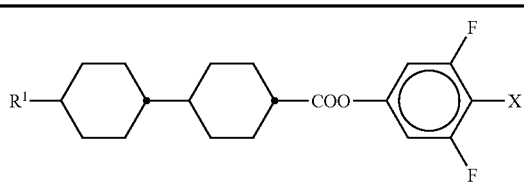
CCZU-n-X
(X = F, Cl, —OCF₃ = "OT")
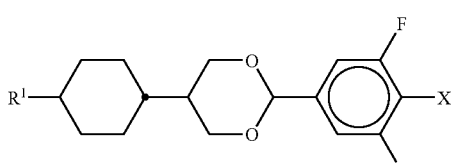
CDU-n-X
(X = F, Cl, —OCF₃ = "OT")
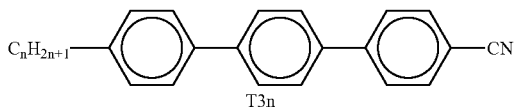
T3n
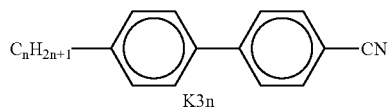
K3n
M3n TABLE B-continued
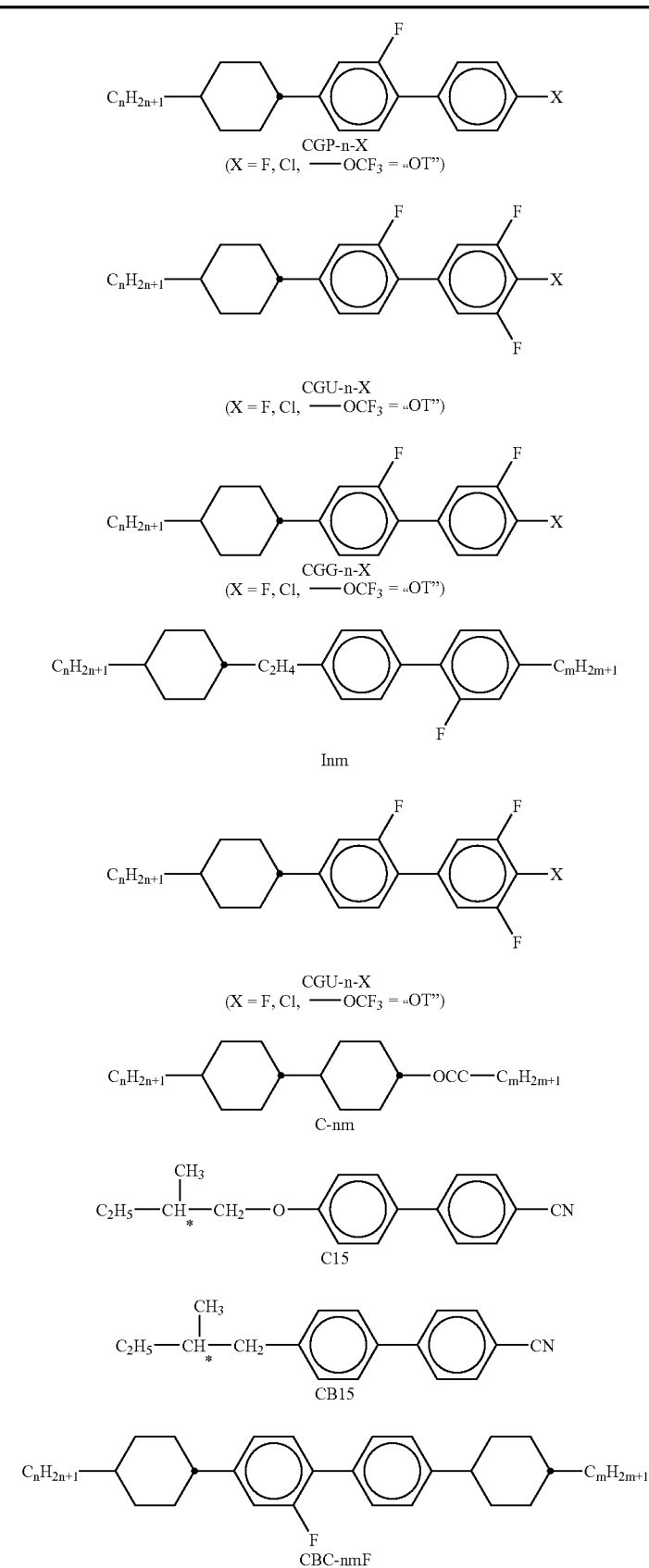

TABLE B-continued
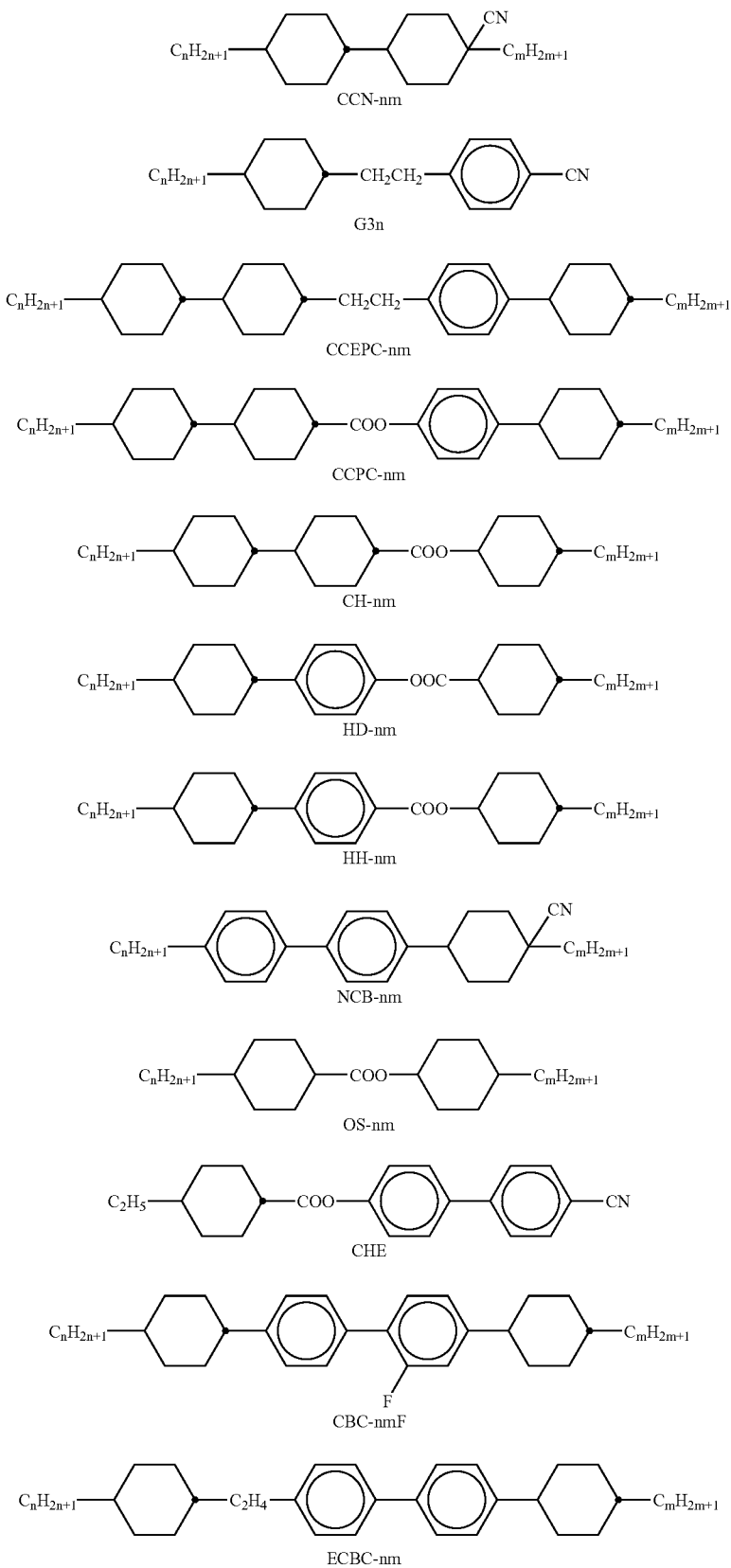

TABLE B-continued
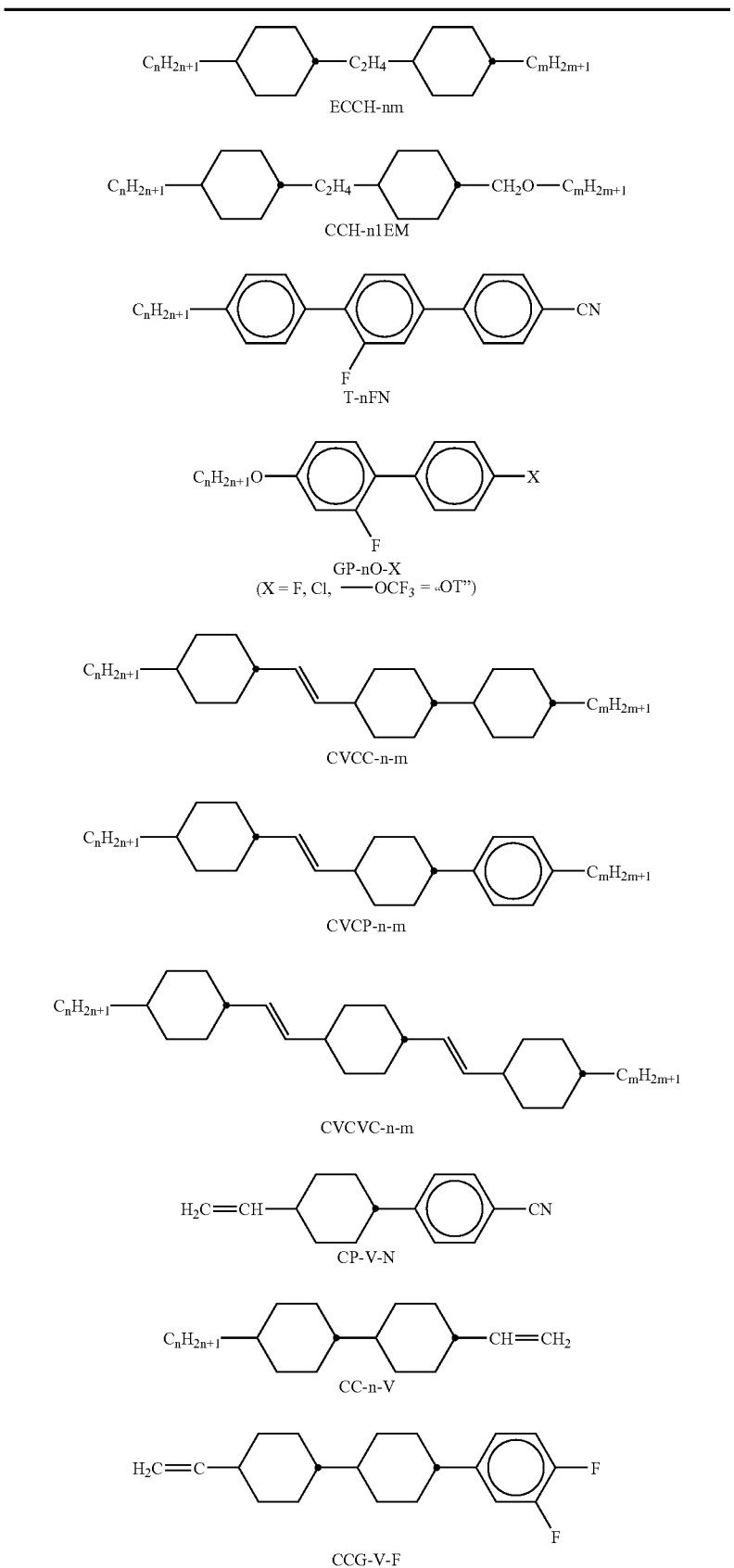

TABLE B-continued
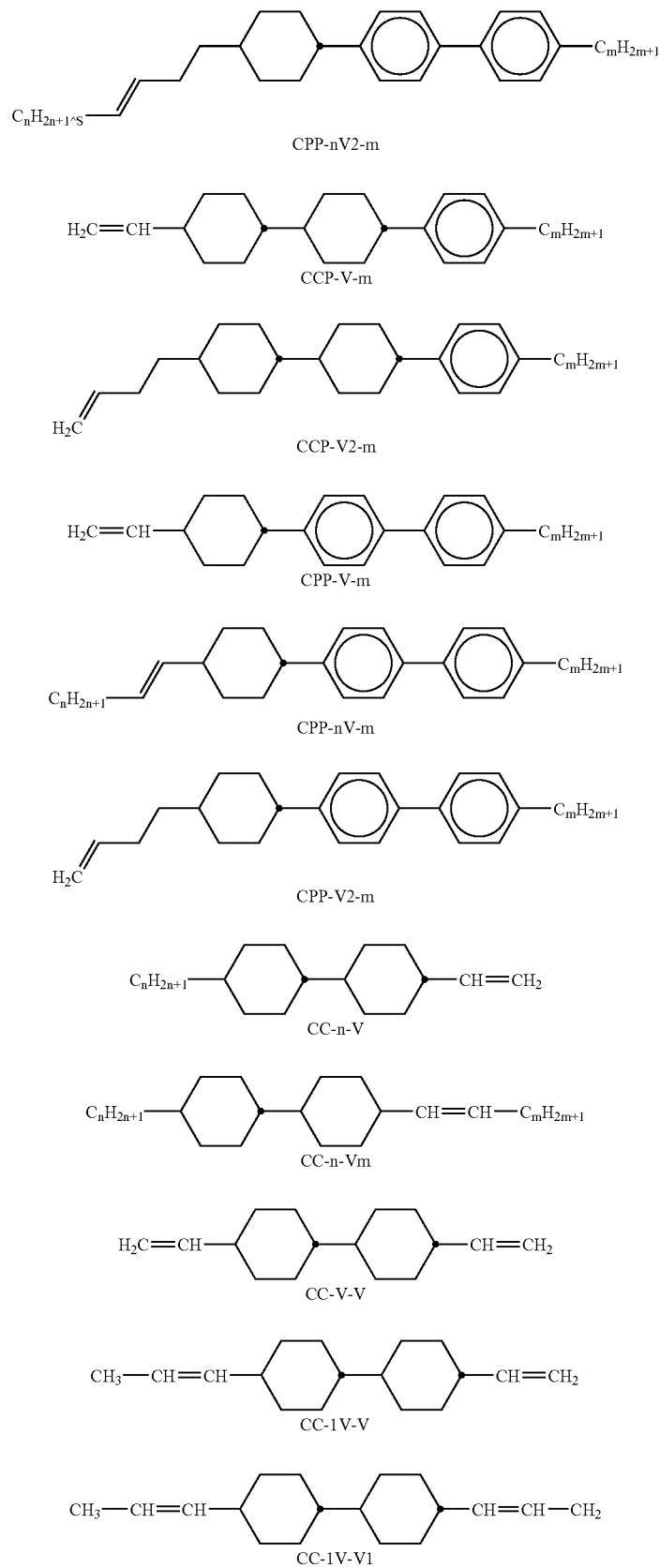

TABLE B-continued
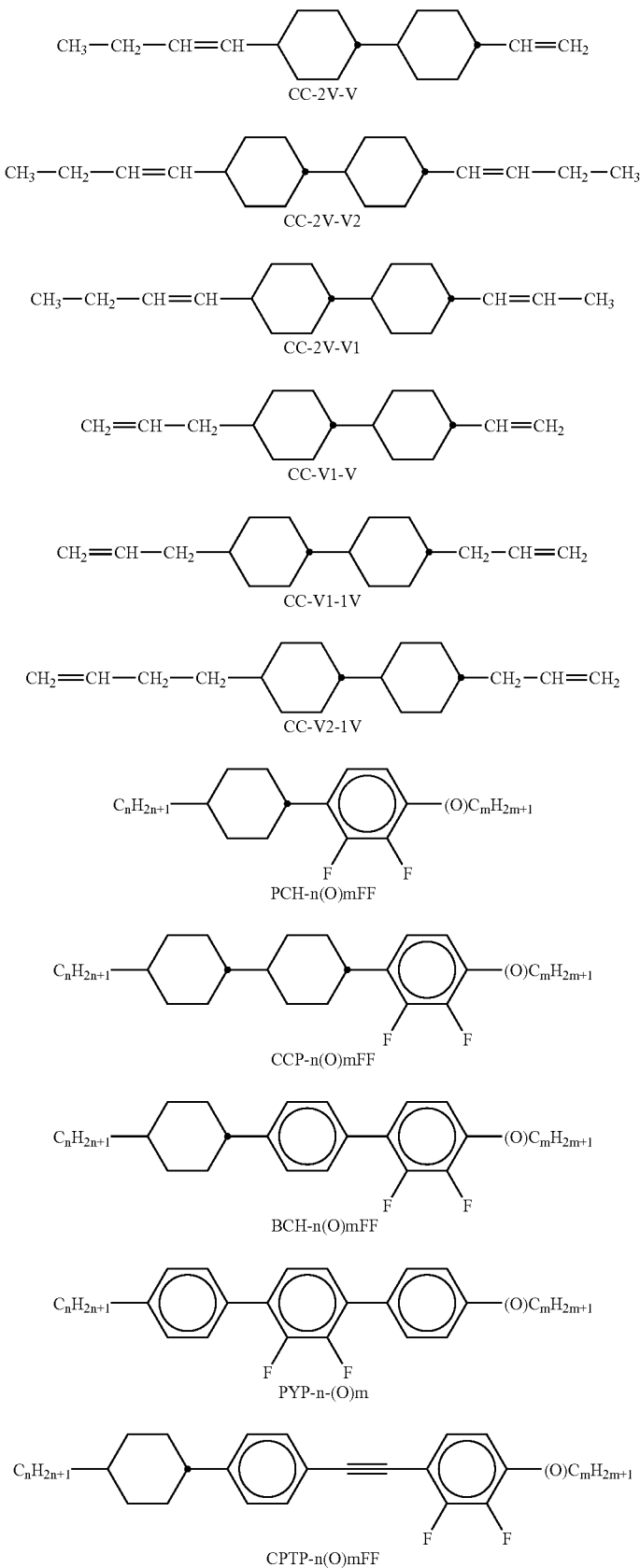

TABLE B-continued
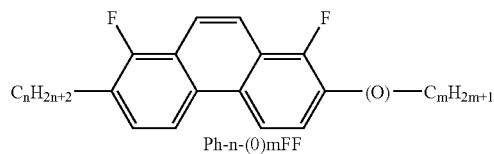
Ph-n-(O)mFF
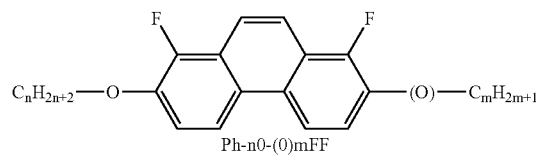
Ph-nO-(O)mFF
BHHO-n-(O)mFF
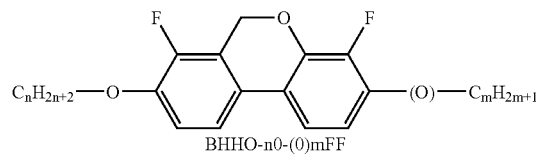
BHHO-nO-(O)mFF
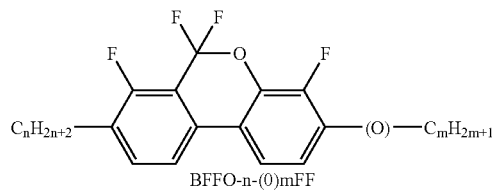
BFFO-n-(O)mFF
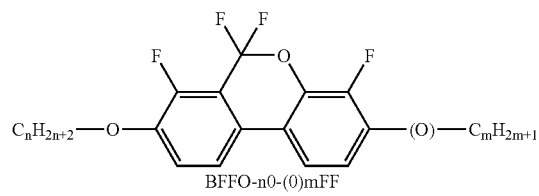
BFFO-nO-(O)mFF
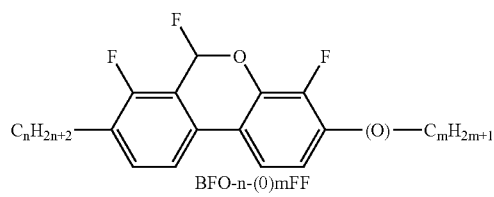
BFO-n-(O)mFF
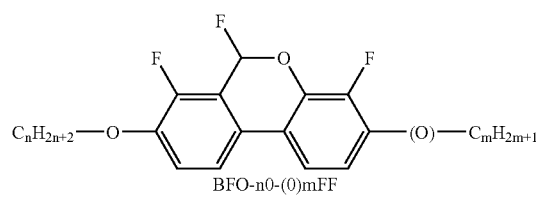
BFO-nO-(O)mFF TABLE B-continued
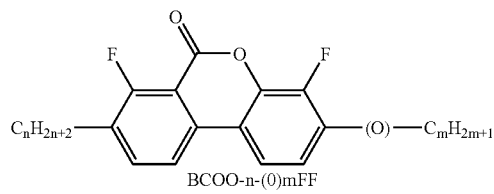
BCOO-n-(O)mFF
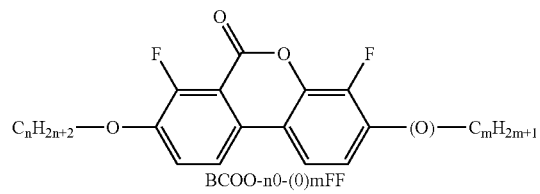
BCOO-nO-(O)mFF
BHHO-O1P-n(O)-HFF
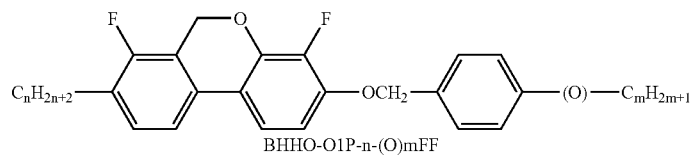
BHHO-O1P-n-(O)mFF
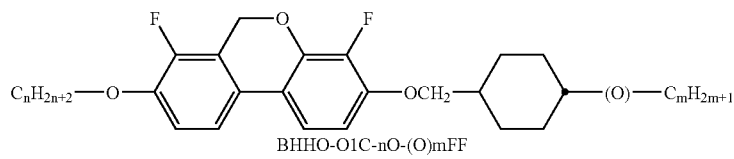
BHHO-O1C-nO-(O)mFF
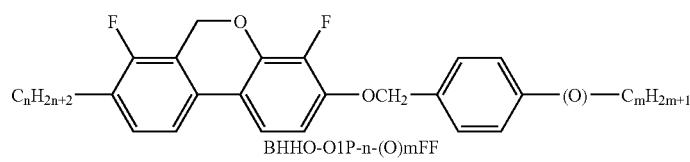
BHHO-O1P-n-(O)mFF
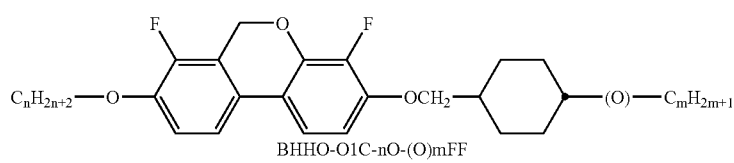
BHHO-O1C-nO-(O)mFF
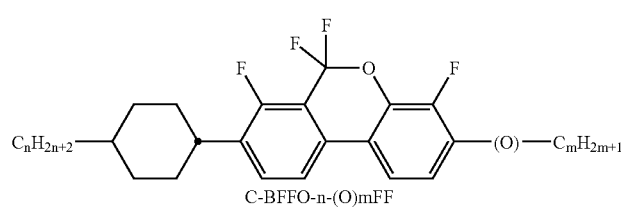
C-BFFO-n-(O)mFF TABLE B-continued

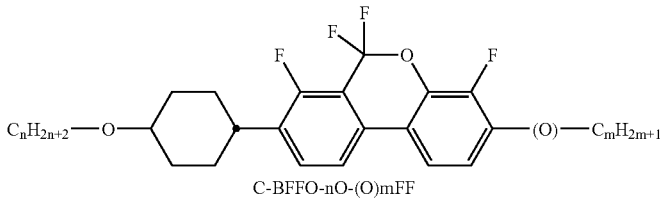

C-BFFO-nO-(O)mFF

EXAMPLES

The following examples are intended to explain the invention without limiting it. Above and below, percentages are percent by weight. All temperatures are indicated in degrees Celsius. An denotes the optical anisotropy (589 nm, 20° C.), Δε the dielectric anisotropy (1 kHz, 20° C.), H.R. the voltage holding ratio (at 100° C., after 5 minutes in the oven, 1 V). $V_{10}$, $V_{50}$ and $V_{90}$ (the threshold voltage, midgrey voltage and saturation voltage respectively) and $V_0$ (the capacitive threshold voltage) were each determined at 20° C.

Substance Examples

Example 1

(4,7-Difluoro-8-methyl-3-pentyl-6H-benzo[c]chromen-6-one)

1.1 Preparation of 4-bromo-2-fluoro-1-pentylbenzene

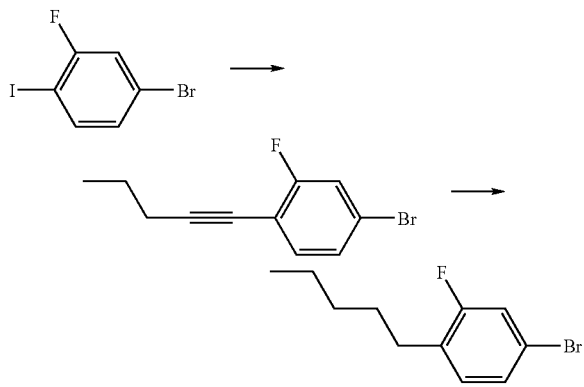

190 g (0.600 mol) of 4-bromo-2-fluoro-1-iodobenzene and 65.3 ml of 1-pentyne were dissolved in a mixture of 900 ml of THF and 1.2 l of triethylamine and cooled to 10° C., and 1.14 g (6 mmol) of copper(I) iodide and 8.42 g (12 mmol) of bis(triphenylphosphine)palladium(II) chloride were added. The batch was stirred overnight at room temperature, water and MTB ether were subsequently added, and the mixture was stirred for a further 5 minutes. The reaction mixture was filtered through Celite® with suction, and the phases were separated. The aqueous phase was extracted twice with MTB ether, and the combined organic phases were washed three times with water, dried over sodium sulfate and evaporated under reduced pressure. The crude product was filtered through silica gel with n-heptane, giving 129 g of 4-bromo-2-fluoro-1-pent-1-ynylbenzene as a yellow liquid. Hydrogenation on palladium/activated carbon (10%) in THF gave 131 g (100%) of 4-bromo-2-fluoro-1-pentylbenzene as a yellow liquid.

1.2 Preparation of 6-bromo-2-fluoro-3-pentylphenol

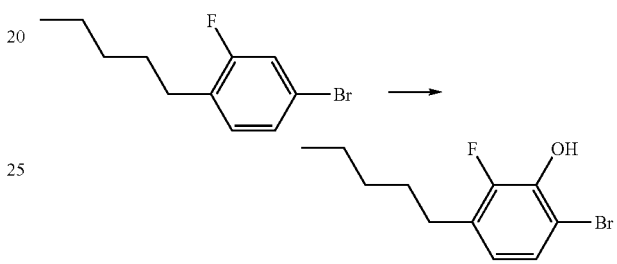

132 g (0.583 mol) of 4-bromo-2-fluoro-1-pentylbenzene were dissolved in 900 ml of THF, and 295 ml of a 2 molar solution of LDA in THF were added dropwise at −70° C. After 1 hour, 65.9 ml (0.590 mol) of trimethyl borate were added, and the mixture was stirred for a further 1 hour and then acidified at −15° C. using 150 ml of 50 percent acetic acid. The batch was subsequently warmed to 30° C., and 139 ml (1.61 mol) of 35 percent hydrogen peroxide solution were added dropwise. After 1 hour, the mixture was diluted with water, and the organic phase was separated off. The combined organic phases were washed twice with ammonium iron(II) sulfate solution and once with water, dried over sodium sulfate and evaporated under reduced pressure.

Filtration of the crude product through silica gel with n-heptane/1-chlorobutane (3:1) gave 86.0 g (61% of theory) of 6-bromo-2-fluoro-3-pentylphenol as colourless crystals.

1.3 Preparation of 6-bromo-2-fluoro-3-methylbenzoic acid

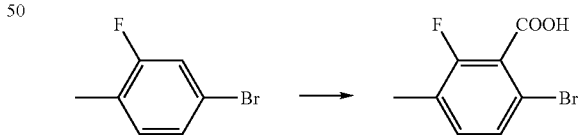

50 ml (0.385 mol) of 4-bromo-2-fluorotoluene were dissolved in 750 ml of THF, and 231 ml (0.462 mol) of a 2 M solution of LDA in THF were added dropwise at −70° C. After 70 minutes, 37.2 g (0.846 mol) of carbon dioxide were passed in, and the batch was allowed to thaw. After acidification using conc. hydrochloric acid, the solution was extracted with MTB ether, and the combined organic phases were washed with water, dried over sodium sulfate and evaporated under reduced pressure. Crystallisation of the crude product from 1-chlorobutane gave 44.1 g (49%) of 6-bromo-2-fluoro-3-methylbenzoic acid as white crystals.

1.4 Preparation of 6-bromo-2-fluoro-3-pentylphenyl 6-bromo-2-fluoro-3-methylbenzoate

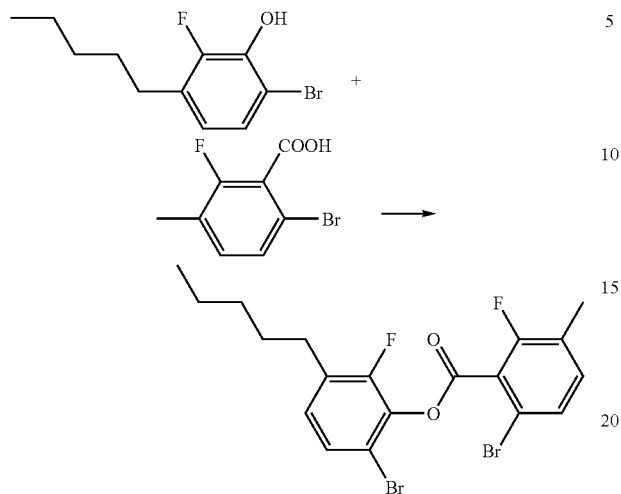

43.2 g (0.165 mol) of 6-bromo-2-fluoro-3-pentylphenol, 40.5 g (0.173 mol) of 6-bromo-2-fluoro-3-methylbenzoic acid and 3.52 g (29 mmol) of 4-(dimethylamino)pyridine were initially introduced in 300 ml of dichloro-methane, and a solution of 35.7 g (0.172 mol) of N,N-dicyclohexylcarbodiimide in 80 ml of dichloromethane was added. The batch was stirred overnight at room temperature, and 4.16 g (33 mmol) of oxalic acid were subsequently added. After 1 hour, the precipitated solid was filtered off, and the filtrate was evaporated under reduced pressure. The crude product was filtered through silica gel with n-heptane/1-chlorobutane (1:1), giving 72.7 g (91% of theory) of 6-bromo-2-fluoro-3-pentylphenyl 6-bromo-2-fluoro-3-methylbenzoate as a colourless oil.

1.5 Preparation of 4,7-difluoro-8-methyl-3-pentyl-6H-benzo[c]chromen-6-one

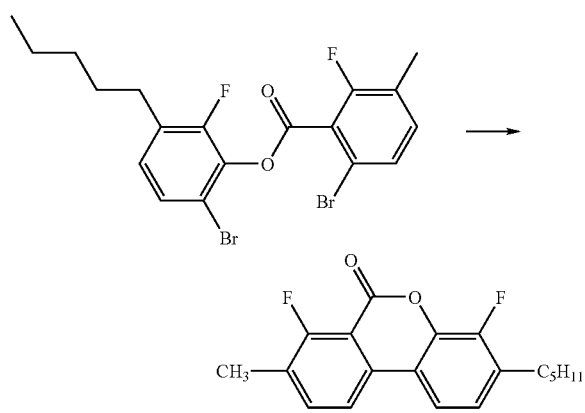

56.2 g (118 mmol) of 6-bromo-2-fluoro-3-pentylphenyl 6-bromo-2-fluoro-3-methylbenzoate were dissolved in 650 ml of DMF, and the mixture was refluxed for 48 hours in the presence of 75.1 g (1.18 mmol) of copper powder. The mixture was subsequently diluted with water and extracted with ethyl acetate. The extracts were combined, dried over $Na_2SO_4$ and evaporated. The crude product was recrystallised from 1-chlorobutane, giving 9.60 g of the lactone as a colourless solid. This corresponds to a yield of 26%.

The physical properties of the compound are shown in the following table.

Examples 2 to 120

The following are prepared analogously to Example 1:

| No. | $R^1$ | $R^2$ | Phase sequence T/° C. | $\Delta\epsilon^*$ | $T^*(N,I)/$ ° C. |
|---|---|---|---|---|---|
| 2 | $CH_3$ | $CH_3$ | C 237 I | | |
| 3 | $CH_3$ | $C_2H_5$ | | | |
| 4 | $CH_3$ | $n-C_3H_7$ | | | |
| 5 | $CH_3$ | $n-C_4H_9$ | | | |
| 1 | $CH_3$ | $n-C_5H_{11}$ | C 104 I | −17.8 | 22 |
| 6 | $CH_3$ | $n-C_6H_{13}$ | | | |
| 7 | $CH_3$ | $n-C_7H_{15}$ | | | |
| 8 | $CH_3$ | $CH_3O$ | | | |
| 9 | $CH_3$ | $C_2H_5O$ | | | |
| 10 | $CH_3$ | $n-C_3H_7O$ | | | |
| 11 | $CH_3$ | $n-C_4H_9O$ | | | |
| 12 | $CH_3$ | $CH_2=CH$ | | | |
| 13 | $CH_3$ | $E-CH_3-CH=CH$ | | | |
| 14 | $CH_3$ | $CH_2=CH-O$ | | | |
| 15 | $CH_3$ | $CH_2=CH-CH_2O$ | | | |
| 16 | $C_2H_5$ | $CH_3$ | | | |
| 17 | $C_2H_5$ | $C_2H_5$ | | | |
| 18 | $C_2H_5$ | $n-C_3H_7$ | | | |
| 19 | $C_2H_5$ | $n-C_4H_9$ | | | |
| 20 | $C_2H_5$ | $n-C_5H_{11}$ | | | |
| 21 | $C_2H_5$ | $n-C_6H_{13}$ | | | |
| 22 | $C_2H_5$ | $n-C_7H_{15}$ | | | |
| 23 | $C_2H_5$ | $CH_3O$ | | | |
| 24 | $C_2H_5$ | $C_2H_5O$ | | | |
| 25 | $C_2H_5$ | $n-C_3H_7O$ | | | |
| 26 | $C_2H_5$ | $n-C_4H_9O$ | | | |
| 27 | $C_2H_5$ | $CH_2=CH$ | | | |
| 28 | $C_2H_5$ | $E-CH_3-CH=CH$ | | | |
| 29 | $C_2H_5$ | $CH_2=CH-O$ | | | |
| 30 | $C_2H_5$ | $CH_2=CH-CH_2O$ | | | |
| 31 | $n-C_3H_7$ | $CH_3$ | | | |
| 32 | $n-C_3H_7$ | $C_2H_5$ | | | |
| 33 | $n-C_3H_7$ | $n-C_3H_7$ | | | |
| 34 | $n-C_3H_7$ | $n-C_4H_9$ | | | |
| 35 | $n-C_3H_7$ | $n-C_5H_{11}$ | C 103 I | −19.0 | 7 |
| 36 | $n-C_3H_7$ | $n-C_6H_{13}$ | | | |
| 37 | $n-C_3H_7$ | $n-C_7H_{15}$ | | | |
| 38 | $n-C_3H_7$ | $CH_3O$ | | | |
| 39 | $n-C_3H_7$ | $C_2H_5O$ | | | |
| 40 | $n-C_3H_7$ | $n-C_3H_7O$ | | | |
| 41 | $n-C_3H_7$ | $n-C_4H_9O$ | | | |
| 42 | $n-C_3H_7$ | $CH_2=CH$ | | | |
| 43 | $n-C_3H_7$ | $E-CH_3-CH=CH$ | | | |
| 44 | $n-C_3H_7$ | $CH_2=CH-O$ | | | |
| 45 | $n-C_3H_7$ | $CH_2=CH-CH_2O$ | | | |
| 46 | $n-C_4H_9$ | $CH_3$ | | | |
| 47 | $n-C_4H_9$ | $C_2H_5$ | | | |
| 48 | $n-C_4H_9$ | $n-C_3H_7$ | | | |
| 49 | $n-C_4H_9$ | $n-C_4H_9$ | | | |
| 50 | $n-C_4H_9$ | $n-C_5H_{11}$ | | | |
| 51 | $n-C_4H_9$ | $n-C_6H_{13}$ | | | |
| 52 | $n-C_4H_9$ | $n-C_7H_{15}$ | | | |
| 53 | $n-C_4H_9$ | $CH_3O$ | | | |
| 54 | $n-C_4H_9$ | $C_2H_5O$ | | | |
| 55 | $n-C_4H_9$ | $n-C_3H_7O$ | | | |
| 56 | $n-C_4H_9$ | $n-C_4H_9O$ | | | |

-continued

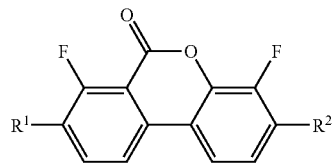

| No. | R¹ | R² | Phase sequence T/° C. | Δε* | T*(N,I)/ ° C. |
|---|---|---|---|---|---|
| 57 | n-C₄H₉ | CH₂=CH | | | |
| 58 | n-C₄H₉ | E-CH₃—CH=CH | | | |
| 59 | n-C₄H₉ | CH₂=CH—O | | | |
| 60a | n-C₄H₉ | CH₂=CH—CH₂O | | | |
| 60b | n-C₅H₁₁ | n-C₄H₉O | C 130 I | −23.5 | 57 |
| 61 | CH₃O | CH₃ | | | |
| 62 | CH₃O | C₂H₅ | | | |
| 63 | CH₃O | n-C₃H₇ | | | |
| 64 | CH₃O | n-C₄H₉ | | | |
| 65 | CH₃O | n-C₅H₁₁ | | | |
| 66 | CH₃O | n-C₆H₁₃ | | | |
| 67 | CH₃O | n-C₇H₁₅ | | | |
| 68 | CH₃O | CH₃O | | | |
| 69 | CH₃O | C₂H₅O | | | |
| 70 | CH₃O | n-C₃H₇O | | | |
| 71 | CH₃O | n-C₄H₉O | | | |
| 72 | CH₃O | CH₂=CH | | | |
| 73 | CH₃O | E-CH₃—CH=CH | | | |
| 74 | CH₃O | CH₂=CH—O | | | |
| 75 | CH₃O | CH₂=CH—CH₂O | | | |
| 76 | C₂H₅O | CH₃ | | | |
| 77 | C₂H₅O | C₂H₅ | | | |
| 78 | C₂H₅O | n-C₃H₇ | | | |
| 79 | C₂H₅O | n-C₄H₉ | | | |
| 80 | C₂H₅O | n-C₅H₁₁ | C 137 I | | |
| 81 | C₂H₅O | n-C₆H₁₃ | | | |
| 82 | C₂H₅O | n-C₇H₁₅ | | | |
| 83 | C₂H₅O | CH₃O | | | |
| 84 | C₂H₅O | C₂H₅O | | | |
| 85 | C₂H₅O | n-C₃H₇O | | | |
| 86 | C₂H₅O | n-C₄H₉O | | | |
| 87 | C₂H₅O | CH₂=CH | | | |
| 88 | C₂H₅O | E-CH₃—CH=CH | | | |
| 89 | C₂H₅O | CH₂=CH—O | | | |
| 90 | C₂H₅O | CH₂=CH—CH₂O | | | |
| 91 | CH₂=CH | CH₃ | | | |
| 92 | CH₂=CH | C₂H₅ | | | |
| 93 | CH₂=CH | n-C₃H₇ | | | |
| 94 | CH₂=CH | n-C₄H₉ | | | |
| 95 | CH₂=CH | n-C₅H₁₁ | | | |
| 96 | CH₂=CH | n-C₆H₁₃ | | | |
| 97 | CH₂=CH | n-C₇H₁₅ | | | |
| 98 | CH₂=CH | CH₃O | | | |
| 99 | CH₂=CH | C₂H₅O | | | |
| 100 | CH₂=CH | n-C₃H₇O | | | |
| 101 | CH₂=CH | n-C₄H₉O | | | |
| 102 | CH₂=CH | CH₂=CH | | | |
| 103 | CH₂=CH | E-CH₃—CH=CH | | | |
| 104 | CH₂=CH | CH₂=CH—O | | | |
| 105 | CH₂=CH | CH₂=CH—CH₂O | | | |
| 106 | CH₂=CH—O | CH₃ | | | |
| 107 | CH₂=CH—O | C₂H₅ | | | |
| 108 | CH₂=CH—O | n-C₃H₇ | | | |
| 109 | CH₂=CH—O | n-C₄H₉ | | | |
| 110 | CH₂=CH—O | n-C₅H₁₁ | | | |
| 111 | CH₂=CH—O | n-C₆H₁₃ | | | |
| 112 | CH₂=CH—O | n-C₇H₁₅ | | | |
| 113 | CH₂=CH—O | CH₃O | | | |
| 114 | CH₂=CH—O | C₂H₅O | | | |
| 115 | CH₂=CH—O | n-C₃H₇O | | | |
| 116 | CH₂=CH—O | n-C₄H₉O | | | |
| 117 | CH₂=CH—O | CH₂=CH | | | |
| 118 | CH₂=CH—O | E-CH₃—CH=CH | | | |
| 119 | CH₂=CH—O | CH₂=CH—O | | | |
| 120 | CH₂=CH—O | CH₂=CH—CH₂O | | | |

-continued

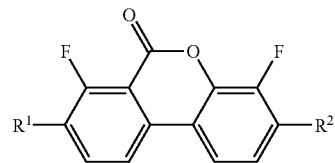

Note:
*values extrapolated from 10% solution in ZLI-4792 or ZLI-2857 (Δε).

Example 121

(4,7-Difluoro-8-methyl-3-pentyl-6H-benzo[c]chromene)

Preparation of 4,7-difluoro-8-methyl-3-pentyl-6H-benzo[c]chromene

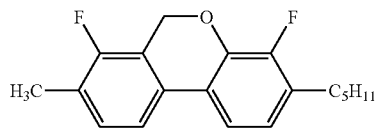

2.00 g (6.33 mmol) of the compound from Example 1 were dissolved in 12 ml of THF. 2.56 ml (23 mmol) of boron trifluoride/THF complex were added to this solution with ice-cooling. 12 ml of diethylene glycol dimethyl ether and, in portions, 0.58 g (15 mmol) of sodium borohydride were then added successively, and the mixture was stirred at room temperature (about 20° C.) for 16 hours. The reaction solution was hydrolysed using ice-water and extracted with MTB ether, and the extracts were combined and dried over Na₂SO₄ and evaporated. The crude product was recrystallised from n-heptane, giving 1.60 g of colourless crystals of the benzochromene. This corresponds to a yield of 83%.

Examples 122 to 240

The following are prepared analogously to Example 121:

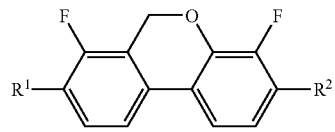

| No. | R¹ | R² | Phase sequence T/° C. | Δε* | T*(N,I)/ ° C. |
|---|---|---|---|---|---|
| 122 | CH₃ | CH₃ | C 110 I | −3.2 | 27 |
| 123 | CH₃ | C₂H₅ | | | |
| 124 | CH₃ | n-C₃H₇ | | | |
| 125 | CH₃ | n-C₄H₉ | | | |
| 121 | CH₃ | n-C₅H₁₁ | Tg −60 C 42 I | −3.1 | 6 |

-continued

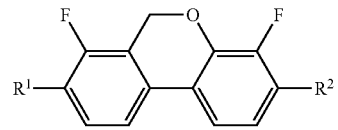

| No. | $R^1$ | $R^2$ | Phase sequence T/°C. | $\Delta\epsilon^*$ | $T^*(N,I)/$ °C. |
|---|---|---|---|---|---|
| 126 | $CH_3$ | $n\text{-}C_6H_{13}$ | | | |
| 127 | $CH_3$ | $n\text{-}C_7H_{15}$ | | | |
| 128 | $CH_3$ | $CH_3O$ | | | |
| 129 | $CH_3$ | $C_2H_5O$ | | | |
| 130 | $CH_3$ | $n\text{-}C_3H_7O$ | | | |
| 131 | $CH_3$ | $n\text{-}C_4H_9O$ | | | |
| 132 | $CH_3$ | $CH_2=CH$ | | | |
| 133 | $CH_3$ | $E\text{-}CH_3\text{-}CH=CH$ | | | |
| 134 | $CH_3$ | $CH_2=CH\text{-}O$ | | | |
| 135 | $CH_3$ | $CH_2=CH\text{-}CH_2O$ | | | |
| 136 | $C_2H_5$ | $CH_3$ | | | |
| 137 | $C_2H_5$ | $C_2H_5$ | | | |
| 138 | $C_2H_5$ | $n\text{-}C_3H_7$ | | | |
| 139 | $C_2H_5$ | $n\text{-}C_4H_9$ | | | |
| 140 | $C_2H_5$ | $n\text{-}C_5H_{11}$ | | | |
| 141 | $C_2H_5$ | $n\text{-}C_6H_{13}$ | | | |
| 142 | $C_2H_5$ | $n\text{-}C_7H_{15}$ | | | |
| 143 | $C_2H_5$ | $CH_3O$ | | | |
| 144 | $C_2H_5$ | $C_2H_5O$ | | | |
| 145 | $C_2H_5$ | $n\text{-}C_3H_7O$ | | | |
| 146 | $C_2H_5$ | $n\text{-}C_4H_9O$ | | | |
| 147 | $C_2H_5$ | $CH_2=CH$ | | | |
| 148 | $C_2H_5$ | $E\text{-}CH_3\text{-}CH=CH$ | | | |
| 149 | $C_2H_5$ | $CH_2=CH\text{-}O$ | | | |
| 150 | $C_2H_5$ | $CH_2=CH\text{-}CH_2O$ | | | |
| 151 | $n\text{-}C_3H_7$ | $CH_3$ | | | |
| 152 | $n\text{-}C_3H_7$ | $C_2H_5$ | | | |
| 153 | $n\text{-}C_3H_7$ | $n\text{-}C_3H_7$ | | | |
| 154 | $n\text{-}C_3H_7$ | $n\text{-}C_4H_9$ | | | |
| 155 | $n\text{-}C_3H_7$ | $n\text{-}C_5H_{11}$ | C 34 I | -2.7 | |
| 156 | $n\text{-}C_3H_7$ | $n\text{-}C_6H_{13}$ | | | |
| 157 | $n\text{-}C_3H_7$ | $n\text{-}C_7H_{15}$ | | | |
| 158 | $n\text{-}C_3H_7$ | $CH_3O$ | | | |
| 159 | $n\text{-}C_3H_7$ | $C_2H_5O$ | | | |
| 160 | $n\text{-}C_3H_7$ | $n\text{-}C_3H_7O$ | | | |
| 161 | $n\text{-}C_3H_7$ | $n\text{-}C_4H_9O$ | | | |
| 162 | $n\text{-}C_3H_7$ | $CH_2=CH$ | | | |
| 163 | $n\text{-}C_3H_7$ | $E\text{-}CH_3\text{-}CH=CH$ | | | |
| 164 | $n\text{-}C_3H_7$ | $CH_2=CH\text{-}O$ | | | |
| 165 | $n\text{-}C_3H_7$ | $CH_2=CH\text{-}CH_2O$ | | | |
| 166 | $n\text{-}C_4H_9$ | $CH_3$ | | | |
| 167 | $n\text{-}C_4H_9$ | $C_2H_5$ | | | |
| 168 | $n\text{-}C_4H_9$ | $n\text{-}C_3H_7$ | | | |
| 169 | $n\text{-}C_4H_9$ | $n\text{-}C_4H_9$ | | | |
| 170 | $n\text{-}C_4H_9$ | $n\text{-}C_5H_{11}$ | | | |
| 171 | $n\text{-}C_4H_9$ | $n\text{-}C_6H_{13}$ | | | |
| 172 | $n\text{-}C_4H_9$ | $n\text{-}C_7H_{15}$ | | | |
| 173 | $n\text{-}C_4H_9$ | $CH_3O$ | | | |
| 174 | $n\text{-}C_4H_9$ | $C_2H_5O$ | | | |
| 175 | $n\text{-}C_4H_9$ | $n\text{-}C_3H_7O$ | | | |
| 176 | $n\text{-}C_4H_9$ | $n\text{-}C_4H_9O$ | | | |
| 177 | $n\text{-}C_4H_9$ | $CH_2=CH$ | | | |
| 178 | $n\text{-}C_4H_9$ | $E\text{-}CH_3\text{-}CH=CH$ | | | |
| 179 | $n\text{-}C_4H_9$ | $CH_2=CH\text{-}O$ | | | |
| 180a | $n\text{-}C_4H_9$ | $CH_2=CH\text{-}CH_2O$ | | | |
| 180b | $n\text{-}C_5H_{11}$ | $n\text{-}C_4H_9O$ | | | |
| 181 | $CH_3O$ | $CH_3$ | | | |
| 182 | $CH_3O$ | $C_2H_5$ | | | |
| 183 | $CH_3O$ | $n\text{-}C_3H_7$ | | | |
| 184 | $CH_3O$ | $n\text{-}C_4H_9$ | | | |
| 185 | $CH_3O$ | $n\text{-}C_5H_{11}$ | | | |
| 186 | $CH_3O$ | $n\text{-}C_6H_{13}$ | | | |
| 187 | $CH_3O$ | $n\text{-}C_7H_{15}$ | | | |
| 188 | $CH_3O$ | $CH_3O$ | | | |
| 189 | $CH_3O$ | $C_2H_5O$ | | | |
| 190 | $CH_3O$ | $n\text{-}C_3H_7O$ | | | |
| 191 | $CH_3O$ | $n\text{-}C_4H_9O$ | | | |

-continued

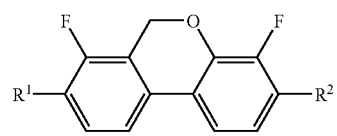

| No. | $R^1$ | $R^2$ | Phase sequence T/°C. | $\Delta\epsilon^*$ | $T^*(N,I)/$ °C. |
|---|---|---|---|---|---|
| 192 | $CH_3O$ | $CH_2=CH$ | | | |
| 193 | $CH_3O$ | $E\text{-}CH_3\text{-}CH=CH$ | | | |
| 194 | $CH_3O$ | $CH_2=CH\text{-}O$ | | | |
| 195 | $CH_3O$ | $CH_2=CH\text{-}CH_2O$ | | | |
| 196 | $C_2H_5O$ | $CH_3$ | | | |
| 197 | $C_2H_5O$ | $C_2H_5$ | | | |
| 198 | $C_2H_5O$ | $n\text{-}C_3H_7$ | | | |
| 199 | $C_2H_5O$ | $n\text{-}C_4H_9$ | | | |
| 200 | $C_2H_5O$ | $n\text{-}C_5H_{11}$ | Tg -39 C 55 N (17.4) I | -6.5 | 39 |
| 201 | $C_2H_5O$ | $n\text{-}C_6H_{13}$ | | | |
| 202 | $C_2H_5O$ | $n\text{-}C_7H_{15}$ | | | |
| 203 | $C_2H_5O$ | $CH_3O$ | | | |
| 204 | $C_2H_5O$ | $C_2H_5O$ | | | |
| 205 | $C_2H_5O$ | $n\text{-}C_3H_7O$ | | | |
| 206 | $C_2H_5O$ | $n\text{-}C_4H_9O$ | | | |
| 207 | $C_2H_5O$ | $CH_2=CH$ | | | |
| 208 | $C_2H_5O$ | $E\text{-}CH_3\text{-}CH=CH$ | | | |
| 209 | $C_2H_5O$ | $CH_2=CH\text{-}O$ | | | |
| 210a | $C_2H_5O$ | $CH_2=CH\text{-}CH_2O$ | | | |
| 210b | $n\text{-}C_4H_9O$ | $n\text{-}C_5H_{11}$ | | | |
| 211 | $CH_2=CH$ | $CH_3$ | | | |
| 212 | $CH_2=CH$ | $C_2H_5$ | | | |
| 213 | $CH_2=CH$ | $n\text{-}C_3H_7$ | | | |
| 214 | $CH_2=CH$ | $n\text{-}C_4H_9$ | | | |
| 215 | $CH_2=CH$ | $n\text{-}C_5H_{11}$ | | | |
| 216 | $CH_2=CH$ | $n\text{-}C_6H_{13}$ | | | |
| 217 | $CH_2=CH$ | $n\text{-}C_7H_{15}$ | | | |
| 218 | $CH_2=CH$ | $CH_3O$ | | | |
| 219 | $CH_2=CH$ | $C_2H_5O$ | | | |
| 220 | $CH_2=CH$ | $n\text{-}C_3H_7O$ | | | |
| 221 | $CH_2=CH$ | $n\text{-}C_4H_9O$ | | | |
| 222 | $CH_2=CH$ | $CH_2=CH$ | | | |
| 223 | $CH_2=CH$ | $E\text{-}CH_3\text{-}CH=CH$ | | | |
| 224 | $CH_2=CH$ | $CH_2=CH\text{-}O$ | | | |
| 225 | $CH_2=CH$ | $CH_2=CH\text{-}CH_2O$ | | | |
| 226 | $CH_2=CH\text{-}O$ | $CH_3$ | | | |
| 227 | $CH_2=CH\text{-}O$ | $C_2H_5$ | | | |
| 228 | $CH_2=CH\text{-}O$ | $n\text{-}C_3H_7$ | | | |
| 229 | $CH_2=CH\text{-}O$ | $n\text{-}C_4H_9$ | | | |
| 230 | $CH_2=CH\text{-}O$ | $n\text{-}C_5H_{11}$ | | | |
| 231 | $CH_2=CH\text{-}O$ | $n\text{-}C_6H_{13}$ | | | |
| 232 | $CH_2=CH\text{-}O$ | $n\text{-}C_7H_{15}$ | | | |
| 233 | $CH_2=CH\text{-}O$ | $CH_3O$ | | | |
| 234 | $CH_2=CH\text{-}O$ | $C_2H_5O$ | | | |
| 235 | $CH_2=CH\text{-}O$ | $n\text{-}C_3H_7O$ | | | |
| 236 | $CH_2=CH\text{-}O$ | $n\text{-}C_4H_9O$ | | | |
| 237 | $CH_2=CH\text{-}O$ | $CH_2=CH$ | | | |
| 238 | $CH_2=CH\text{-}O$ | $E\text{-}CH_3\text{-}CH=CH$ | | | |
| 239 | $CH_2=CH\text{-}O$ | $CH_2=CH\text{-}O$ | | | |
| 240 | $CH_2=CH\text{-}O$ | $CH_2=CH\text{-}CH_2O$ | | | |

Note:
*values extrapolated from 10% solution in ZLI-4792 or ZLI-2857 ($\Delta\epsilon$).

Example 241

(8-Ethoxy-4,6,6,7-tetrafluoro-3-pentyl-6H-benzo[c]-chromene)

Preparation of 8-ethoxy-4,6,6,7-tetrafluoro-3-pentyl-6H-benzo[c]chromene

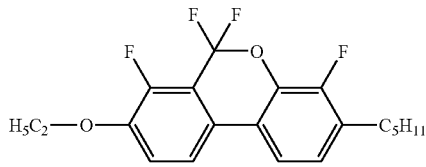

4.00 g (11.5 mmol) of the compound from Example 80 and 5.14 g (12.7 mmol) of Lawesson's reagent were dissolved in 60 ml of chlorobenzene, and the mixture was refluxed for 48 hours. The batch was subsequently evaporated and subjected to conventional purification, giving 2.90 g (8.00 mmol) of the corresponding thionolactone as an orange solid. This corresponds to a yield of 69%.

The thionolactone was dissolved in 40 ml of dichloromethane. 2.1 ml (16.1 mmol) of DAST were then added, and the mixture was stirred at about 20° C. for 16 hours and subjected to conventional purification. The crude product was purified via silica gel with a mixture of n-heptane/ethyl acetate (9:1) and recrystallised from ethanol, giving 0.46 9 of the difluorobenzochromene. This corresponds to a yield of 15%.

Examples 242 to 360

The following are prepared analogously to Example 241:

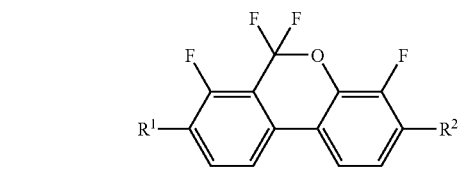

| No. | $R^1$ | $R^2$ | Phase sequence T/° C. | $\Delta\epsilon^*$ |
|---|---|---|---|---|
| 242 | $CH_3$ | $CH_3$ | | |
| 243 | $CH_3$ | $C_2H_5$ | | |
| 244 | $CH_3$ | $n\text{-}C_3H_7$ | | |
| 245 | $CH_3$ | $n\text{-}C_4H_9$ | | |
| 246 | $CH_3$ | $n\text{-}C_5H_{11}$ | | |
| 247 | $CH_3$ | $n\text{-}C_6H_{13}$ | | |
| 248 | $CH_3$ | $n\text{-}C_7H_{15}$ | | |
| 249 | $CH_3$ | $CH_3O$ | | |
| 250 | $CH_3$ | $C_2H_5O$ | | |
| 251 | $CH_3$ | $n\text{-}C_3H_7O$ | | |
| 252 | $CH_3$ | $n\text{-}C_4H_9O$ | | |
| 253 | $CH_3$ | $CH_2\text{=}CH$ | | |
| 254 | $CH_3$ | $E\text{-}CH_3\text{—}CH\text{=}CH$ | | |
| 255 | $CH_3$ | $CH_2\text{=}CH\text{—}O$ | | |
| 256 | $CH_3$ | $CH_2\text{=}CH\text{—}CH_2O$ | | |
| 257 | $C_2H_5$ | $CH_3$ | | |
| 258 | $C_2H_5$ | $C_2H_5$ | | |
| 259 | $C_2H_5$ | $n\text{-}C_3H_7$ | | |
| 260 | $C_2H_5$ | $n\text{-}C_4H_9$ | | |
| 261 | $C_2H_5$ | $n\text{-}C_5H_{11}$ | | |
| 262 | $C_2H_5$ | $n\text{-}C_6H_{13}$ | | |
| 263 | $C_2H_5$ | $n\text{-}C_7H_{15}$ | | |

-continued

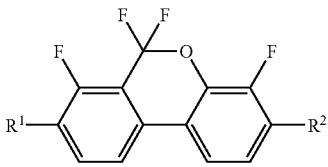

| No. | $R^1$ | $R^2$ | Phase sequence T/° C. | $\Delta\epsilon^*$ |
|---|---|---|---|---|
| 264 | $C_2H_5$ | $CH_3O$ | | |
| 265 | $C_2H_5$ | $C_2H_5O$ | | |
| 266 | $C_2H_5$ | $n\text{-}C_3H_7O$ | | |
| 267 | $C_2H_5$ | $n\text{-}C_4H_9O$ | | |
| 268 | $C_2H_5$ | $CH_2\text{=}CH$ | | |
| 269 | $C_2H_5$ | $E\text{-}CH_3\text{—}CH\text{=}CH$ | | |
| 270 | $C_2H_5$ | $CH_2\text{=}CH\text{—}O$ | | |
| 271 | $C_2H_5$ | $CH_2\text{=}CH\text{—}CH_2O$ | | |
| 272 | $n\text{-}C_3H_7$ | $CH_3$ | | |
| 273 | $n\text{-}C_3H_7$ | $C_2H_5$ | | |
| 274 | $n\text{-}C_3H_7$ | $n\text{-}C_3H_7$ | | |
| 275 | $n\text{-}C_3H_7$ | $n\text{-}C_4H_9$ | | |
| 276 | $n\text{-}C_3H_7$ | $n\text{-}C_5H_{11}$ | C 53 I | −10.4 |
| 277 | $n\text{-}C_3H_7$ | $n\text{-}C_6H_{13}$ | | |
| 278 | $n\text{-}C_3H_7$ | $n\text{-}C_7H_{15}$ | | |
| 279 | $n\text{-}C_3H_7$ | $CH_3O$ | | |
| 280 | $n\text{-}C_3H_7$ | $C_2H_5O$ | | |
| 281 | $n\text{-}C_3H_7$ | $n\text{-}C_3H_7O$ | | |
| 282 | $n\text{-}C_3H_7$ | $n\text{-}C_4H_9O$ | | |
| 283 | $n\text{-}C_3H_7$ | $CH_2\text{=}CH$ | | |
| 284 | $n\text{-}C_3H_7$ | $E\text{-}CH_3\text{—}CH\text{=}CH$ | | |
| 285 | $n\text{-}C_3H_7$ | $CH_2\text{=}CH\text{—}O$ | | |
| 286 | $n\text{-}C_3H_7$ | $CH_2\text{=}CH\text{—}CH_2O$ | | |
| 287 | $n\text{-}C_4H_9$ | $CH_3$ | | |
| 288 | $n\text{-}C_4H_9$ | $C_2H_5$ | | |
| 289 | $n\text{-}C_4H_9$ | $n\text{-}C_3H_7$ | | |
| 290 | $n\text{-}C_4H_9$ | $n\text{-}C_4H_9$ | | |
| 291 | $n\text{-}C_4H_9$ | $n\text{-}C_5H_{11}$ | | |
| 292 | $n\text{-}C_4H_9$ | $n\text{-}C_6H_{13}$ | | |
| 293 | $n\text{-}C_4H_9$ | $n\text{-}C_7H_{15}$ | | |
| 294 | $n\text{-}C_4H_9$ | $CH_3O$ | | |
| 295 | $n\text{-}C_4H_9$ | $C_2H_5O$ | | |
| 296 | $n\text{-}C_4H_9$ | $n\text{-}C_3H_7O$ | | |
| 297 | $n\text{-}C_4H_9$ | $n\text{-}C_4H_9O$ | | |
| 298 | $n\text{-}C_4H_9$ | $CH_2\text{=}CH$ | | |
| 299 | $n\text{-}C_4H_9$ | $E\text{-}CH_3\text{—}CH\text{=}CH$ | | |
| 300 | $n\text{-}C_4H_9$ | $CH_2\text{=}CH\text{—}O$ | | |
| 301a | $n\text{-}C_4H_9$ | $CH_2\text{=}CH\text{—}CH_2O$ | | |
| 301b | $n\text{-}C_5H_{11}$ | $n\text{-}C_4H_9O$ | | |
| 302 | $CH_3O$ | $CH_3$ | | |
| 303 | $CH_3O$ | $C_2H_5$ | | |
| 304 | $CH_3O$ | $n\text{-}C_3H_7$ | | |
| 305 | $CH_3O$ | $n\text{-}C_4H_9$ | | |
| 306 | $CH_3O$ | $n\text{-}C_5H_{11}$ | | |
| 307 | $CH_3O$ | $n\text{-}C_6H_{13}$ | | |
| 308 | $CH_3O$ | $n\text{-}C_7H_{15}$ | | |
| 309 | $CH_3O$ | $CH_3O$ | | |
| 310 | $CH_3O$ | $C_2H_5O$ | | |
| 311 | $CH_3O$ | $n\text{-}C_3H_7O$ | | |
| 312 | $CH_3O$ | $n\text{-}C_4H_9O$ | | |
| 313 | $CH_3O$ | $CH_2\text{=}CH$ | | |
| 314 | $CH_3O$ | $E\text{-}CH_3\text{—}CH\text{=}CH$ | | |
| 315 | $CH_3O$ | $CH_2\text{=}CH\text{—}O$ | | |
| 316 | $CH_3O$ | $CH_2\text{=}CH\text{—}CH_2O$ | | |
| 317 | $C_2H_5O$ | $CH_3$ | | |
| 318 | $C_2H_5O$ | $C_2H_5$ | | |
| 319 | $C_2H_5O$ | $n\text{-}C_3H_7$ | | |
| 320 | $C_2H_5O$ | $n\text{-}C_4H_9$ | | |
| 241 | $C_2H_5O$ | $n\text{-}C_5H_{11}$ | C 85 I | −15.4 |
| 321 | $C_2H_5O$ | $n\text{-}C_6H_{13}$ | | |
| 322 | $C_2H_5O$ | $n\text{-}C_7H_{15}$ | | |
| 323 | $C_2H_5O$ | $CH_3O$ | | |
| 324 | $C_2H_5O$ | $C_2H_5O$ | | |
| 325 | $C_2H_5O$ | $n\text{-}C_3H_7O$ | | |
| 326 | $C_2H_5O$ | $n\text{-}C_4H_9O$ | | |
| 327 | $C_2H_5O$ | $CH_2\text{=}CH$ | | |
| 328 | $C_2H_5O$ | $E\text{-}CH_3\text{—}CH\text{=}CH$ | | |

-continued

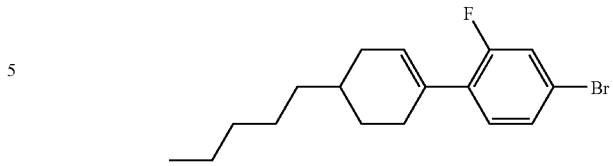

| No. | R¹ | R² | Phase sequence T/° C. | Δε* |
|---|---|---|---|---|
| 329 | $C_2H_5O$ | $CH_2=CH-O$ | | |
| 330a | $C_2H_5O$ | $CH_2=CH-CH_2O$ | | |
| 330b | $n-C_4H_9O$ | $n-C_5H_{11}$ | | |
| 331 | $CH_2=CH$ | $CH_3$ | | |
| 332 | $CH_2=CH$ | $C_2H_5$ | | |
| 333 | $CH_2=CH$ | $n-C_3H_7$ | | |
| 334 | $CH_2=CH$ | $n-C_4H_9$ | | |
| 335 | $CH_2=CH$ | $n-C_5H_{11}$ | | |
| 336 | $CH_2=CH$ | $n-C_6H_{13}$ | | |
| 337 | $CH_2=CH$ | $n-C_7H_{15}$ | | |
| 338 | $CH_2=CH$ | $CH_3O$ | | |
| 339 | $CH_2=CH$ | $C_2H_5O$ | | |
| 340 | $CH_2=CH$ | $n-C_3H_7O$ | | |
| 341 | $CH_2=CH$ | $n-C_4H_9O$ | | |
| 342 | $CH_2=CH$ | $CH_2=CH$ | | |
| 343 | $CH_2=CH$ | $E-CH_3-CH=CH$ | | |
| 344 | $CH_2=CH$ | $CH_2=CH-O$ | | |
| 345 | $CH_2=CH$ | $CH_2=CH-CH_2O$ | | |
| 346 | $CH_2=CH-O$ | $CH_3$ | | |
| 347 | $CH_2=CH-O$ | $C_2H_5$ | | |
| 348 | $CH_2=CH-O$ | $n-C_3H_7$ | | |
| 349 | $CH_2=CH-O$ | $n-C_4H_9$ | | |
| 350 | $CH_2=CH-O$ | $n-C_5H_{11}$ | | |
| 351 | $CH_2=CH-O$ | $n-C_6H_{13}$ | | |
| 352 | $CH_2=CH-O$ | $n-C_7H_{15}$ | | |
| 353 | $CH_2=CH-O$ | $CH_3O$ | | |
| 354 | $CH_2=CH-O$ | $C_2H_5O$ | | |
| 355 | $CH_2=CH-O$ | $n-C_3H_7O$ | | |
| 356 | $CH_2=CH-O$ | $n-C_4H_9O$ | | |
| 357 | $CH_2=CH-O$ | $CH_2=CH$ | | |
| 358 | $CH_2=CH-O$ | $E-CH_3-CH=CH$ | | |
| 359 | $CH_2=CH-O$ | $CH_2=CH-O$ | | |
| 360 | $CH_2=CH-O$ | $CH_2=CH-CH_2O$ | | |

Note:
*values extrapolated from 10% solution in ZLI-4792 or ZLI-2857 (Δε).

Example 361a (3-Butoxy-4,6,6,7-tetrafluoro-8-(4-pentylcyclo-hexyl)-6H-benzo[c]chromene)

361.1 Preparation of 4-bromo-2-fluoro-1-(4-pentylcyclo-hex-1-enyl)benzene

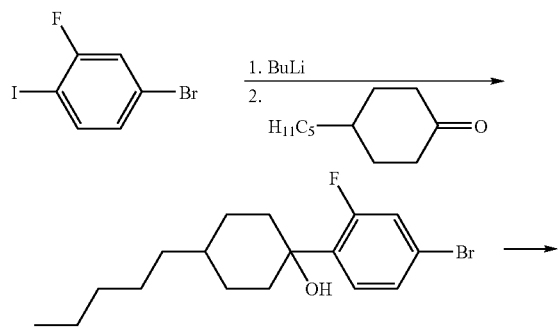

200 g (0.665 mol) of 1-bromo-3-fluoro-4-iodobenzene were dissolved in 800 ml of tetrahydrofuran, and 440 ml (0.698 mmol) of a 15 percent solution of n-butyllithium in hexane were added dropwise at −70° C. After 30 minutes, a solution of 117 g (0.698 mol) of 4-pentylcyclohexanone in 200 ml of tetrahydrofuran was added, and the batch was left to stir for 60 minutes, hydrolysed using water and acidified using conc. hydrochloric acid. The organic phase was separated off, washed with water and dried over sodium sulfate, and the solvent was removed under reduced pressure. The crude product was subsequently dissolved in 1.4 l of toluene and, after addition of 6 g of toluenesulfonic acid, heated on a water separator until water of reaction was no longer separated off. The solution was washed with water and evaporated, and the residue was filtered through silica gel with n-heptane, giving 124 g (58%) of 4-bromo-2-fluoro-1-(4-pentylcyclohex-1-enyl)benzene as a yellow oil.

361.2 Preparation of 4-bromo-2-fluoro-1-(4-pentylcyclo-hexyl)benzene

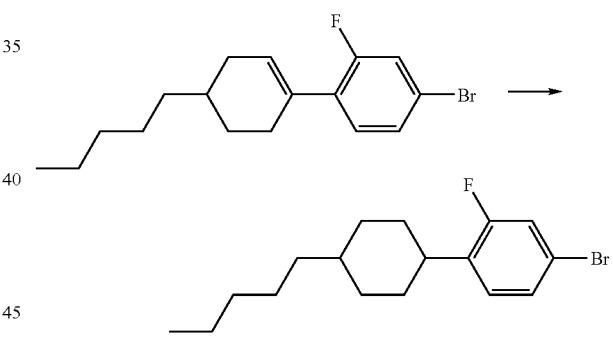

124 g (0.382 mol) of 4-bromo-2-fluoro-1-(4-pentylcyclohex-1-enyl)benzene were hydrogenated to completion at 5 bar and 50° C. in tetrahydrofuran on platinum/activated carbon catalyst. Filtration and removal of the solvent under reduced pressure gave 114 g (80%) of a mixture of cis- and trans-4-bromo-2-fluoro-1-(4-pentylcyclohexyl)benzene as a yellow oil. For isomerisation, this was dissolved in 200 ml of dichloromethane and added dropwise to a suspension of 12.5 g (95.7 mmol) of aluminium chloride in 220 ml of dichloromethane. After 30 minutes, 300 ml of water were added, and the organic phase was separated off, washed with water and dried over sodium sulfate. The solvent was removed under reduced pressure, and the residue was filtered through silica gel with n-pentane, giving 85.2 g of crude product having a content of trans-4-bromo-2-fluoro-1-(4-pentyl-cyclohexyl)benzene of 52.8% and a content of cis-4-bromo-2-fluoro-1-(4-pentylcyclohexyl)benzene of 9.7% as a yellow liquid, which was employed in the next step without further purification.

361.3 Preparation of trans-6-bromo-2-fluoro-3-(4-pentylcyclohexyl)benzoic acid

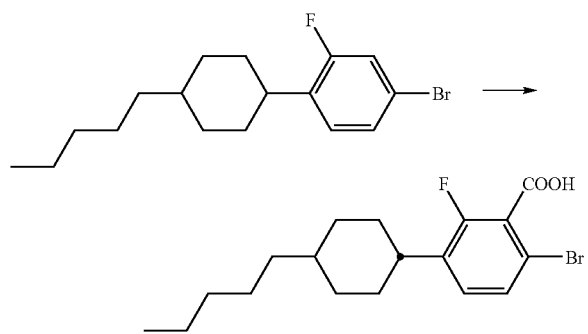

85.2 g (0.163 mol) of the crude product from the preceding step were initially introduced in 400 ml of tetrahydrofuran at −70° C., and a solution of lithium diisopropylamide, prepared from 213 ml of 15 percent n-butyllithium in hexane and 46 ml (0.326 mmol) of diisopropylamine in 100 ml of tetrahydrofuran, was added dropwise. After 1 hour, 22.9 g (0.521 mol) of carbon dioxide were passed in. The batch was allowed to thaw, acidified using conc. hydrochloric acid and extracted twice with MTB ether. The combined organic phases were washed with water and dried over sodium sulfate, and the solvent was removed under reduced pressure. Crystallisation from n-heptane gave 17 g (28%) of trans-6-bromo-2-fluoro-3-(4-pentylcyclohexyl)benzoic acid as colourless crystals.

361.4 Preparation of methyl trans-6-bromo-2-fluoro-3-(4-pentylcyclohexyl)-benzoate

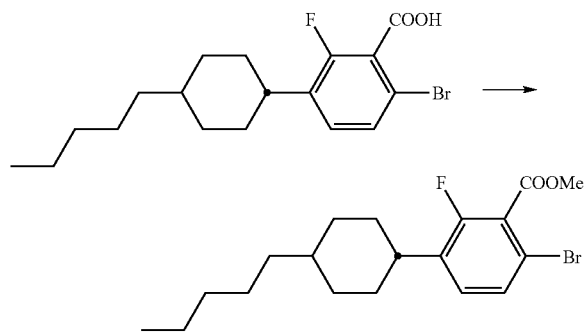

17.1 g (46.0 mmol) of trans-6-bromo-2-fluoro-3-(4-pentylcyclohexyl)-benzoic acid were dissolved in 70 ml of acetone, 7.66 g (55.4 mmol) of potassium carbonate and 3.14 ml (50.6 mmol) of methyl iodide were added, and the mixture was refluxed overnight. The batch was filtered, and the solvent was distilled off, giving 18 g (100%) of methyl 6-bromo-2-fluoro-3-(4-pentylcyclohexyl)benzoate as a colourless oil, which was reacted further without further purification.

361.5 Preparation of 1-bromo-4-butoxy-3-fluoro-2-(2-methoxyethoxy-methoxy)benzene

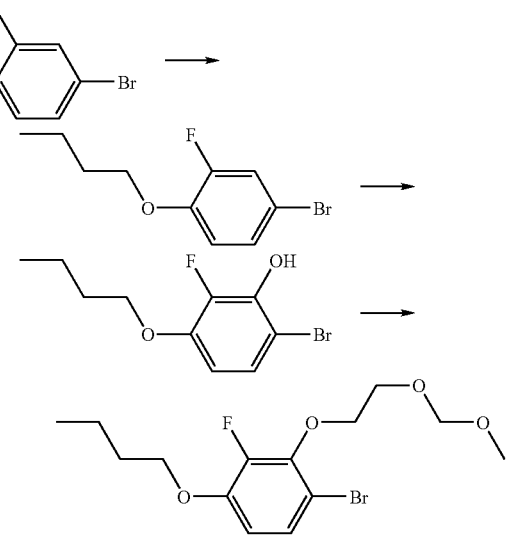

Analogously to Examples 841.1 and 841.4, 4-bromo-2-fluorophenol gave 6-bromo-3-butoxy-2-fluorophenol as a brown oil (80%, 2 steps).

60.4 ml (0.355 mol) of ethyldiisopropylamine were added with ice-cooling to 77.4 g (0.294 mol) of 6-bromo-3-butoxy-2-fluorophenol dissolved in 500 ml of dichloromethane, 40.3 ml (0.355 mol) of 2-methoxyethoxymethyl chloride were added dropwise, and the mixture was left to stirr overnight at room temperature. The batch was hydrolysed using water, extracted with dichloromethane and evaporated, and the crude product was filtered through silica gel with n-heptane/MTB ether (3:1), giving 103 g (99%) of 1-bromo-4-butoxy-3-fluoro-2-(2-methoxyethoxymethoxy) benzene as a yellow oil.

361.6 Preparation of 3-butoxy-4,7-difluoro-8-(4-pentylcyclohexyl)-benzo[c]chromen-6-one

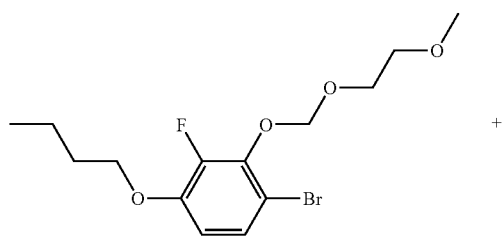 +

-continued

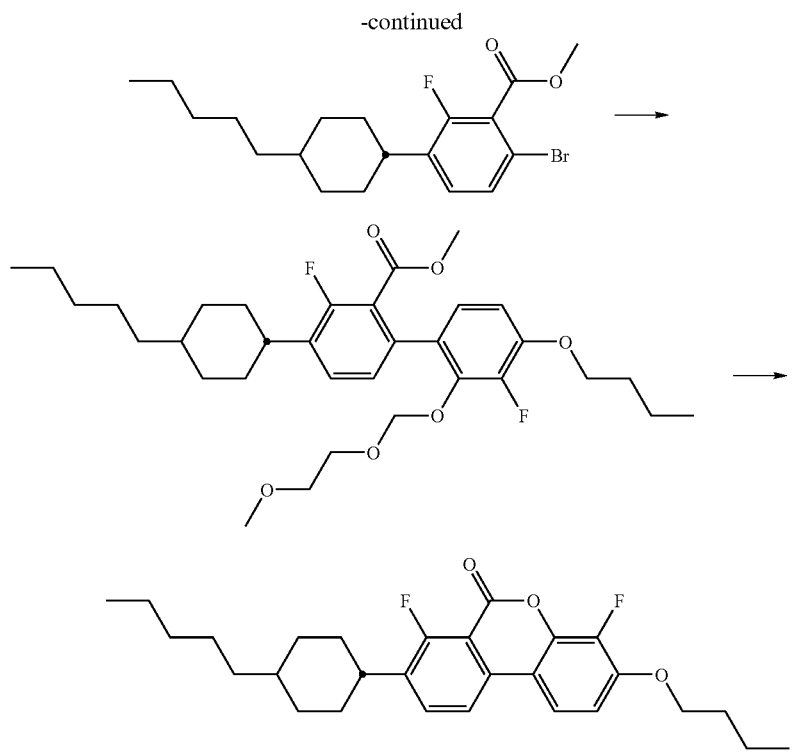

16.4 g (0.046 mol) of 1-bromo-4-butoxy-3-fluoro-2-(2-methoxyethoxy-methoxy)benzene were dissolved in 20 ml of tetrahydrofuran, and 31.6 ml (0.052 mol) of a 15 percent solution of n-butyllithium in hexane were added at −70° C. After addition of a solution of 5.94 g (0.027 mol) of zinc bromide in 30 ml of tetrahydrofuran, the batch was allowed to thaw, and the resultant solution was added at the boiling point to a mixture of 18 g (0.046 mol) of methyl 6-bromo-2-fluoro-3-(4-pentylcyclohexyl)benzoate and 730 mg (1.00 mmol) of Pd(dppf)$_2$Cl$_2$ in 60 ml of tetrahydrofuran. The batch was refluxed for 4 hours, stirred overnight at room temperature, acidified using dilute hydrochloric acid and extracted with MTB ether. The combined organic phases were washed with water, dried over sodium sulfate and evaporated. The crude product was chromatographed over silica gel with n-pentane/MTB ether (3:1), giving 14.6 g (55%) of methyl 4'-butoxy-3,3'-difluoro-2'-(2-methoxyethoxymethoxy)-4-(4-pentylcyclohexyl)-biphenyl-2-carboxylate as a yellow oil. This was dissolved in 56 ml of tetrahydrofuran, 11 ml of conc. hydrochloric acid were added, and the mixture was stirred overnight at room temperature. The precipitated product was filtered off with suction, washed with ethyl acetate and dried, giving 7.6 g (68%) of 3-butoxy-4,7-difluoro-8-(4-pentylcyclohexyl)-benzo[c]chromen-6-one as colourless crystals.

361.7 Preparation of 3-butoxy-4,7-difluoro-8-(4-pentylcyclohexyl)-benzo[c]chromene-6-thione

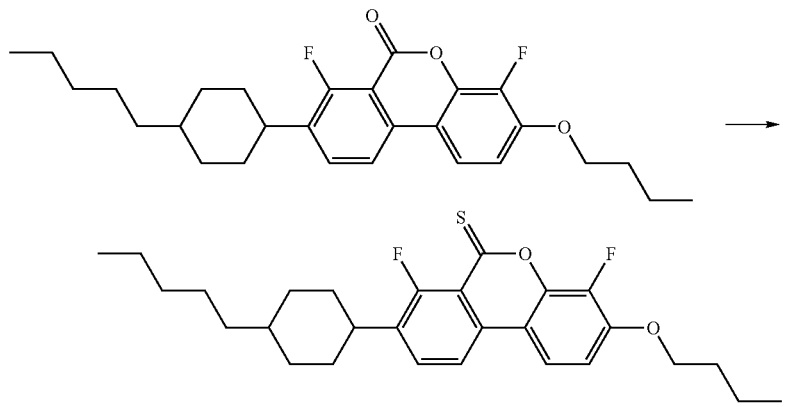

11.7 g (25.6 mmol) of 3-butoxy-4,7-difluoro-8-(4-pentylcyclohexyl)-benzo[c]chromen-6-one and 11.4 g (28.2 mmol) of Lawesson's reagent were refluxed for 16 hours in 130 ml of chlorobenzene. The solution was subsequently filtered through silica gel and evaporated, and the crude product was purified by crystallisation from MTB ether, giving 7.9 g (65%) of 3-butoxy-4,7-difluoro-8-(4-pentylcyclohexyl)benzo[c]chromene-6-thione as yellow crystals.

361.8 Preparation of 3-butoxy-4,6,6,7-tetrafluoro-8-(4-pentylcyclohexyl)-6H-benzo[c]chromene romethane. The organic phases were washed with water, dried over sodium sulfate and evaporated, and the crude product was chromatographed over silica gel with heptane/toluene (1:2). Crystallisation from n-heptane gave 1.0 g (52%) of 3-butoxy-4,6,6,7-tetrafluoro-8-(4-pentylcyclohexyl)-6H-benzo[c]chromene as colourless crystals of melting point 99° C.

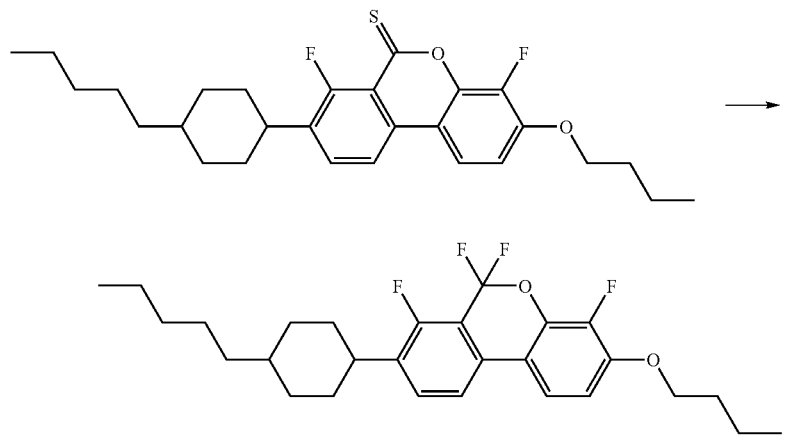

2.00 g (4.18 mmol) of 3-butoxy-4,7-difluoro-8-(4-pentylcyclohexyl)benzo-[c]chromene-6-thione were dissolved in 20 ml of dichloromethane and cooled to −70° C., 0.55 ml (20 mmol) of a 65 percent solution of hydrogen fluoride in pyridine was added, and a suspension of 2.56 g (8.36 mmol) of 1,3-dibromo-5,5-dimethylhydantoin in 12 ml of dichloromethane was added in portions. After 2 hours, the batch was allowed to thaw, and was neutralised using sat. sodium hydrogencarbonate solution and extracted with dichlo- The compound exhibited the following phase behaviour: C 99° C. N 130.5° C. I and has an extrapolated clearing point of 148° C., and at 20° C. an extrapolated birefringence of 0.153 and an extrapolated dielectric anisotropy of −16.7.

Examples 361b and 362 to 390

The following are prepared analogously to Example 241 and Example 361a:

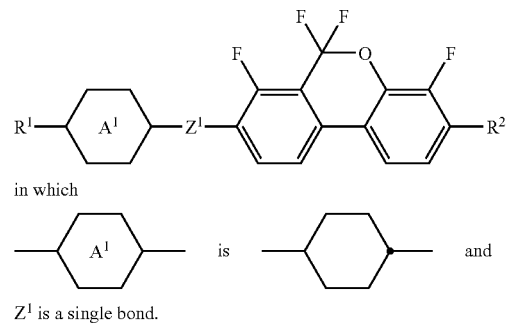

in which $A^1$ is cyclohexyl and $Z^1$ is a single bond.

| No. | $R^1$ | $R^2$ | Phase sequence T/° C. | Δε* | T*(N,I)/ ° C. |
|---|---|---|---|---|---|
| 361b | $CH_3$ | $CH_3$ | | | |
| 362 | $CH_3$ | $C_2H_5$ | | | |
| 363 | $CH_3$ | $n-C_3H_7$ | | | |
| 364 | $C_2H_5$ | $CH_3$ | | | |
| 365 | $C_2H_5$ | $C_2H_5$ | | | |
| 366 | $C_2H_5$ | $n-C_3H_7$ | | | |
| 367 | $n-C_3H_7$ | $CH_3$ | | | |
| 368 | $n-C_3H_7$ | $C_2H_5$ | | | |
| 369 | $n-C_3H_7$ | $n-C_3H_7$ | | | |
| 370 | $n-C_3H_7$ | $n-C_5H_{11}$ | | | |

-continued

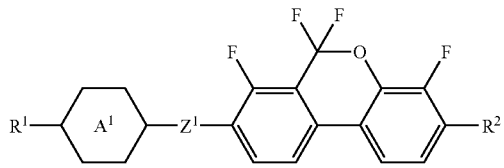

in which

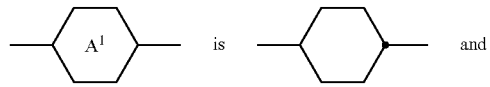 is 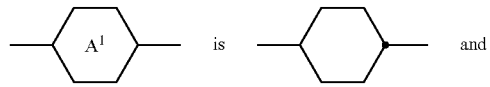 and $Z^1$ is a single bond.

| No. | $R^1$ | $R^2$ | Phase sequence T/° C. | Δε* | T*(N,I)/ ° C. |
|---|---|---|---|---|---|
| 371 | n-$C_5H_{11}$ | n-$C_3H_7$ | | | |
| 372 | n-$C_5H_{11}$ | n-$C_5H_{11}$ | | | |
| 373 | $CH_2$=CH | $CH_3$ | | | |
| 374 | $CH_2$=CH | $C_2H_5$ | | | |
| 375 | $CH_2$=CH | n-$C_3H_7$ | | | |
| 376 | $CH_2$=CH | $CH_2$=CH | | | |
| 377 | $CH_3$ | $CH_2$=CH | | | |
| 378 | $C_2H_5$ | $CH_2$=CH | | | |
| 379 | n-$C_3H_7$ | $CH_2$=CH | | | |
| 380 | E-$CH_3$—CH=CH | $CH_2$=CH | | | |
| 381 | E-$CH_3$—CH=CH | E-$CH_3$—CH=CH | | | |
| 382 | $CH_3$ | $CH_3$O | | | |
| 383 | $CH_3$ | $C_2H_5$O | | | |
| 384 | $CH_3$ | n-$C_3H_7$O | | | |
| 385 | n-$C_3H_7$ | $CH_3$O | | | |
| 386 | n-$C_3H_7$ | $C_2H_5$O | | | |
| 387 | n-$C_3H_7$ | n-$C_3H_7$O | | | |
| 361a | n-$C_5H_{11}$ | n-$C_4H_9$O | C 99 N 130.5 I | −16.7 | 148 |
| 388a | n-$C_4H_9$O | n-$C_5H_{11}$ | | | |
| 388b | $CH_3$O | $CH_3$O | | | |
| 389 | $C_2H_5$O | $C_2H_5$O | | | |
| 390 | n-$C_3H_7$O | n-$C_3H_7$O | | | |

Note:
*values extrapolated from 10% solution in ZLI-4792 or ZLI-2857 (Δε).

Examples 391 to 420

The following are prepared analogously to Example 241 and Example 361a:

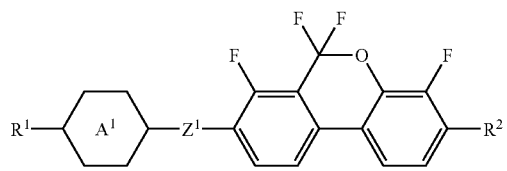

in which

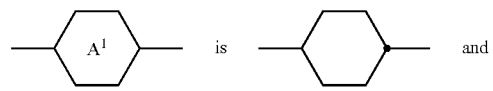 is 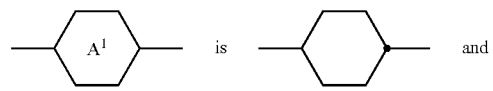 and $Z^1$ is —$CF_2$—O—.

| No. | $R^1$ | $R^2$ | Phase sequence T/° C. | Δε* |
|---|---|---|---|---|
| 391 | $CH_3$ | $CH_3$ | | |
| 392 | $CH_3$ | $C_2H_5$ | | |
| 393 | $CH_3$ | n-$C_3H_7$ | | |
| 394 | $C_2H_5$ | $CH_3$ | | |
| 395 | $C_2H_5$ | $C_2H_5$ | | |

-continued

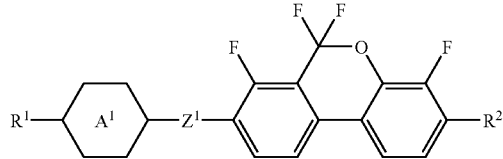

in which

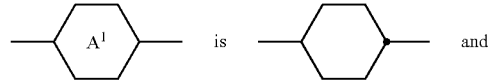 is 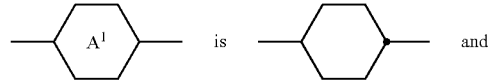 and $Z^1$ is —$CF_2$—O—.

| No. | $R^1$ | $R^2$ | Phase sequence T/° C. | Δε* |
|---|---|---|---|---|
| 396 | $C_2H_5$ | n-$C_3H_7$ | | |
| 397 | n-$C_3H_7$ | $CH_3$ | | |
| 398 | n-$C_3H_7$ | $C_2H_5$ | | |
| 399 | n-$C_3H_7$ | n-$C_3H_7$ | | |
| 400 | n-$C_3H_7$ | n-$C_5H_{11}$ | | |
| 401 | n-$C_5H_{11}$ | n-$C_3H_7$ | | |
| 402 | n-$C_5H_{11}$ | n-$C_5H_{11}$ | | |
| 403 | $CH_2$=CH | $CH_3$ | | |
| 404 | $CH_2$=CH | $C_2H_5$ | | |
| 405 | $CH_2$=CH | n-$C_3H_7$ | | |

-continued

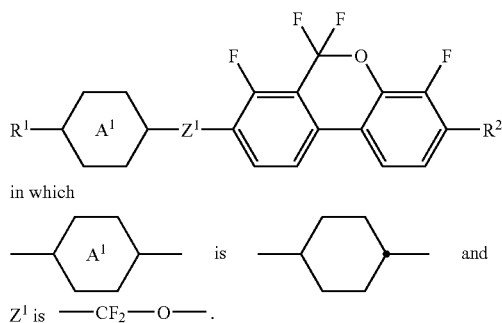

in which

―⬡― is ―⬡― and $Z^1$ is ―$CF_2$―O―.

| No. | $R^1$ | $R^2$ | Phase sequence T/° C. | Δε* |
|---|---|---|---|---|
| 406 | $CH_2$=CH | $CH_2$=CH | | |
| 407 | $CH_3$ | $CH_2$=CH | | |
| 408 | $C_2H_5$ | $CH_2$=CH | | |
| 409 | n-$C_3H_7$ | $CH_2$=CH | | |
| 410 | E-$CH_3$—CH=CH | $CH_2$=CH | | |
| 411 | E-$CH_3$—CH=CH | E-$CH_3$—CH=CH | | |
| 412 | $CH_3$ | $CH_3$O | | |
| 413 | $CH_3$ | $C_2H_5$O | | |
| 414 | $CH_3$ | n-$C_3H_7$O | | |
| 415 | n-$C_3H_7$ | $CH_3$O | | |
| 416 | n-$C_3H_7$ | $C_2H_5$O | | |
| 417a | n-$C_3H_7$ | n-$C_3H_7$O | | |
| 417b | n-$C_5H_{11}$ | n-$C_4H_9$O | | |
| 417c | n-$C_4H_9$O | n-$C_5H_{11}$ | | |
| 418 | $CH_3$O | $CH_3$O | | |
| 419 | $C_2H_5$O | $C_2H_5$O | | |
| 420 | n-$C_3H_7$O | n-$C_3H_7$O | | |

Note:
*values extrapolated from 10% solution in ZLI-4792 or ZLI-2857 (Δε).

Examples 421 to 450

The following are prepared analogously to Example 241 and Example 361a:

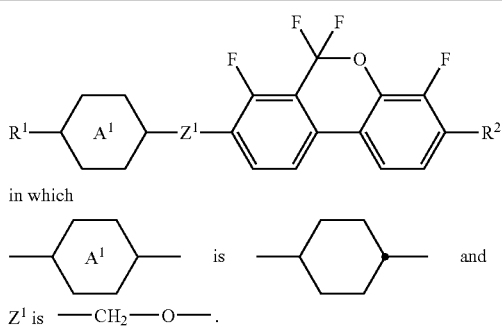

in which

―⬡― is ―⬡― and $Z^1$ is ―$CH_2$―O―.

| No. | $R^1$ | $R^2$ | Phase sequence T/° C. | Δε* |
|---|---|---|---|---|
| 421 | $CH_3$ | $CH_3$ | | |
| 422 | $CH_3$ | $C_2H_5$ | | |
| 423 | $CH_3$ | n-$C_3H_7$ | | |
| 424 | $C_2H_5$ | $CH_3$ | | |
| 425 | $C_2H_5$ | $C_2H_5$ | | |
| 426 | $C_2H_5$ | n-$C_3H_7$ | | |
| 427 | n-$C_3H_7$ | $CH_3$ | | |
| 428 | n-$C_3H_7$ | $C_2H_5$ | | |
| 429 | n-$C_3H_7$ | n-$C_3H_7$ | | |
| 430 | n-$C_3H_7$ | n-$C_5H_{11}$ | | |

-continued

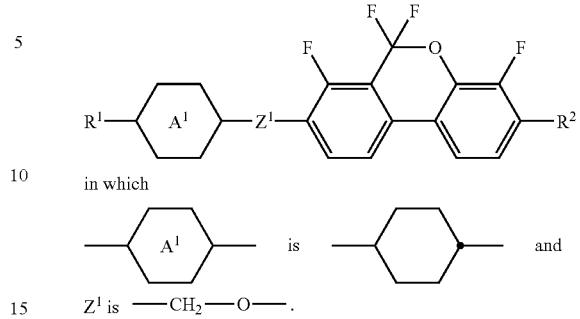

in which

―⬡― is ―⬡― and $Z^1$ is ―$CH_2$―O―.

| No. | $R^1$ | $R^2$ | Phase sequence T/° C. | Δε* |
|---|---|---|---|---|
| 431 | n-$C_5H_{11}$ | n-$C_3H_7$ | | |
| 432 | n-$C_5H_{11}$ | n-$C_5H_{11}$ | | |
| 453 | $CH_2$=CH | $CH_3$ | | |
| 434 | $CH_2$=CH | $C_2H_5$ | | |
| 435 | $CH_2$=CH | n-$C_3H_7$ | | |
| 436 | $CH_2$=CH | $CH_2$=CH | | |
| 437 | $CH_3$ | $CH_2$=CH | | |
| 438 | $C_2H_5$ | $CH_2$=CH | | |
| 439 | n-$C_3H_7$ | $CH_2$=CH | | |
| 440 | E-$CH_3$—CH=CH | $CH_2$=CH | | |
| 441 | E-$CH_3$—CH=CH | E-$CH_3$—CH=CH | | |
| 442 | $CH_3$ | $CH_3$O | | |
| 443 | $CH_3$ | $C_2H_5$O | | |
| 444 | $CH_3$ | n-$C_3H_7$O | | |
| 445 | n-$C_3H_7$ | $CH_3$O | | |
| 446 | n-$C_3H_7$ | $C_2H_5$O | | |
| 447a | n-$C_3H_7$ | n-$C_3H_7$O | | |
| 447b | n-$C_5H_{11}$ | n-$C_4H_9$O | | |
| 447c | n-$C_4H_9$O | n-$C_5H_{11}$ | | |
| 448 | $CH_3$O | $CH_3$O | | |
| 449 | $C_2H_5$O | $C_2H_5$O | | |
| 450 | n-$C_3H_7$O | n-$C_3H_7$O | | |

Note:
*values extrapolated from 10% solution in ZLI-4792.

Examples 451 to 480

The following are prepared analogously to Example 241 and Example 361a:

in which

―⬡― is ―⬡― and $Z^1$ is ―CF=CF―.

| No. | $R^1$ | $R^2$ | Phase sequence T/° C. | Δε* |
|---|---|---|---|---|
| 451 | $CH_3$ | $CH_3$ | | |
| 452 | $CH_3$ | $C_2H_5$ | | |

-continued

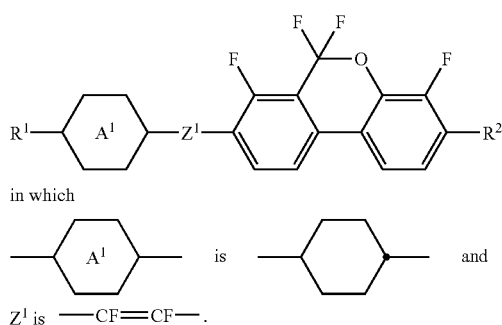

in which

─⟨A¹⟩─ is ─⟨cyclohexyl⟩─ and $Z^1$ is ─CF═CF─.

| No. | R¹ | R² | Phase sequence T/° C. | Δε* |
|---|---|---|---|---|
| 453 | CH₃ | n-C₃H₇ | | |
| 454 | C₂H₅ | CH₃ | | |
| 455 | C₂H₅ | C₂H₅ | | |
| 456 | C₂H₅ | n-C₃H₇ | | |
| 457 | n-C₃H₇ | CH₃ | | |
| 458 | n-C₃H₇ | C₂H₅ | | |
| 459 | n-C₃H₇ | n-C₃H₇ | | |
| 460 | n-C₃H₇ | n-C₅H₁₁ | | |
| 461 | n-C₅H₁₁ | n-C₃H₇ | | |
| 462 | n-C₅H₁₁ | n-C₅H₁₁ | | |
| 463 | CH₂═CH | CH₃ | | |
| 464 | CH₂═CH | C₂H₅ | | |
| 465 | CH₂═CH | n-C₃H₇ | | |
| 466 | CH₂═CH | CH₂═CH | | |
| 467 | CH₃ | CH₂═CH | | |
| 468 | C₂H₅ | CH₂═CH | | |
| 469 | n-C₃H₇ | CH₂═CH | | |
| 470 | E-CH₃─CH═CH | CH₂═CH | | |
| 471 | E-CH₃─CH═CH | E-CH₃─CH═CH | | |
| 472 | CH₃ | CH₃O | | |
| 473 | CH₃ | C₂H₅O | | |
| 474 | CH₃ | n-C₃H₇O | | |
| 475 | n-C₃H₇ | CH₃O | | |
| 476 | n-C₃H₇ | C₂H₅O | | |
| 477a | n-C₃H₇ | n-C₃H₇O | | |
| 477b | n-C₅H₁₁ | n-C₄H₉O | | |
| 477c | n-C₄H₉O | n-C₅H₁₁ | | |
| 478 | CH₃O | CH₃O | | |
| 479 | C₂H₅O | C₂H₅O | | |
| 480 | n-C₃H₇O | n-C₃H₇O | | |

Note:
*values extrapolated from 10% solution in ZLI-4792 or ZLI-2857 (Δε).

Examples 481 to 510

The following are prepared analogously to Example 241 and Example 361a:

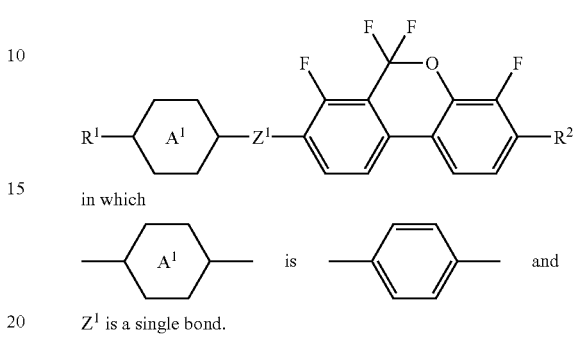

in which

─⟨A¹⟩─ is ─⟨phenyl⟩─ and $Z^1$ is a single bond.

| No. | R¹ | R² | Phase sequence T/° C. | Δε* |
|---|---|---|---|---|
| 481 | CH₃ | CH₃ | | |
| 482 | CH₃ | C₂H₅ | | |
| 483 | CH₃ | n-C₃H₇ | | |
| 484 | C₂H₅ | CH₃ | | |
| 485 | C₂H₅ | C₂H₅ | | |
| 486 | C₂H₅ | n-C₃H₇ | | |
| 487 | n-C₃H₇ | CH₃ | | |
| 488 | n-C₃H₇ | C₂H₅ | | |
| 489 | n-C₃H₇ | n-C₃H₇ | | |
| 490 | n-C₃H₇ | n-C₅H₁₁ | | |
| 491 | n-C₅H₁₁ | n-C₃H₇ | | |
| 492 | n-C₅H₁₁ | n-C₅H₁₁ | | |
| 493 | CH₂═CH | CH₃ | | |
| 494 | CH₂═CH | C₂H₅ | | |
| 495 | CH₂═CH | n-C₃H₇ | | |
| 496 | CH₂═CH | CH₂═CH | | |
| 497 | CH₃ | CH₂═CH | | |
| 498 | C₂H₅ | CH₂═CH | | |
| 499 | n-C₃H₇ | CH₂═CH | | |
| 500 | E-CH₃─CH═CH | CH₂═CH | | |
| 501 | E-CH₃─CH═CH | E-CH₃─CH═CH | | |
| 502 | CH₃ | CH₃O | | |
| 503 | CH₃ | C₂H₅O | | |
| 504 | CH₃ | n-C₃H₇O | | |
| 505 | n-C₃H₇ | CH₃O | | |
| 506 | n-C₃H₇ | C₂H₅O | | |
| 507a | n-C₃H₇ | n-C₃H₇O | | |
| 507b | n-C₅H₁₁ | n-C₄H₉O | | |
| 507c | n-C₄H₉O | n-C₅H₁₁ | | |
| 508 | CH₃O | CH₃O | | |
| 509 | C₂H₅O | C₂H₅O | | |
| 510 | n-C₃H₇O | n-C₃H₇O | | |

Note:
*values extrapolated from 10% solution in ZLI-4792 or ZLI-2857 (Δε).

Examples 511 to 540

The following are prepared analogously to Example 241 and Example 361a:

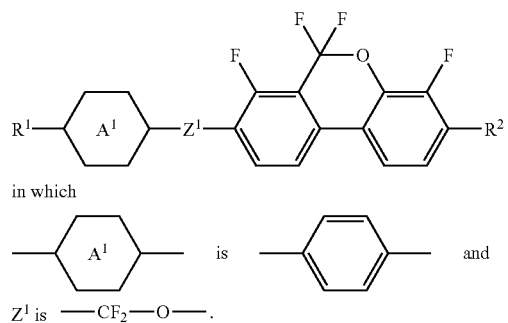

in which

—A¹— is —⌬— and

Z¹ is —CF₂—O—.

| No. | R¹ | R² | Phase sequence T/° C. | Δε* |
|---|---|---|---|---|
| 511 | CH₃ | CH₃ | | |
| 512 | CH₃ | C₂H₅ | | |
| 513 | CH₃ | n-C₃H₇ | | |
| 514 | C₂H₅ | CH₃ | | |
| 515 | C₂H₅ | C₂H₅ | | |
| 516 | C₂H₅ | n-C₃H₇ | | |
| 517 | n-C₃H₇ | CH₃ | | |
| 518 | n-C₃H₇ | C₂H₅ | | |
| 519 | n-C₃H₇ | n-C₃H₇ | | |
| 520 | n-C₃H₇ | n-C₅H₁₁ | | |
| 521 | n-C₅H₁₁ | n-C₃H₇ | | |
| 522 | n-C₅H₁₁ | n-C₅H₁₁ | | |
| 523 | CH₂=CH | CH₃ | | |
| 524 | CH₂=CH | C₂H₅ | | |
| 525 | CH₂=CH | n-C₃H₇ | | |
| 526 | CH₂=CH | CH₂=CH | | |
| 527 | CH₃ | CH₂=CH | | |
| 528 | C₂H₅ | CH₂=CH | | |
| 529 | n-C₃H₇ | CH₂=CH | | |
| 530 | E-CH₃—CH=CH | CH₂=CH | | |
| 531 | E-CH₃—CH=CH | E-CH₃—CH=CH | | |
| 532 | CH₃ | CH₃O | | |
| 533 | CH₃ | C₂H₅O | | |
| 534 | CH₃ | n-C₃H₇O | | |
| 535 | n-C₃H₇ | CH₃O | | |
| 536 | n-C₃H₇ | C₂H₅O | | |
| 537a | n-C₃H₇ | n-C₃H₇O | | |
| 537b | n-C₅H₁₁ | n-C₄H₉O | | |
| 537c | n-C₄H₉O | n-C₅H₁₁ | | |
| 538 | CH₃O | CH₃O | | |
| 539 | C₂H₅O | C₂H₅O | | |
| 540 | n-C₃H₇O | n-C₃H₇O | | |

Note:
*values extrapolated from 10% solution in ZLI-4792 or ZLI-2857 (Δε).

Examples 541 to 570

The following are prepared analogously to Example 241 and Example 361a:

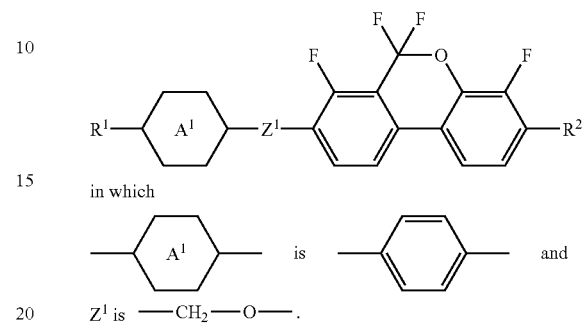

in which

—A¹— is —⌬— and

Z¹ is —CH₂—O—.

| No. | R¹ | R² | Phase sequence T/° C. | Δε* |
|---|---|---|---|---|
| 541 | CH₃ | CH₃ | | |
| 542 | CH₃ | C₂H₅ | | |
| 543 | CH₃ | n-C₃H₇ | | |
| 544 | C₂H₅ | CH₃ | | |
| 545 | C₂H₅ | C₂H₅ | | |
| 546 | C₂H₅ | n-C₃H₇ | | |
| 547 | n-C₃H₇ | CH₃ | | |
| 548 | n-C₃H₇ | C₂H₅ | | |
| 549 | n-C₃H₇ | n-C₃H₇ | | |
| 550 | n-C₃H₇ | n-C₅H₁₁ | | |
| 551 | n-C₅H₁₁ | n-C₃H₇ | | |
| 552 | n-C₅H₁₁ | n-C₅H₁₁ | | |
| 553 | CH₂=CH | CH₃ | | |
| 554 | CH₂=CH | C₂H₅ | | |
| 555 | CH₂=CH | n-C₃H₇ | | |
| 556 | CH₂=CH | CH₂=CH | | |
| 557 | CH₃ | CH₂=CH | | |
| 558 | C₂H₅ | CH₂=CH | | |
| 559 | n-C₃H₇ | CH₂=CH | | |
| 560 | E-CH₃—CH=CH | CH₂=CH | | |
| 561 | E-CH₃—CH=CH | E-CH₃—CH=CH | | |
| 562 | CH₃ | CH₃O | | |
| 563 | CH₃ | C₂H₅O | | |
| 564 | CH₃ | n-C₃H₇O | | |
| 565 | n-C₃H₇ | CH₃O | | |
| 566 | n-C₃H₇ | C₂H₅O | | |
| 567a | n-C₃H₇ | n-C₃H₇O | | |
| 567b | n-C₅H₁₁ | n-C₄H₉O | | |
| 567c | n-C₄H₉O | n-C₅H₁₁ | | |
| 568 | CH₃O | CH₃O | | |
| 569 | C₂H₅O | C₂H₅O | | |
| 570 | n-C₃H₇O | n-C₃H₇O | | |

Note:
*values extrapolated from 10% solution in ZLI-4792 or ZLI-2857 (Δε).

Examples 571 to 600

The following are prepared analogously to Example 241 and Example 361a:

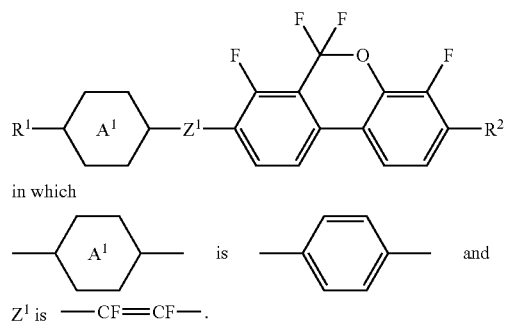

in which

—A¹— is —⟨phenyl⟩— and

Z¹ is —CF=CF—.

| No. | R¹ | R² | Phase sequence T/° C. | Δε* |
|---|---|---|---|---|
| 571 | CH₃ | CH₃ | | |
| 572 | CH₃ | C₂H₅ | | |
| 573 | CH₃ | n-C₃H₇ | | |
| 574 | C₂H₅ | CH₃ | | |
| 575 | C₂H₅ | C₂H₅ | | |
| 576 | C₂H₅ | n-C₃H₇ | | |
| 577 | n-C₃H₇ | CH₃ | | |
| 578 | n-C₃H₇ | C₂H₅ | | |
| 579 | n-C₃H₇ | n-C₃H₇ | | |
| 580 | n-C₃H₇ | n-C₅H₁₁ | | |
| 581 | n-C₅H₁₁ | n-C₃H₇ | | |
| 582 | n-C₅H₁₁ | n-C₅H₁₁ | | |
| 583 | CH₂=CH | CH₃ | | |
| 584 | CH₂=CH | C₂H₅ | | |
| 585 | CH₂=CH | n-C₃H₇ | | |
| 586 | CH₂=CH | CH₂=CH | | |
| 587 | CH₃ | CH₂=CH | | |
| 588 | C₂H₅ | CH₂=CH | | |
| 589 | n-C₃H₇ | CH₂=CH | | |
| 590 | E-CH₃—CH=CH | CH₂=CH | | |
| 591 | E-CH₃—CH=CH | E-CH₃—CH=CH | | |
| 592 | CH₃ | CH₃O | | |
| 593 | CH₃ | C₂H₅O | | |
| 594 | CH₃ | n-C₃H₇O | | |
| 595 | n-C₃H₇ | CH₃O | | |
| 596 | n-C₃H₇ | C₂H₅O | | |
| 597a | n-C₃H₇ | n-C₃H₇O | | |
| 597b | n-C₅H₁₁ | n-C₄H₉O | | |
| 597c | n-C₄H₉O | n-C₅H₁₁ | | |
| 598 | CH₃O | CH₃O | | |
| 599 | C₂H₅O | C₂H₅O | | |
| 600 | n-C₃H₇O | n-C₃H₇O | | |

Note:
*values extrapolated from 10% solution in ZLI-4792 or ZLI-2857 (Δε).

Examples 601 to 630

The following are prepared analogously to Example 241 and Example 361a:

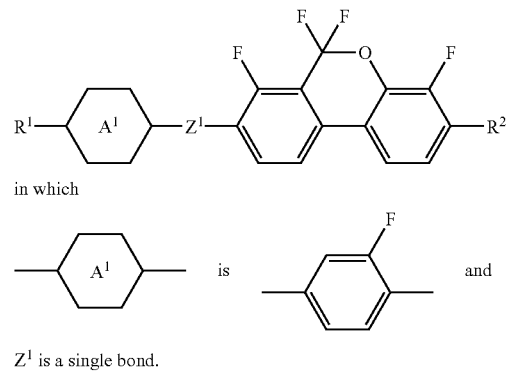

in which

—A¹— is —⟨fluorophenyl⟩— and

Z¹ is a single bond.

| No. | R¹ | R² | Phase sequence T/° C. | Δε* |
|---|---|---|---|---|
| 601 | CH₃ | CH₃ | | |
| 602 | CH₃ | C₂H₅ | | |
| 603 | CH₃ | n-C₃H₇ | | |
| 604 | C₂H₅ | CH₃ | | |
| 605 | C₂H₅ | C₂H₅ | | |
| 606 | C₂H₅ | n-C₃H₇ | | |
| 607 | n-C₃H₇ | CH₃ | | |
| 608 | n-C₃H₇ | C₂H₅ | | |
| 609 | n-C₃H₇ | n-C₃H₇ | | |
| 610 | n-C₃H₇ | n-C₅H₁₁ | | |
| 611 | n-C₅H₁₁ | n-C₃H₇ | | |
| 612 | n-C₅H₁₁ | n-C₅H₁₁ | | |
| 613 | CH₂=CH | CH₃ | | |
| 614 | CH₂=CH | C₂H₅ | | |
| 615 | CH₂=CH | n-C₃H₇ | | |
| 616 | CH₂=CH | CH₂=CH | | |
| 617 | CH₃ | CH₂=CH | | |
| 618 | C₂H₅ | CH₂=CH | | |
| 619 | n-C₃H₇ | CH₂=CH | | |
| 620 | E-CH₃—CH=CH | CH₂=CH | | |
| 621 | E-CH₃—CH=CH | E-CH₃—CH=CH | | |
| 622 | CH₃ | CH₃O | | |
| 623 | CH₃ | C₂H₅O | | |
| 624 | CH₃ | n-C₃H₇O | | |
| 625 | n-C₃H₇ | CH₃O | | |
| 626 | n-C₃H₇ | C₂H₅O | | |
| 627a | n-C₃H₇ | n-C₃H₇O | | |
| 627b | n-C₅H₁₁ | n-C₄H₉O | | |
| 527c | n-C₄H₉O | n-C₅H₁₁ | | |
| 628 | CH₃O | CH₃O | | |
| 629 | C₂H₅O | C₂H₅O | | |
| 630 | n-C₃H₇O | n-C₃H₇O | | |

Note:
*values extrapolated from 10% solution in ZLI-4792 or ZLI-2857 (Δε).

105

Examples 631 to 660

The following are prepared analogously to Example 241 and Example 361a:

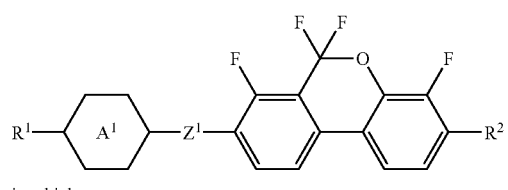

in which

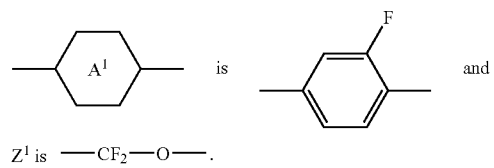 is <chemical structure> and $Z^1$ is —CF$_2$—O—.

| No. | R$^1$ | R$^2$ | Phase sequence T/° C. | Δε* |
|-----|-------|-------|------------------------|-----|
| 631 | CH$_3$ | CH$_3$ | | |
| 632 | CH$_3$ | C$_2$H$_5$ | | |
| 633 | CH$_3$ | n-C$_3$H$_7$ | | |
| 634 | C$_2$H$_5$ | CH$_3$ | | |
| 635 | C$_2$H$_5$ | C$_2$H$_5$ | | |
| 636 | C$_2$H$_5$ | n-C$_3$H$_7$ | | |
| 637 | n-C$_3$H$_7$ | CH$_3$ | | |
| 638 | n-C$_3$H$_7$ | C$_2$H$_5$ | | |
| 639 | n-C$_3$H$_7$ | n-C$_3$H$_7$ | | |
| 640 | n-C$_3$H$_7$ | n-C$_5$H$_{11}$ | | |
| 641 | n-C$_5$H$_{11}$ | n-C$_3$H$_7$ | | |
| 642 | n-C$_5$H$_{11}$ | n-C$_5$H$_{11}$ | | |
| 643 | CH$_2$=CH | CH$_3$ | | |
| 644 | CH$_2$=CH | C$_2$H$_5$ | | |
| 645 | CH$_2$=CH | n-C$_3$H$_7$ | | |
| 646 | CH$_2$=CH | CH$_2$=CH | | |
| 677 | CH$_3$ | CH$_2$=CH | | |
| 648 | C$_2$H$_5$ | CH$_2$=CH | | |
| 649 | n-C$_3$H$_7$ | CH$_2$=CH | | |
| 650 | E-CH$_3$—CH=CH | CH$_2$=CH | | |
| 651 | E-CH$_3$—CH=CH | E-CH$_3$—CH=CH | | |
| 652 | CH$_3$ | CH$_3$O | | |
| 653 | CH$_3$ | C$_2$H$_5$O | | |
| 654 | CH$_3$ | n-C$_3$H$_7$O | | |
| 655 | n-C$_3$H$_7$ | CH$_3$O | | |
| 656 | n-C$_3$H$_7$ | C$_2$H$_5$O | | |
| 657a | n-C$_3$H$_7$ | n-C$_3$H$_7$O | | |
| 657b | n-C$_5$H$_{11}$ | n-C$_4$H$_9$O | | |
| 5617c | n-C$_4$H$_9$O | n-C$_5$H$_{11}$ | | |
| 658 | CH$_3$O | CH$_3$O | | |
| 659 | C$_2$H$_5$O | C$_2$H$_5$O | | |
| 660 | n-C$_3$H$_7$O | n-C$_3$H$_7$O | | |

Note:
*values extrapolated from 10% solution in ZLI-4792 or ZLI-2857 (Δε).

106

Examples 661 to 690

The following are prepared analogously to Example 241 and Example 361a:

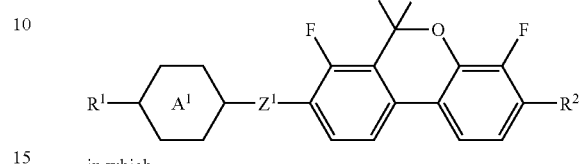

in which

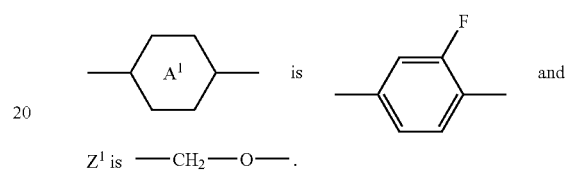 is <chemical structure> and $Z^1$ is —CH$_2$—O—.

| No. | R$^1$ | R$^2$ | Phase sequence T/° C. | Δε* |
|-----|-------|-------|------------------------|-----|
| 661 | CH$_3$ | CH$_3$ | | |
| 662 | CH$_3$ | C$_2$H$_5$ | | |
| 663 | CH$_3$ | n-C$_3$H$_7$ | | |
| 664 | C$_2$H$_5$ | CH$_3$ | | |
| 665 | C$_2$H$_5$ | C$_2$H$_5$ | | |
| 666 | C$_2$H$_5$ | n-C$_3$H$_7$ | | |
| 667 | n-C$_3$H$_7$ | CH$_3$ | | |
| 668 | n-C$_3$H$_7$ | C$_2$H$_5$ | | |
| 669 | n-C$_3$H$_7$ | n-C$_3$H$_7$ | | |
| 670 | n-C$_3$H$_7$ | n-C$_5$H$_{11}$ | | |
| 671 | n-C$_5$H$_{11}$ | n-C$_3$H$_7$ | | |
| 672 | n-C$_5$H$_{11}$ | n-C$_5$H$_{11}$ | | |
| 673 | CH$_2$=CH | CH$_3$ | | |
| 674 | CH$_2$=CH | C$_2$H$_5$ | | |
| 675 | CH$_2$=CH | n-C$_3$H$_7$ | | |
| 676 | CH$_2$=CH | CH$_2$=CH | | |
| 677 | CH$_3$ | CH$_2$=CH | | |
| 678 | C$_2$H$_5$ | CH$_2$=CH | | |
| 679 | n-C$_3$H$_7$ | CH$_2$=CH | | |
| 680 | E-CH$_3$—CH=CH | CH$_2$=CH | | |
| 681 | E-CH$_3$—CH=CH | E-CH$_3$—CH=CH | | |
| 682 | CH$_3$ | CH$_3$O | | |
| 683 | CH$_3$ | C$_2$H$_5$O | | |
| 684 | CH$_3$ | n-C$_3$H$_7$O | | |
| 685 | n-C$_3$H$_7$ | CH$_3$O | | |
| 686 | n-C$_3$H$_7$ | C$_2$H$_5$O | | |
| 687a | n-C$_3$H$_7$ | n-C$_3$H$_7$O | | |
| 687b | n-C$_5$H$_{11}$ | n-C$_4$H$_9$O | | |
| 687c | n-C$_4$H$_9$O | n-C$_5$H$_{11}$ | | |
| 688 | CH$_3$O | CH$_3$O | | |
| 689 | C$_2$H$_5$O | C$_2$H$_5$O | | |
| 690 | n-C$_3$H$_7$O | n-C$_3$H$_7$O | | |

Note:
*values extrapolated from 10% solution in ZLI-4792 or ZLI-2857 (Δε).

Examples 691 to 720

The following are prepared analogously to Example 241 and Example 361a:

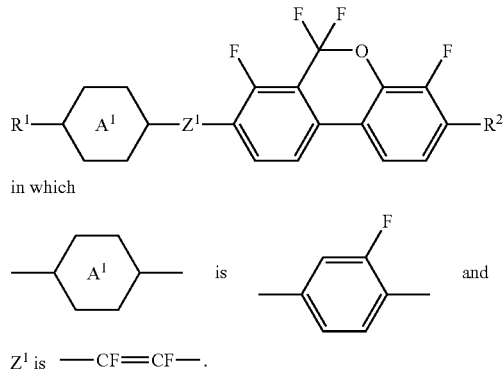

in which

—A¹— is (2-fluoro-1,4-phenylene) and

Z¹ is —CF=CF—.

| No. | R¹ | R² | Phase sequence T/° C. | Δε* |
|---|---|---|---|---|
| 691 | CH₃ | CH₃ | | |
| 692 | CH₃ | C₂H₅ | | |
| 693 | CH₃ | n-C₃H₇ | | |
| 694 | C₂H₅ | CH₃ | | |
| 695 | C₂H₅ | C₂H₅ | | |
| 696 | C₂H₅ | n-C₃H₇ | | |
| 697 | n-C₃H₇ | CH₃ | | |
| 698 | n-C₃H₇ | C₂H₅ | | |
| 699 | n-C₃H₇ | n-C₃H₇ | | |
| 700 | n-C₃H₇ | n-C₅H₁₁ | | |
| 701 | n-C₅H₁₁ | n-C₃H₇ | | |
| 702 | n-C₅H₁₁ | n-C₅H₁₁ | | |
| 703 | CH₂=CH | CH₃ | | |
| 704 | CH₂=CH | C₂H₅ | | |
| 705 | CH₂=CH | n-C₃H₇ | | |
| 706 | CH₂=CH | CH₂=CH | | |
| 707 | CH₃ | CH₂=CH | | |
| 708 | C₂H₅ | CH₂=CH | | |
| 709 | n-C₃H₇ | CH₂=CH | | |
| 710 | E-CH₃—CH=CH | CH₂=CH | | |
| 711 | E-CH₃—CH=CH | E-CH₃—CH=CH | | |
| 712 | CH₃ | CH₃O | | |
| 713 | CH₃ | C₂H₅O | | |
| 714 | CH₃ | n-C₃H₇O | | |
| 715 | n-C₃H₇ | CH₃O | | |
| 716 | n-C₃H₇ | C₂H₅O | | |
| 717a | n-C₃H₇ | n-C₃H₇O | | |
| 717b | n-C₅H₁₁ | n-C₄H₉O | | |
| 717c | n-C₄H₉O | n-C₅H₁₁ | | |
| 718 | CH₃O | CH₃O | | |
| 719 | C₂H₅O | C₂H₅O | | |
| 720 | n-C₃H₇O | n-C₃H₇O | | |

Note:
*values extrapolated from 10% solution in ZLI-4792 or ZLI-2857 (Δε).

Examples 721 to 750

The following are prepared analogously to Example 241 and Example 361a:

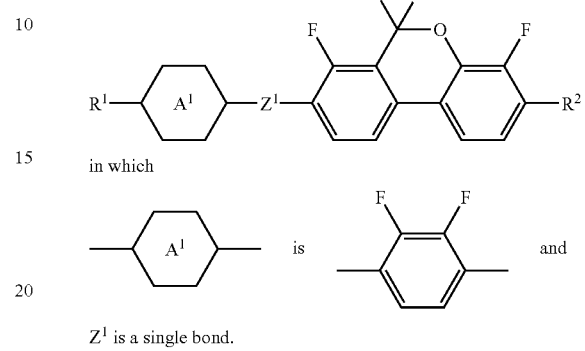

in which

—A¹— is (2,3-difluoro-1,4-phenylene) and

Z¹ is a single bond.

| No. | R¹ | R² | Phase sequence T/° C. | Δε* |
|---|---|---|---|---|
| 721 | CH₃ | CH₃ | | |
| 722 | CH₃ | C₂H₅ | | |
| 723 | CH₃ | n-C₃H₇ | | |
| 724 | C₂H₅ | CH₃ | | |
| 725 | C₂H₅ | C₂H₅ | | |
| 726 | C₂H₅ | n-C₃H₇ | | |
| 727 | n-C₃H₇ | CH₃ | | |
| 728 | n-C₃H₇ | C₂H₅ | | |
| 729 | n-C₃H₇ | n-C₃H₇ | | |
| 730 | n-C₃H₇ | n-C₅H₁₁ | | |
| 731 | n-C₅H₁₁ | n-C₃H₇ | | |
| 732 | n-C₅H₁₁ | n-C₅H₁₁ | | |
| 733 | CH₂=CH | CH₃ | | |
| 734 | CH₂=CH | C₂H₅ | | |
| 735 | CH₂=CH | n-C₃H₇ | | |
| 736 | CH₂=CH | CH₂=CH | | |
| 737 | CH₃ | CH₂=CH | | |
| 738 | C₂H₅ | CH₂=CH | | |
| 739 | n-C₃H₇ | CH₂=CH | | |
| 740 | E-CH₃—CH=CH | CH₂=CH | | |
| 741 | E-CH₃—CH=CH | E-CH₃—CH=CH | | |
| 742 | CH₃ | CH₃O | | |
| 743 | CH₃ | C₂H₅O | | |
| 744 | CH₃ | n-C₃H₇O | | |
| 745 | n-C₃H₇ | CH₃O | | |
| 746 | n-C₃H₇ | C₂H₅O | | |
| 747a | n-C₃H₇ | n-C₃H₇O | | |
| 747b | n-C₅H₁₁ | n-C₄H₉O | | |
| 747c | n-C₄H₉O | n-C₅H₁₁ | | |
| 748 | CH₃O | CH₃O | | |
| 749 | C₂H₅O | C₂H₅O | | |
| 750 | n-C₃H₇O | n-C₃H₇O | | |

Note:
*values extrapolated from 10% solution in ZLI-4792 or ZLI-2857 (Δε).

Examples 751 to 780

The following are prepared analogously to Example 241 and Example 361a:

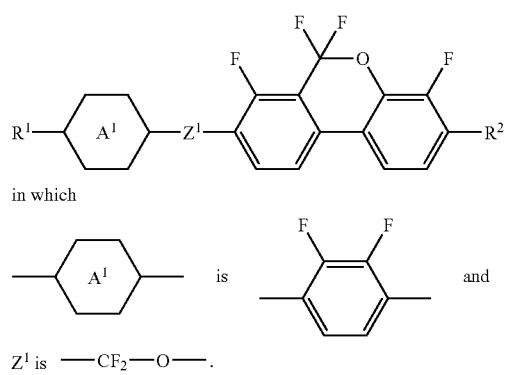

in which $A^1$ is [2,3-difluoro-1,4-phenylene] and $Z^1$ is —CF$_2$—O—.

| No. | R$^1$ | R$^2$ | Phase sequence T/° C. | Δε* |
|---|---|---|---|---|
| 751 | CH$_3$ | CH$_3$ | | |
| 752 | CH$_3$ | C$_2$H$_5$ | | |
| 753 | CH$_3$ | n-C$_3$H$_7$ | | |
| 754 | C$_2$H$_5$ | CH$_3$ | | |
| 755 | C$_2$H$_5$ | C$_2$H$_5$ | | |
| 756 | C$_2$H$_5$ | n-C$_3$H$_7$ | | |
| 757 | n-C$_3$H$_7$ | CH$_3$ | | |
| 758 | n-C$_3$H$_7$ | C$_2$H$_5$ | | |
| 759 | n-C$_3$H$_7$ | n-C$_3$H$_7$ | | |
| 760 | n-C$_3$H$_7$ | n-C$_5$H$_{11}$ | | |
| 761 | n-C$_5$H$_{11}$ | n-C$_3$H$_7$ | | |
| 762 | n-C$_5$H$_{11}$ | n-C$_5$H$_{11}$ | | |
| 763 | CH$_2$=CH | CH$_3$ | | |
| 764 | CH$_2$=CH | C$_2$H$_5$ | | |
| 765 | CH$_2$=CH | n-C$_3$H$_7$ | | |
| 766 | CH$_2$=CH | CH$_2$=CH | | |
| 767 | CH$_3$ | CH$_2$=CH | | |
| 768 | C$_2$H$_5$ | CH$_2$=CH | | |
| 769 | n-C$_3$H$_7$ | CH$_2$=CH | | |
| 770 | E-CH$_3$—CH=CH | CH$_2$=CH | | |
| 771 | E-CH$_3$—CH=CH | E-CH$_3$—CH=CH | | |
| 772 | CH$_3$ | CH$_3$O | | |
| 773 | CH$_3$ | C$_2$H$_5$O | | |
| 774 | CH$_3$ | n-C$_3$H$_7$O | | |
| 775 | n-C$_3$H$_7$ | CH$_3$O | | |
| 776 | n-C$_3$H$_7$ | C$_2$H$_5$O | | |
| 777a | n-C$_3$H$_7$ | n-C$_3$H$_7$O | | |
| 777b | n-C$_5$H$_{11}$ | n-C$_4$H$_9$O | | |
| 777c | n-C$_4$H$_9$O | n-C$_5$H$_{11}$ | | |
| 778 | CH$_3$O | CH$_3$O | | |
| 779 | C$_2$H$_5$O | C$_2$H$_5$O | | |
| 780 | n-C$_3$H$_7$O | n-C$_3$H$_7$O | | |

Note:
*values extrapolated from 10% solution in ZLI-4792 or ZLI-2857 (Δε).

Examples 781 to 810

The following are prepared analogously to Example 241 and Example 361a:

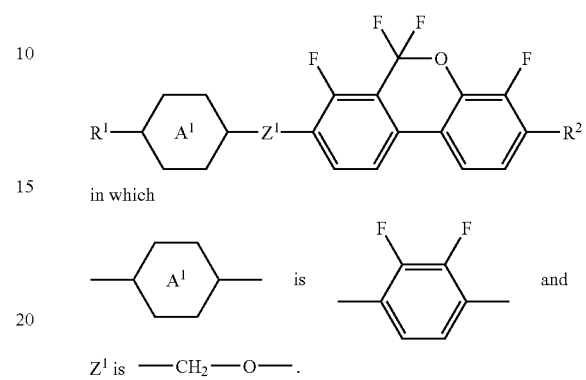

in which $A^1$ is [2,3-difluoro-1,4-phenylene] and $Z^1$ is —CH$_2$—O—.

| No. | R$^1$ | R$^2$ | Phase sequence T/° C. | Δε* |
|---|---|---|---|---|
| 781 | CH$_3$ | CH$_3$ | | |
| 782 | CH$_3$ | C$_2$H$_5$ | | |
| 783 | CH$_3$ | n-C$_3$H$_7$ | | |
| 784 | C$_2$H$_5$ | CH$_3$ | | |
| 785 | C$_2$H$_5$ | C$_2$H$_5$ | | |
| 786 | C$_2$H$_5$ | n-C$_3$H$_7$ | | |
| 787 | n-C$_3$H$_7$ | CH$_3$ | | |
| 788 | n-C$_3$H$_7$ | C$_2$H$_5$ | | |
| 789 | n-C$_3$H$_7$ | n-C$_3$H$_7$ | | |
| 790 | n-C$_3$H$_7$ | n-C$_5$H$_{11}$ | | |
| 791 | n-C$_5$H$_{11}$ | n-C$_3$H$_7$ | | |
| 792 | n-C$_5$H$_{11}$ | n-C$_5$H$_{11}$ | | |
| 793 | CH$_2$=CH | CH$_3$ | | |
| 794 | CH$_2$=CH | C$_2$H$_5$ | | |
| 795 | CH$_2$=CH | n-C$_3$H$_7$ | | |
| 796 | CH$_2$=CH | CH$_2$=CH | | |
| 797 | CH$_3$ | CH$_2$=CH | | |
| 798 | C$_2$H$_5$ | CH$_2$=CH | | |
| 799 | n-C$_3$H$_7$ | CH$_2$=CH | | |
| 800 | E-CH$_3$—CH=CH | CH$_2$=CH | | |
| 801 | E-CH$_3$—CH=CH | E-CH$_3$—CH=CH | | |
| 802 | CH$_3$ | CH$_3$O | | |
| 803 | CH$_3$ | C$_2$H$_5$O | | |
| 804 | CH$_3$ | n-C$_3$H$_7$O | | |
| 805 | n-C$_3$H$_7$ | CH$_3$O | | |
| 806 | n-C$_3$H$_7$ | C$_2$H$_5$O | | |
| 807a | n-C$_3$H$_7$ | n-C$_3$H$_7$O | | |
| 807b | n-C$_5$H$_{11}$ | n-C$_4$H$_9$O | | |
| 807c | n-C$_4$H$_9$O | n-C$_5$H$_{11}$ | | |
| 808 | CH$_3$O | CH$_3$O | | |
| 809 | C$_2$H$_5$O | C$_2$H$_5$O | | |
| 810 | n-C$_3$H$_7$O | n-C$_3$H$_7$O | | |

Note:
*values extrapolated from 10% solution in ZLI-4792 or ZLI-2857 (Δε).

Examples 811 to 840

The following are prepared analogously to Example 241 and Example 361a:

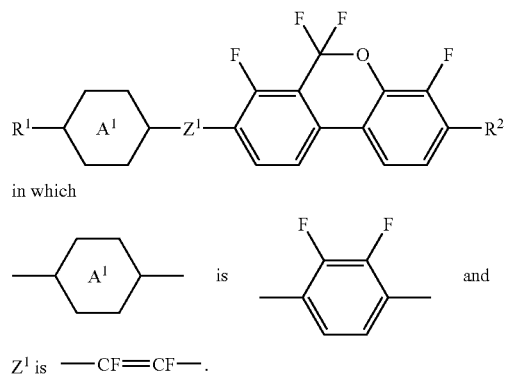

in which

—A¹— is 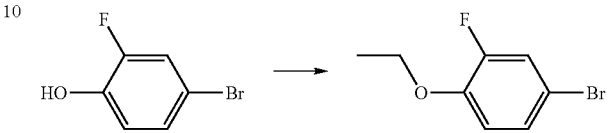 and

Z¹ is —CF=CF—.

| No. | R¹ | R² | Phase sequence T/° C. | Δε* |
|---|---|---|---|---|
| 811 | CH₃ | CH₃ | | |
| 812 | CH₃ | C₂H₅ | | |
| 813 | CH₃ | n-C₃H₇ | | |
| 814 | C₂H₅ | CH₃ | | |
| 815 | C₂H₅ | C₂H₅ | | |
| 816 | C₂H₅ | n-C₃H₇ | | |
| 817 | n-C₃H₇ | CH₃ | | |
| 818 | n-C₃H₇ | C₂H₅ | | |
| 819 | n-C₃H₇ | n-C₃H₇ | | |
| 820 | n-C₃H₇ | n-C₅H₁₁ | | |
| 821 | n-C₅H₁₁ | n-C₃H₇ | | |
| 822 | n-C₅H₁₁ | n-C₅H₁₁ | | |
| 823 | CH₂=CH | CH₃ | | |
| 824 | CH₂=CH | C₂H₅ | | |
| 825 | CH₂=CH | n-C₃H₇ | | |
| 826 | CH₂=CH | CH₂=CH | | |
| 827 | CH₃ | CH₂=CH | | |
| 828 | C₂H₅ | CH₂=CH | | |
| 829 | n-C₃H₇ | CH₂=CH | | |
| 830 | E-CH₃—CH=CH | CH₂=CH | | |
| 831 | E-CH₃—CH=CH | E-CH₃—CH=CH | | |
| 832 | CH₃ | CH₃O | | |
| 833 | CH₃ | C₂H₅O | | |
| 834 | CH₃ | n-C₃H₇O | | |
| 835 | n-C₃H₇ | CH₃O | | |
| 836 | n-C₃H₇ | C₂H₅O | | |
| 837a | n-C₃H₇ | n-C₃H₇O | | |
| 837b | n-C₅H₁₁ | n-C₄H₉O | | |
| 837c | n-C₄H₉O | n-C₅H₁₁ | | |
| 838 | CH₃O | CH₃O | | |
| 839 | C₂H₅O | C₂H₅O | | |
| 840 | n-C₃H₇O | n-C₃H₇O | | |

Note:
*values extrapolated from 10% solution in ZLI-4792 or ZLI-2857 (Δε).

Example 841

(8-Ethoxy-4,7-difluoro-3-benzyloxybenzo[c]chromen-6-one)

841.1 Preparation of 4-bromo-1-ethoxy-2-fluorobenzene

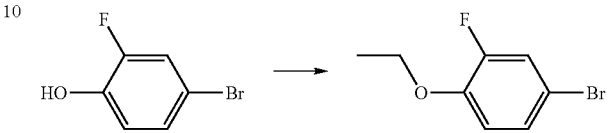

100 g (0.524 mol) of 4-bromo-2-fluorophenol and 66.7 g (0.612 mol) of ethyl bromide were dissolved in 2 l of ethyl methyl ketone and refluxed for 24 hours in the presence of 185 g (1.34 mol) of potassium carbonate. The solution was subsequently filtered, the filtrate was evaporated, and the crude product was filtered through silica gel with n-hexane, giving 114 g (99% of theory) of 4-bromo-1-ethoxy-2-fluorobenzene as a colourless liquid.

841.2 Preparation of 6-bromo-3-ethoxy-2-fluorobenzoic acid

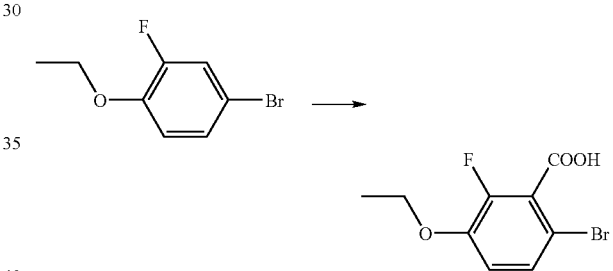

Analogously to the synthesis described above (under Example 1.3), 236 g of 4-bromo-1-ethoxy-2-fluorobenzene gave 190 g (64% of theory) of 6-bromo-3-ethoxy-2-fluorobenzoic acid as colourless crystals.

841.3 Preparation of 1-benzyloxy-4-bromo-2-fluorobenzene

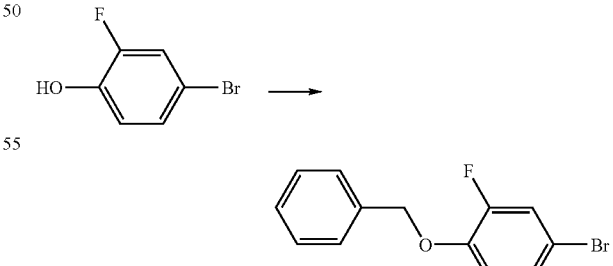

Analogously to the synthesis described above (under Example 2.1 or 872.1), 250 g (1.31 mol) of 4-bromo-2-fluorophenol and 179 ml (1.51 mol) of benzyl bromide gave 366 g (97%) of 1-benzyloxy-4-bromo-2-fluorobenzene as colourless crystals.

841.4 Preparation of 3-benzyloxy-6-bromo-2-fluorophenol

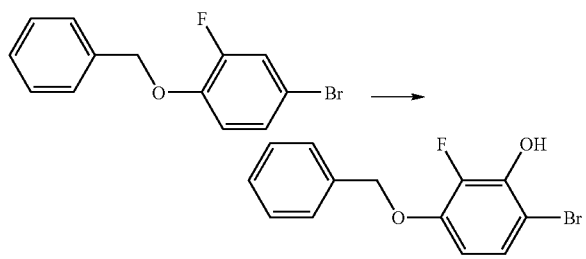

Analogously to the synthesis described above (under Example 1.2), 366 g (1.27 mol) of 1-benzyloxy-4-bromo-2-fluorobenzene give 270 g (72% of theory) of 3-benzyloxy-6-bromo-2-fluorophenol as colourless crystals.

841.5 Preparation of 3-benzyloxy-6-bromo-2-fluorophenyl 6-bromo-3-ethoxy-2-fluorobenzoate

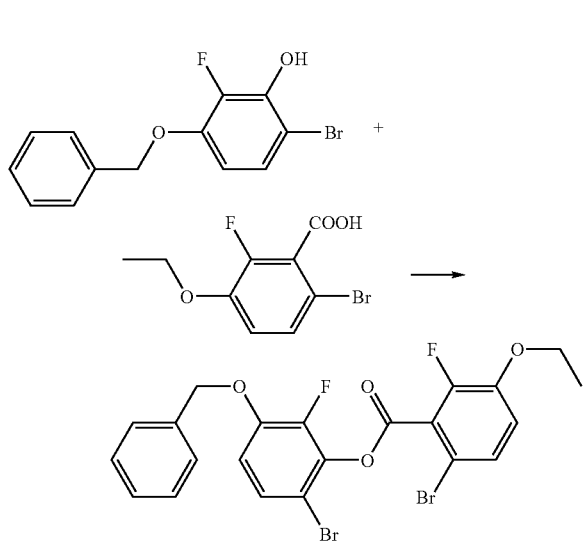

Analogously to the synthesis described above (under Example 1.4), 253 g (0.851 mol) of 3-benzyloxy-6-bromo-2-fluorophenol and 246 g (0.936 mol) of 6-bromo-3-ethoxy-2-fluorobenzoic acid give 405 g (87% of theory) of 3-benzyloxy-6-bromo-2-fluorophenyl 6-bromo-3-ethoxy-2-fluorobenzoate as colourless crystals.

841.6 Preparation of 8-ethoxy-4,7-difluoro-3-benzyloxy-benzo[c]chromen-6-one

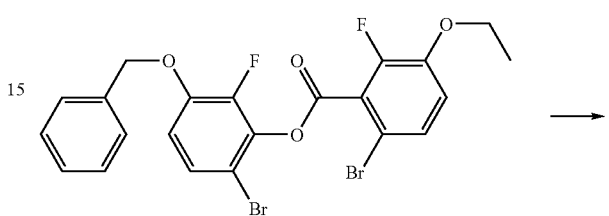

103 g (0.188 mol) of 3-benzyloxy-6-bromo-2-fluorophenyl 6-bromo-3-ethoxy-2-fluorobenzoate were dissolved in 1 l of DMF and refluxed for 72 hours in the presence of 119 g (1.88 mol) of copper powder. The batch was subsequently diluted with water and extracted with ethyl acetate, and the combined extracts were dried over sodium sulfate and evaporated. Crystallisation of the crude product from THF gave 15 g (21% of theory) of 8-ethoxy-4,7-difluoro-3-benzyloxybenzo[c]chromen-6-one as pale-yellow crystals.

Examples 842 to 881

The following are prepared analogously to Example 841:

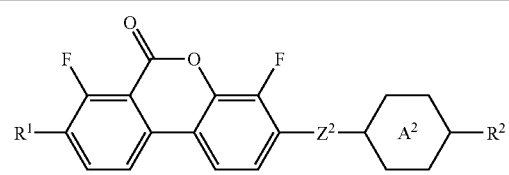

in which

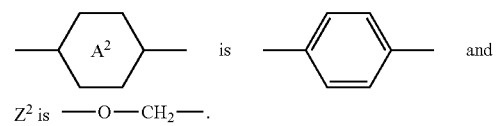

$Z^2$ is —O—CH$_2$—.

| No. | $R^1$ | $R^2$ | Phase sequence T/° C. | Δε* | T*(N,I)/ ° C. |
|---|---|---|---|---|---|
| 842 | CH$_3$ | CH$_3$ | | | |
| 843 | CH$_3$ | C$_2$H$_5$ | | | |
| 844 | CH$_3$ | n-C$_3$H$_7$ | | | |
| 845 | C$_2$H$_5$ | CH$_3$ | | | |
| 846 | C$_2$H$_5$ | C$_2$H$_5$ | | | |

-continued

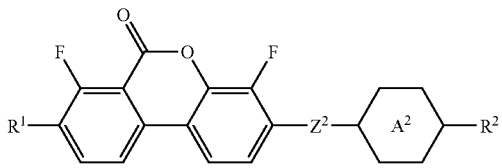

in which

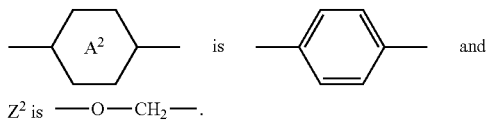

$Z^2$ is —O—CH$_2$—.

| No. | $R^1$ | $R^2$ | Phase sequence T/° C. | Δε* | T*(N,I)/ ° C. |
|---|---|---|---|---|---|
| 847 | C$_2$H$_5$ | n-C$_3$H$_7$ | | | |
| 848 | n-C$_3$H$_7$ | CH$_3$ | | | |
| 849 | n-C$_3$H$_7$ | C$_2$H$_5$ | | | |
| 850 | n-C$_3$H$_7$ | n-C$_3$H$_7$ | | | |
| 851 | n-C$_3$H$_7$ | n-C$_5$H$_{11}$ | | | |
| 852 | n-C$_5$H$_{11}$ | n-C$_3$H$_7$ | | | |
| 853 | n-C$_5$H$_{11}$ | n-C$_5$H$_{11}$ | | | |
| 854 | CH$_2$=CH | CH$_3$ | | | |
| 855 | CH$_2$=CH | C$_2$H$_5$ | | | |
| 856 | CH$_2$=CH | n-C$_3$H$_7$ | | | |
| 857 | CH$_2$=CH | CH$_2$=CH | | | |
| 858 | CH$_3$ | CH$_2$=CH | | | |
| 859 | C$_2$H$_5$ | CH$_2$=CH | | | |
| 860 | n-C$_3$H$_7$ | CH$_2$=CH | | | |
| 861 | E-CH$_3$—CH=CH | CH$_2$=CH | | | |
| 862 | E-CH$_3$—CH=CH | E-CH$_3$—CH=CH | | | |
| 863 | CH$_3$ | CH$_3$O | | | |
| 864 | CH$_3$ | C$_2$H$_5$O | | | |
| 865 | CH$_3$ | n-C$_3$H$_7$O | | | |
| 866 | n-C$_3$H$_7$ | CH$_3$O | | | |
| 867 | n-C$_3$H$_7$ | C$_2$H$_5$O | | | |
| 868a | n-C$_3$H$_7$ | n-C$_3$H$_7$O | | | |
| 868b | n-C$_5$H$_{11}$ | n-C$_4$H$_9$O | | | |
| 868c | n-C$_4$H$_9$O | n-C$_5$H$_{11}$ | | | |
| 869 | CH$_3$O | CH$_3$O | | | |
| 841 | C$_2$H$_5$O | H | | | |
| 870 | C$_2$H$_5$O | C$_2$H$_5$O | | | |
| 871 | n-C$_3$H$_7$O | n-C$_3$H$_7$O | | | |

Note:
*values extrapolated from 10% solution in ZLI-4792 or ZLI-2857 (Δε).

Example 872

(8-Ethoxy-4,7-difluoro-3-(trans-4-vinylcyclohexyl-methoxy)-6H-benzo[c]chromene)

872.1 Preparation of 8-ethoxy-4,7-difluoro-3-hydroxy-6H-benzo[c]chromene

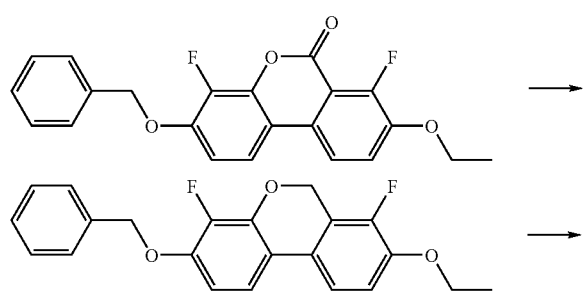

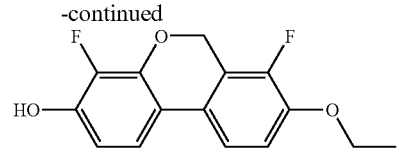

2.00 g (5.24 mmol) of 3-benzyloxy-8-ethoxy-4,7-difluoro-6H-benzo[c]chromen-6-one, the compound of Example 841, were dissolved in 12 ml of THF, and 2.37 ml (23.0 mmol) of boron trifluoride/THF complex were added with ice-cooling. 24 ml of ethylene glycol dimethyl ether and then in portions 530 mg of sodium borohydride were subsequently added. The mixture was subsequently stirred at room temperature for 18 hours and then transferred onto ice. The mixture was subjected to conventional purification, giving 1.5 g (78% of theory) of 3-benzyloxy-8-ethoxy-4,7-difluoro-6H-benzo[c]chromene as colourless crystals. These were dissolved in THF, hydrogenated at a pressure of 1 bar in the presence of 0.6 g of Pd/C (5%), filtered and evaporated, giving 1.2 g (99% of theory) of 8-ethoxy-4,7-difluoro-3-hydroxy-6H-benzo[c]chromene as colourless crystals.

872.2 Preparation of 8-ethoxy-4,7-difluoro-3-(trans-4-vinyl-cyclohexyl-methoxy)-6H-benzo[c]chromene

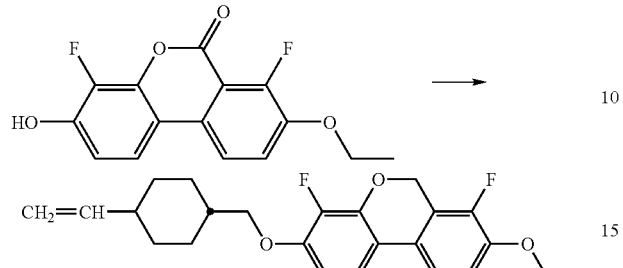

1.2 g (4.32 mmol) of 8-ethoxy4,7-difluoro-3-hydroxy-6H-benzo[c]-chromene, 2.16 g (8.64 mmol) of (trans-4-vinylcyclohexyl)methyl iodide and 650 mg (5 mmol) of potassium carbonate were refluxed for 16 hours in 15 ml of acetone. The mixture was then -transferred into MTB ether and subjected to conventional purification, giving 460. mg (27% of theory) of 8-ethoxy-4,7-difluoro-3-(trans-4-vinyl-cyclohexylmethoxy)-6 H-benzo[c]-chromene as colourless crystals.

Examples 873-902

The following are prepared analogously to Example 872:

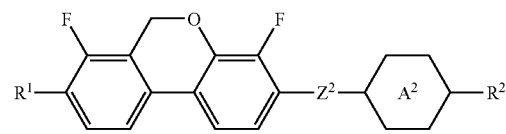

in which

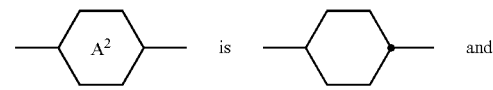

$Z^2$ is —O—CH$_2$—.

| No. | R$^1$ | R$^2$ | Phase sequence T/° C. | Δε* | T*(N,I)/ ° C. |
|---|---|---|---|---|---|
| 873 | CH$_3$ | CH$_3$ | | | |
| 874 | CH$_3$ | C$_2$H$_5$ | | | |
| 875 | CH$_3$ | n-C$_3$H$_7$ | | | |
| 876 | C$_2$H$_5$ | CH$_3$ | | | |
| 877 | C$_2$H$_5$ | C$_2$H$_5$ | | | |
| 878 | C$_2$H$_5$ | n-C$_3$H$_7$ | | | |
| 879 | n-C$_3$H$_7$ | CH$_3$ | | | |
| 880 | n-C$_3$H$_7$ | C$_2$H$_5$ | | | |
| 881 | n-C$_3$H$_7$ | n-C$_3$H$_7$ | | | |
| 882 | n-C$_3$H$_7$ | n-C$_5$H$_{11}$ | | | |
| 883 | n-C$_5$H$_{11}$ | n-C$_3$H$_7$ | | | |
| 884 | n-C$_5$H$_{11}$ | n-C$_5$H$_{11}$ | | | |
| 885 | CH$_2$=CH | CH$_3$ | | | |
| 886 | CH$_2$=CH | C$_2$H$_5$ | | | |
| 887 | CH$_2$=CH | n-C$_3$H$_7$ | | | |
| 872 | CH$_2$=CH | C$_2$H$_5$O | C 123 N 167 I | −10.4 | 207 |
| 888 | CH$_2$=CH | CH$_2$=CH | | | |
| 889 | CH$_3$ | CH$_2$=CH | | | |
| 890 | C$_2$H$_5$ | CH$_2$=CH | | | |
| 891 | n-C$_3$H$_7$ | CH$_2$=CH | | | |
| 892 | E-CH$_3$—CH=CH | CH$_2$=CH | | | |
| 893 | E-CH$_3$—CH=CH | E-CH$_3$—CH=CH | | | |
| 894 | CH$_3$ | CH$_3$O | | | |
| 895 | CH$_3$ | C$_2$H$_5$O | | | |
| 896 | CH$_3$ | n-C$_3$H$_7$O | | | |
| 897 | n-C$_3$H$_7$ | CH$_3$O | | | |
| 898 | n-C$_3$H$_7$ | C$_2$H$_5$O | | | |
| 899a | n-C$_3$H$_7$ | n-C$_3$H$_7$O | | | |
| 899b | n-C$_5$H$_{11}$ | n-C$_4$H$_9$O | C 109 SA 157 N 167.5 I | −11.2 | 199 |
| 899c | n-C$_4$H$_9$O | n-C$_5$H$_{11}$ | | | |
| 900 | CH$_3$O | CH$_3$O | | | |
| 901 | C$_2$H$_5$O | C$_2$H$_5$O | | | |
| 902 | n-C$_3$H$_7$O | n-C$_3$H$_7$O | | | |

Note:
*values extrapolated from 10% solution in ZLI-4792 or ZLI-2857 (Δε).

Examples 903 to 934

The following are prepared analogously to Example 241 and Example 361a:

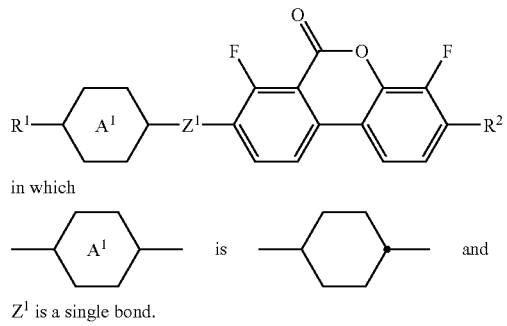

in which

—A¹— is —cyclohexyl— and $Z^1$ is a single bond.

| No. | R¹ | R² | Phase sequence T/° C. | Δε* |
|---|---|---|---|---|
| 903 | $CH_3$ | $CH_3$ | | |
| 904 | $CH_3$ | $C_2H_5$ | | |
| 905 | $CH_3$ | $n\text{-}C_3H_7$ | | |
| 906 | $C_2H_5$ | $CH_3$ | | |
| 907 | $C_2H_5$ | $C_2H_5$ | | |
| 908 | $C_2H_5$ | $n\text{-}C_3H_7$ | | |
| 909 | $n\text{-}C_3H_7$ | $CH_3$ | | |
| 910 | $n\text{-}C_3H_7$ | $C_2H_5$ | | |
| 911 | $n\text{-}C_3H_7$ | $n\text{-}C_3H_7$ | | |
| 912 | $n\text{-}C_3H_7$ | $n\text{-}C_5H_{11}$ | | |
| 913 | $n\text{-}C_5H_{11}$ | $n\text{-}C_3H_7$ | | |
| 914 | $n\text{-}C_5H_{11}$ | $n\text{-}C_5H_{11}$ | | |
| 915 | $CH_2\!=\!CH$ | $CH_3$ | | |
| 916 | $CH_2\!=\!CH$ | $C_2H_5$ | | |
| 917 | $CH_2\!=\!CH$ | $n\text{-}C_3H_7$ | | |
| 918 | $CH_2\!=\!CH$ | $CH_2\!=\!CH$ | | |
| 919 | $CH_3$ | $CH_2\!=\!CH$ | | |
| 920 | $C_2H_5$ | $CH_2\!=\!CH$ | | |
| 921 | $n\text{-}C_3H_7$ | $CH_2\!=\!CH$ | | |
| 922 | $E\text{-}CH_3\!-\!CH\!=\!CH$ | $CH_2\!=\!CH$ | | |
| 923 | $E\text{-}CH_3\!-\!CH\!=\!CH$ | $E\text{-}CH_3\!-\!CH\!=\!CH$ | | |
| 924 | $CH_3$ | $CH_3O$ | | |
| 925 | $CH_3$ | $C_2H_5O$ | | |
| 926 | $CH_3$ | $n\text{-}C_3H_7O$ | | |
| 927 | $n\text{-}C_3H_7$ | $CH_3O$ | | |
| 928 | $n\text{-}C_3H_7$ | $C_2H_5O$ | | |
| 929 | $n\text{-}C_3H_7$ | $n\text{-}C_3H_7O$ | | |
| 930 | $n\text{-}C_5H_{11}$ | $n\text{-}C_4H_9O$ | | |
| 931 | $n\text{-}C_4H_9O$ | $n\text{-}C_5H_{11}$ | | |
| 932 | $CH_3O$ | $CH_3O$ | | |
| 933 | $C_2H_5O$ | $C_2H_5O$ | | |
| 934 | $n\text{-}C_3H_7O$ | $n\text{-}C_3H_7O$ | | |

Note:
*values extrapolated from 10% solution in ZLI-4792 or ZLI-2857 (Δε).

Examples 935 to 966

The following are prepared analogously to Example 241 and Example 361a:

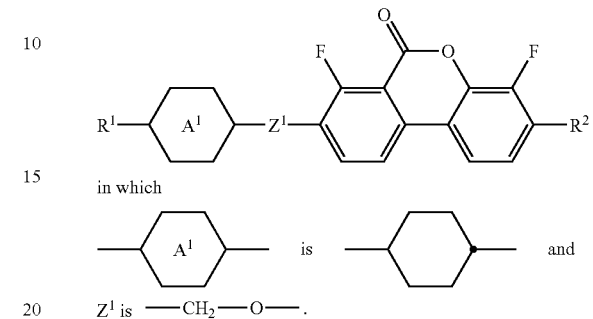

in which

—A¹— is —cyclohexyl— and $Z^1$ is —$CH_2$—O—.

| No. | R¹ | R² | Phase sequence T/° C. | Δε* |
|---|---|---|---|---|
| 935 | $CH_3$ | $CH_3$ | | |
| 936 | $CH_3$ | $C_2H_5$ | | |
| 937 | $CH_3$ | $n\text{-}C_3H_7$ | | |
| 938 | $C_2H_5$ | $CH_3$ | | |
| 939 | $C_2H_5$ | $C_2H_5$ | | |
| 940 | $C_2H_5$ | $n\text{-}C_3H_7$ | | |
| 941 | $n\text{-}C_3H_7$ | $CH_3$ | | |
| 942 | $n\text{-}C_3H_7$ | $C_2H_5$ | | |
| 943 | $n\text{-}C_3H_7$ | $n\text{-}C_3H_7$ | | |
| 944 | $n\text{-}C_3H_7$ | $n\text{-}C_5H_{11}$ | | |
| 945 | $n\text{-}C_5H_{11}$ | $n\text{-}C_3H_7$ | | |
| 946 | $n\text{-}C_5H_{11}$ | $n\text{-}C_5H_{11}$ | | |
| 947 | $CH_2\!=\!CH$ | $CH_3$ | | |
| 948 | $CH_2\!=\!CH$ | $C_2H_5$ | | |
| 949 | $CH_2\!=\!CH$ | $n\text{-}C_3H_7$ | | |
| 950 | $CH_2\!=\!CH$ | $CH_2\!=\!CH$ | | |
| 951 | $CH_3$ | $CH_2\!=\!CH$ | | |
| 952 | $C_2H_5$ | $CH_2\!=\!CH$ | | |
| 953 | $n\text{-}C_3H_7$ | $CH_2\!=\!CH$ | | |
| 954 | $E\text{-}CH_3\!-\!CH\!=\!CH$ | $CH_2\!=\!CH$ | | |
| 955 | $E\text{-}CH_3\!-\!CH\!=\!CH$ | $E\text{-}CH_3\!-\!CH\!=\!CH$ | | |
| 956 | $CH_3$ | $CH_3O$ | | |
| 957 | $CH_3$ | $C_2H_5O$ | | |
| 958 | $CH_3$ | $n\text{-}C_3H_7O$ | | |
| 959 | $n\text{-}C_3H_7$ | $CH_3O$ | | |
| 960 | $n\text{-}C_3H_7$ | $C_2H_5O$ | | |
| 961 | $n\text{-}C_3H_7$ | $n\text{-}C_3H_7O$ | | |
| 962 | $n\text{-}C_5H_{11}$ | $n\text{-}C_4H_9O$ | | |
| 963 | $n\text{-}C_4H_9O$ | $n\text{-}C_5H_{11}$ | | |
| 964 | $CH_3O$ | $CH_3O$ | | |
| 965 | $C_2H_5O$ | $C_2H_5O$ | | |
| 966 | $n\text{-}C_3H_7O$ | $n\text{-}C_3H_7O$ | | |

Note:
*values extrapolated from 10% solution in ZLI-4792 or ZLI-2857 (Δε).

Examples 967 to 998

The following are prepared analogously to Example 241 and Example 361a:

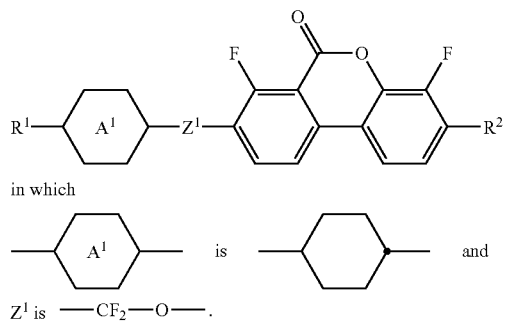

in which

—A¹— is —cyclohexyl— and $Z^1$ is —$CF_2$—O—.

| No. | R¹ | R² | Phase sequence T/° C. | Δε* |
|---|---|---|---|---|
| 967 | $CH_3$ | $CH_3$ | | |
| 968 | $CH_3$ | $C_2H_5$ | | |
| 969 | $CH_3$ | n-$C_3H_7$ | | |
| 970 | $C_2H_5$ | $CH_3$ | | |
| 971 | $C_2H_5$ | $C_2H_5$ | | |
| 972 | $C_2H_5$ | n-$C_3H_7$ | | |
| 973 | n-$C_3H_7$ | $CH_3$ | | |
| 974 | n-$C_3H_7$ | $C_2H_5$ | | |
| 975 | n-$C_3H_7$ | n-$C_3H_7$ | | |
| 976 | n-$C_3H_7$ | n-$C_5H_{11}$ | | |
| 977 | n-$C_5H_{11}$ | n-$C_3H_7$ | | |
| 978 | n-$C_5H_{11}$ | n-$C_5H_{11}$ | | |
| 979 | $CH_2$=CH | $CH_3$ | | |
| 980 | $CH_2$=CH | $C_2H_5$ | | |
| 981 | $CH_2$=CH | n-$C_3H_7$ | | |
| 982 | $CH_2$=CH | $CH_2$=CH | | |
| 983 | $CH_3$ | $CH_2$=CH | | |
| 984 | $C_2H_5$ | $CH_2$=CH | | |
| 985 | n-$C_3H_7$ | $CH_2$=CH | | |
| 986 | E-$CH_3$—CH=CH | $CH_2$=CH | | |
| 987 | E-$CH_3$—CH=CH | E-$CH_3$—CH=CH | | |
| 988 | $CH_3$ | $CH_3O$ | | |
| 989 | $CH_3$ | $C_2H_5O$ | | |
| 990 | $CH_3$ | n-$C_3H_7O$ | | |
| 991 | n-$C_3H_7$ | $CH_3O$ | | |
| 992 | n-$C_3H_7$ | $C_2H_5O$ | | |
| 993 | n-$C_3H_7$ | n-$C_3H_7O$ | | |
| 994 | n-$C_5H_{11}$ | n-$C_4H_9O$ | | |
| 995 | n-$C_4H_9O$ | n-$C_5H_{11}$ | | |
| 996 | $CH_3O$ | $CH_3O$ | | |
| 997 | $C_2H_5O$ | $C_2H_5O$ | | |
| 998 | n-$C_3H_7O$ | n-$C_3H_7O$ | | |

Note:
*values extrapolated from 10% solution in ZLI-4792 or ZLI-2857 (Δε).

Examples 999 to 1030

The following are prepared analogously to Example 241 and Example 361a:

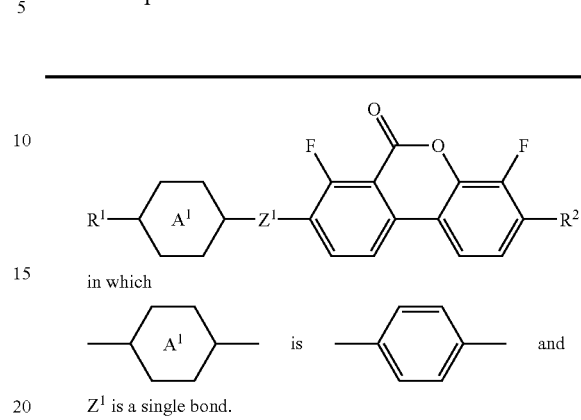

in which

—A¹— is —phenyl— and $Z^1$ is a single bond.

| No. | R¹ | R² | Phase sequence T/° C. | Δε* |
|---|---|---|---|---|
| 999 | $CH_3$ | $CH_3$ | | |
| 1000 | $CH_3$ | $C_2H_5$ | | |
| 1001 | $CH_3$ | n-$C_3H_7$ | | |
| 1002 | $C_2H_5$ | $CH_3$ | | |
| 1003 | $C_2H_5$ | $C_2H_5$ | | |
| 1004 | $C_2H_5$ | n-$C_3H_7$ | | |
| 1005 | n-$C_3H_7$ | $CH_3$ | | |
| 1006 | n-$C_3H_7$ | $C_2H_5$ | | |
| 1007 | n-$C_3H_7$ | n-$C_3H_7$ | | |
| 1008 | n-$C_3H_7$ | n-$C_5H_{11}$ | | |
| 1009 | n-$C_5H_{11}$ | n-$C_3H_7$ | | |
| 1010 | n-$C_5H_{11}$ | n-$C_5H_{11}$ | | |
| 1011 | $CH_2$=CH | $CH_3$ | | |
| 1012 | $CH_2$=CH | $C_2H_5$ | | |
| 1013 | $CH_2$=CH | n-$C_3H_7$ | | |
| 1014 | $CH_2$=CH | $CH_2$=CH | | |
| 1015 | $CH_3$ | $CH_2$=CH | | |
| 1016 | $C_2H_5$ | $CH_2$=CH | | |
| 1017 | n-$C_3H_7$ | $CH_2$=CH | | |
| 1018 | E-$CH_3$—CH=CH | $CH_2$=CH | | |
| 1019 | E-$CH_3$—CH=CH | E-$CH_3$—CH=CH | | |
| 1020 | $CH_3$ | $CH_3O$ | | |
| 1021 | $CH_3$ | $C_2H_5O$ | | |
| 1022 | $CH_3$ | n-$C_3H_7O$ | | |
| 1023 | n-$C_3H_7$ | $CH_3O$ | | |
| 1024 | n-$C_3H_7$ | $C_2H_5O$ | | |
| 1025 | n-$C_3H_7$ | n-$C_3H_7O$ | | |
| 1026 | n-$C_5H_{11}$ | n-$C_4H_9O$ | C 187 $S_A$ 230 N 230.4 I | |
| 1027 | n-$C_4H_9O$ | n-$C_5H_{11}$ | | |
| 1028 | $CH_3O$ | $CH_3O$ | | |
| 1029 | $C_2H_5O$ | $C_2H_5O$ | | |
| 1030 | n-$C_3H_7O$ | n-$C_3H_7O$ | | |

Note:
*values extrapolated from 10% solution in ZLI-4792 or ZLI-2857 (Δε).

Examples 1031 to 1062

The following are prepared analogously to Example 241 and Example 361a:

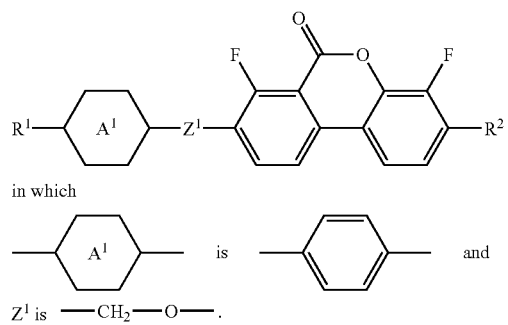

in which —A$^1$— is —⌬— and Z$^1$ is —CH$_2$—O—.

| No. | R$^1$ | R$^2$ | Phase sequence T/° C. | Δε* |
|---|---|---|---|---|
| 1031 | CH$_3$ | CH$_3$ | | |
| 1032 | CH$_3$ | C$_2$H$_5$ | | |
| 1033 | CH$_3$ | n-C$_3$H$_7$ | | |
| 1034 | C$_2$H$_5$ | CH$_3$ | | |
| 1035 | C$_2$H$_5$ | C$_2$H$_5$ | | |
| 1036 | C$_2$H$_5$ | n-C$_3$H$_7$ | | |
| 1037 | n-C$_3$H$_7$ | CH$_3$ | | |
| 1038 | n-C$_3$H$_7$ | C$_2$H$_5$ | | |
| 1039 | n-C$_3$H$_7$ | n-C$_3$H$_7$ | | |
| 1040 | n-C$_3$H$_7$ | n-C$_5$H$_{11}$ | | |
| 1041 | n-C$_5$H$_{11}$ | n-C$_3$H$_7$ | | |
| 1042 | n-C$_5$H$_{11}$ | n-C$_5$H$_{11}$ | | |
| 1043 | CH$_2$=CH | CH$_3$ | | |
| 1044 | CH$_2$=CH | C$_2$H$_5$ | | |
| 1045 | CH$_2$=CH | n-C$_3$H$_7$ | | |
| 1046 | CH$_2$=CH | CH$_2$=CH | | |
| 1047 | CH$_3$ | CH$_2$=CH | | |
| 1048 | C$_2$H$_5$ | CH$_2$=CH | | |
| 1049 | n-C$_3$H$_7$ | CH$_2$=CH | | |
| 1050 | E-CH$_3$—CH=CH | CH$_2$=CH | | |
| 1051 | E-CH$_3$—CH=CH | E-CH$_3$—CH=CH | | |
| 1052 | CH$_3$ | CH$_3$O | | |
| 1053 | CH$_3$ | C$_2$H$_5$O | | |
| 1054 | CH$_3$ | n-C$_3$H$_7$O | | |
| 1055 | n-C$_3$H$_7$ | CH$_3$O | | |
| 1056 | n-C$_3$H$_7$ | C$_2$H$_5$O | | |
| 1057 | n-C$_3$H$_7$ | n-C$_3$H$_7$O | | |
| 1058 | n-C$_5$H$_{11}$ | n-C$_5$H$_{11}$O | C 151 S$_B$ 188 S$_A$ 191 I | |
| 1059 | n-C$_4$H$_9$O | n-C$_5$H$_{11}$ | | |
| 1060 | CH$_3$O | CH$_3$O | | |
| 1061 | C$_2$H$_5$O | C$_2$H$_5$O | | |
| 1062 | n-C$_3$H$_7$O | n-C$_3$H$_7$O | | |

Note:
*values extrapolated from 10% solution in ZLI-4792 or ZLI-2857 (Δε).

Examples 1063 to 1093

The following are prepared analogously to Example 241 and Example 361a:

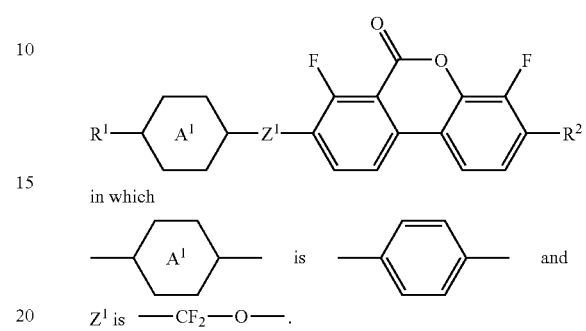

in which —A$^1$— is —⌬— and Z$^1$ is —CF$_2$—O—.

| No. | R$^1$ | R$^2$ | Phase sequence T/° C. | Δε* |
|---|---|---|---|---|
| 1063 | CH$_3$ | CH$_3$ | | |
| 1064 | CH$_3$ | C$_2$H$_5$ | | |
| 1065 | CH$_3$ | n-C$_3$H$_7$ | | |
| 1066 | C$_2$H$_5$ | CH$_3$ | | |
| 1067 | C$_2$H$_5$ | C$_2$H$_5$ | | |
| 1068 | C$_2$H$_5$ | n-C$_3$H$_7$ | | |
| 1069 | n-C$_3$H$_7$ | CH$_3$ | | |
| 1070 | n-C$_3$H$_7$ | C$_2$H$_5$ | | |
| 1071 | n-C$_3$H$_7$ | n-C$_3$H$_7$ | | |
| 1072 | n-C$_3$H$_7$ | n-C$_5$H$_{11}$ | | |
| 1073 | n-C$_5$H$_{11}$ | n-C$_3$H$_7$ | | |
| 1074 | n-C$_5$H$_{11}$ | n-C$_5$H$_{11}$ | | |
| 1075 | CH$_2$=CH | CH$_3$ | | |
| 1076 | CH$_2$=CH | C$_2$H$_5$ | | |
| 1077 | CH$_2$=CH | n-C$_3$H$_7$ | | |
| 1078 | CH$_2$=CH | CH$_2$=CH | | |
| 1079 | CH$_3$ | CH$_2$=CH | | |
| 1080 | C$_2$H$_5$ | CH$_2$=CH | | |
| 1081 | n-C$_3$H$_7$ | CH$_2$=CH | | |
| 1082 | E-CH$_3$—CH=CH | CH$_2$=CH | | |
| 1083 | E-CH$_3$—CH=CH | E-CH$_3$—CH=CH | | |
| 1084 | CH$_3$ | CH$_3$O | | |
| 1085 | CH$_3$ | C$_2$H$_5$O | | |
| 1086 | CH$_3$ | n-C$_3$H$_7$O | | |
| 1087 | n-C$_3$H$_7$ | CH$_3$O | | |
| 1088 | n-C$_3$H$_7$ | C$_2$H$_5$O | | |
| 1089 | n-C$_3$H$_7$ | n-C$_3$H$_7$O | | |
| 1090 | n-C$_4$H$_9$O | n-C$_5$H$_{11}$ | | |
| 1091 | CH$_3$O | CH$_3$O | | |
| 1092 | C$_2$H$_5$O | C$_2$H$_5$O | | |
| 1093 | n-C$_3$H$_7$O | n-C$_3$H$_7$O | | |

Note:
*values extrapolated from 10% solution in ZLI-4792 or ZLI-2857 (Δε).

Examples 1094 to 1125

The following are prepared analogously to Example 241 and Example 361a:

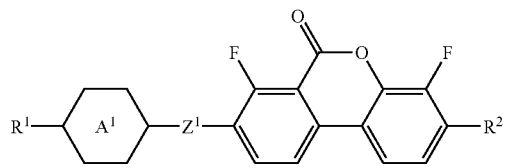

in which

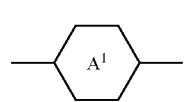 is 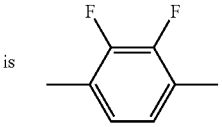 and $Z^1$ is a single bond.

| No. | $R^1$ | $R^2$ | Phase sequence T/° C. | $\Delta\epsilon$* |
|---|---|---|---|---|
| 1094 | $CH_3$ | $CH_3$ | | |
| 1095 | $CH_3$ | $C_2H_5$ | | |
| 1096 | $CH_3$ | $n\text{-}C_3H_7$ | | |
| 1097 | $C_2H_5$ | $CH_3$ | | |
| 1098 | $C_2H_5$ | $C_2H_5$ | | |
| 1099 | $C_2H_5$ | $n\text{-}C_3H_7$ | | |
| 1100 | $n\text{-}C_3H_7$ | $CH_3$ | | |
| 1101 | $n\text{-}C_3H_7$ | $C_2H_5$ | | |
| 1102 | $n\text{-}C_3H_7$ | $n\text{-}C_3H_7$ | | |
| 1103 | $n\text{-}C_3H_7$ | $n\text{-}C_5H_{11}$ | | |
| 1104 | $n\text{-}C_5H_{11}$ | $n\text{-}C_3H_7$ | | |
| 1105 | $n\text{-}C_5H_{11}$ | $n\text{-}C_5H_{11}$ | | |
| 1106 | $CH_2\!=\!CH$ | $CH_3$ | | |
| 1107 | $CH_2\!=\!CH$ | $C_2H_5$ | | |
| 1108 | $CH_2\!=\!CH$ | $n\text{-}C_3H_7$ | | |
| 1109 | $CH_2\!=\!CH$ | $CH_2\!=\!CH$ | | |
| 1110 | $CH_3$ | $CH_2\!=\!CH$ | | |
| 1111 | $C_2H_5$ | $CH_2\!=\!CH$ | | |
| 1112 | $n\text{-}C_3H_7$ | $CH_2\!=\!CH$ | | |
| 1113 | $E\text{-}CH_3\!-\!CH\!=\!CH$ | $CH_2\!=\!CH$ | | |
| 1114 | $E\text{-}CH_3\!-\!CH\!=\!CH$ | $E\text{-}CH_3\!-\!CH\!=\!CH$ | | |
| 1115 | $CH_3$ | $CH_3O$ | | |
| 1116 | $CH_3$ | $C_2H_5O$ | | |
| 1117 | $CH_3$ | $n\text{-}C_3H_7O$ | | |
| 1118 | $n\text{-}C_3H_7$ | $CH_3O$ | | |
| 1119 | $n\text{-}C_3H_7$ | $C_2H_5O$ | | |
| 1120 | $n\text{-}C_3H_7$ | $n\text{-}C_3H_7O$ | | |
| 1121 | $n\text{-}C_5H_{11}$ | $n\text{-}C_4H_9O$ | | |
| 1122 | $n\text{-}C_4H_9O$ | $n\text{-}C_5H_{11}$ | | |
| 1123 | $CH_3O$ | $CH_3O$ | | |
| 1124 | $C_2H_5O$ | $C_2H_5O$ | | |
| 1125 | $n\text{-}C_3H_7O$ | $n\text{-}C_3H_7O$ | | |

Note:
*values extrapolated from 10% solution in ZLI-4792 or ZLI-2857 ($\Delta\epsilon$).

Examples 1126 to 1157

The following are prepared analogously to Example 241 and Example 361a:

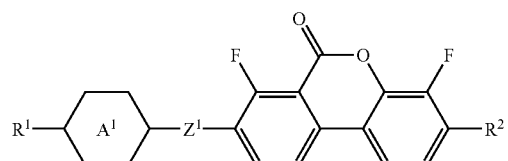

in which

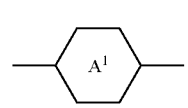 is  and $Z^1$ is $-CH_2-O-$.

| No. | $R^1$ | $R^2$ | Phase sequence T/° C. | $\Delta\epsilon$* |
|---|---|---|---|---|
| 1126 | $CH_3$ | $CH_3$ | | |
| 1127 | $CH_3$ | $C_2H_5$ | | |
| 1128 | $CH_3$ | $n\text{-}C_3H_7$ | | |
| 1129 | $C_2H_5$ | $CH_3$ | | |
| 1130 | $C_2H_5$ | $C_2H_5$ | | |
| 1131 | $C_2H_5$ | $n\text{-}C_3H_7$ | | |
| 1132 | $n\text{-}C_3H_7$ | $CH_3$ | | |
| 1133 | $n\text{-}C_3H_7$ | $C_2H_5$ | | |
| 1134 | $n\text{-}C_3H_7$ | $n\text{-}C_3H_7$ | | |
| 1135 | $n\text{-}C_3H_7$ | $n\text{-}C_5H_{11}$ | | |
| 1136 | $n\text{-}C_5H_{11}$ | $n\text{-}C_3H_7$ | | |
| 1137 | $n\text{-}C_5H_{11}$ | $n\text{-}C_5H_{11}$ | | |
| 1138 | $CH_2\!=\!CH$ | $CH_3$ | | |
| 1139 | $CH_2\!=\!CH$ | $C_2H_5$ | | |
| 1140 | $CH_2\!=\!CH$ | $n\text{-}C_3H_7$ | | |
| 1141 | $CH_2\!=\!CH$ | $CH_2\!=\!CH$ | | |
| 1142 | $CH_3$ | $CH_2\!=\!CH$ | | |
| 1143 | $C_2H_5$ | $CH_2\!=\!CH$ | | |
| 1144 | $n\text{-}C_3H_7$ | $CH_2\!=\!CH$ | | |
| 1145 | $E\text{-}CH_3\!-\!CH\!=\!CH$ | $CH_2\!=\!CH$ | | |
| 1146 | $E\text{-}CH_3\!-\!CH\!=\!CH$ | $E\text{-}CH_3\!-\!CH\!=\!CH$ | | |
| 1147 | $CH_3$ | $CH_3O$ | | |
| 1148 | $CH_3$ | $C_2H_5O$ | | |
| 1149 | $CH_3$ | $n\text{-}C_3H_7O$ | | |
| 1150 | $n\text{-}C_3H_7$ | $CH_3O$ | | |
| 1151 | $n\text{-}C_3H_7$ | $C_2H_5O$ | | |
| 1152 | $n\text{-}C_3H_7$ | $n\text{-}C_3H_7O$ | | |
| 1153 | $n\text{-}C_5H_{11}$ | $n\text{-}C_4H_9O$ | | |
| 1154 | $n\text{-}C_4H_9O$ | $n\text{-}C_5H_{11}$ | | |
| 1155 | $CH_3O$ | $CH_3O$ | | |
| 1156 | $C_2H_5O$ | $C_2H_5O$ | | |
| 1157 | $n\text{-}C_3H_7O$ | $n\text{-}C_3H_7O$ | | |

Note:
*values extrapolated from 10% solution in ZLI-4792 or ZLI-2857 ($\Delta\epsilon$).

Examples 1158 to 1190

The following are prepared analogously to Example 241 and Example 361a:

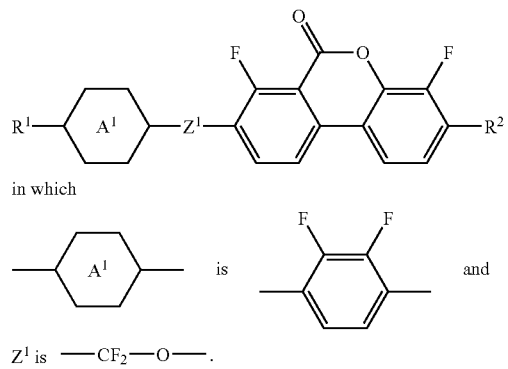

in which

—A¹— is 2,3-difluoro-1,4-phenylene and

Z¹ is —CF₂—O—.

| No. | R¹ | R² | Phase sequence T/° C. | Δε* |
|---|---|---|---|---|
| 1158 | $CH_3$ | $CH_3$ | | |
| 1159 | $CH_3$ | $C_2H_5$ | | |
| 1160 | $CH_3$ | $n\text{-}C_3H_7$ | | |
| 1161 | $C_2H_5$ | $CH_3$ | | |
| 1162 | $C_2H_5$ | $C_2H_5$ | | |
| 1163 | $C_2H_5$ | $n\text{-}C_3H_7$ | | |
| 1154 | $n\text{-}C_3H_7$ | $CH_3$ | | |
| 1165 | $n\text{-}C_3H_7$ | $C_2H_5$ | | |
| 1166 | $n\text{-}C_3H_7$ | $n\text{-}C_3H_7$ | | |
| 1167 | $n\text{-}C_3H_7$ | $n\text{-}C_5H_{11}$ | | |
| 1168 | $n\text{-}C_5H_{11}$ | $n\text{-}C_3H_7$ | | |
| 1159 | $n\text{-}C_5H_{11}$ | $n\text{-}C_5H_{11}$ | | |
| 1170 | $CH_2=CH$ | $CH_3$ | | |
| 1171 | $CH_2=CH$ | $C_2H_5$ | | |
| 1172 | $CH_2=CH$ | $n\text{-}C_3H_7$ | | |
| 1173 | $CH_2=CH$ | $CH_2=CH$ | | |
| 1174 | $CH_3$ | $CH_2=CH$ | | |
| 1175 | $C_2H_5$ | $CH_2=CH$ | | |
| 1176 | $n\text{-}C_3H_7$ | $CH_2=CH$ | | |
| 1177 | $E\text{-}CH_3\text{—}CH=CH$ | $CH_2=CH$ | | |
| 1178 | $E\text{-}CH_3\text{—}CH=CH$ | $E\text{-}CH_3\text{—}CH=CH$ | | |
| 1179 | $CH_3$ | $CH_3O$ | | |
| 1180 | $CH_3$ | $C_2H_5O$ | | |
| 1181 | $CH_3$ | $n\text{-}C_3H_7O$ | | |
| 1182 | $n\text{-}C_3H_7$ | $CH_3O$ | | |
| 1183 | $n\text{-}C_3H_7$ | $C_2H_5O$ | | |
| 1184 | $n\text{-}C_3H_7$ | $n\text{-}C_3H_7O$ | | |
| 1185 | $n\text{-}C_5H_{11}$ | $n\text{-}C_4H_9O$ | | |
| 1186 | $n\text{-}C_4H_9O$ | $n\text{-}C_5H_{11}$ | | |
| 1187 | $CH_3O$ | $CH_3O$ | | |
| 1188 | $C_2H_5O$ | $C_2H_5O$ | | |
| 1190 | $n\text{-}C_3H_7O$ | $n\text{-}C_3H_7O$ | | |

Note:
*values extrapolated from 10% solution in ZLI-4792 or ZLI-2857 (Δε).

Examples 1191 to 1222

The following are prepared analogously to Example 241 and Example 361a:

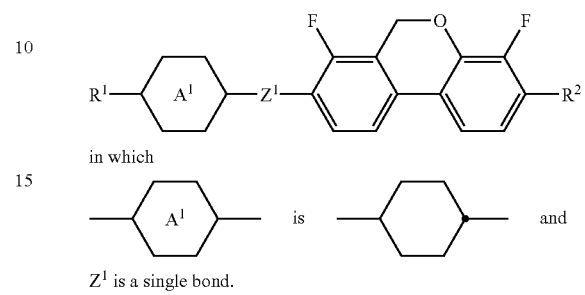

in which

—A¹— is trans-1,4-cyclohexylene and

Z¹ is a single bond.

| No. | R¹ | R² | Phase sequence T/° C. | Δε* |
|---|---|---|---|---|
| 1191 | $CH_3$ | $CH_3$ | | |
| 1192 | $CH_3$ | $C_2H_5$ | | |
| 1193 | $CH_3$ | $n\text{-}C_3H_7$ | | |
| 1194 | $C_2H_5$ | $CH_3$ | | |
| 1195 | $C_2H_5$ | $C_2H_5$ | | |
| 1196 | $C_2H_5$ | $n\text{-}C_3H_7$ | | |
| 1197 | $n\text{-}C_3H_7$ | $CH_3$ | | |
| 1198 | $n\text{-}C_3H_7$ | $C_2H_5$ | | |
| 1199 | $n\text{-}C_3H_7$ | $n\text{-}C_3H_7$ | | |
| 1200 | $n\text{-}C_3H_7$ | $n\text{-}C_5H_{11}$ | | |
| 1201 | $n\text{-}C_5H_{11}$ | $n\text{-}C_3H_7$ | | |
| 1202 | $n\text{-}C_5H_{11}$ | $n\text{-}C_5H_{11}$ | | |
| 1203 | $CH_2=CH$ | $CH_3$ | | |
| 1204 | $CH_2=CH$ | $C_2H_5$ | | |
| 1205 | $CH_2=CH$ | $n\text{-}C_3H_7$ | | |
| 1206 | $CH_2=CH$ | $CH_2=CH$ | | |
| 1207 | $CH_3$ | $CH_2=CH$ | | |
| 1208 | $C_2H_5$ | $CH_2=CH$ | | |
| 1209 | $n\text{-}C_3H_7$ | $CH_2=CH$ | | |
| 1200 | $E\text{-}CH_3\text{—}CH=CH$ | $CH_2=CH$ | | |
| 1211 | $E\text{-}CH_3\text{—}CH=CH$ | $E\text{-}CH_3\text{—}CH=CH$ | | |
| 1212 | $CH_3$ | $CH_3O$ | | |
| 1213 | $CH_3$ | $C_2H_5O$ | | |
| 1214 | $CH_3$ | $n\text{-}C_3H_7O$ | | |
| 1215 | $n\text{-}C_3H_7$ | $CH_3O$ | | |
| 1216 | $n\text{-}C_3H_7$ | $C_2H_5O$ | | |
| 1217 | $n\text{-}C_3H_7$ | $n\text{-}C_3H_7O$ | | |
| 1218 | $n\text{-}C_5H_{11}$ | $n\text{-}C_4H_9O$ | | |
| 1219 | $n\text{-}C_4H_9O$ | $n\text{-}C_5H_{11}$ | | |
| 1220 | $CH_3O$ | $CH_3O$ | | |
| 1221 | $C_2H_5O$ | $C_2H_5O$ | | |
| 1222 | $n\text{-}C_3H_7O$ | $n\text{-}C_3H_7O$ | | |

Note:
*values extrapolated from 10% solution in ZLI-4792 or ZLI-2857 (Δε).

Examples 1223 to 1254

The following are prepared analogously to Example 241 and Example 361a:

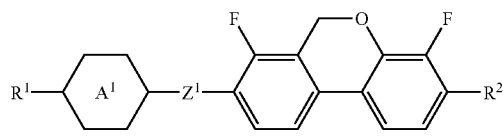

in which

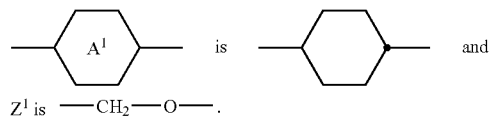 is and $Z^1$ is —CH$_2$—O—.

| No. | R$^1$ | R$^2$ | Phase sequence T/° C. | Δε* |
|---|---|---|---|---|
| 1223 | CH$_3$ | CH$_3$ | | |
| 1224 | CH$_3$ | C$_2$H$_5$ | | |
| 1225 | CH$_3$ | n-C$_3$H$_7$ | | |
| 1226 | C$_2$H$_5$ | CH$_3$ | | |
| 1227 | C$_2$H$_5$ | C$_2$H$_5$ | | |
| 1228 | C$_2$H$_5$ | n-C$_3$H$_7$ | | |
| 1229 | n-C$_3$H$_7$ | CH$_3$ | | |
| 1230 | n-C$_3$H$_7$ | C$_2$H$_5$ | | |
| 1231 | n-C$_3$H$_7$ | n-C$_3$H$_7$ | | |
| 1232 | n-C$_3$H$_7$ | n-C$_5$H$_{11}$ | | |
| 1233 | n-C$_5$H$_{11}$ | n-C$_3$H$_7$ | | |
| 1234 | n-C$_5$H$_{11}$ | n-C$_5$H$_{11}$ | | |
| 1235 | CH$_2$=CH | CH$_3$ | | |
| 1236 | CH$_2$=CH | C$_2$H$_5$ | | |
| 1237 | CH$_2$=CH | n-C$_3$H$_7$ | | |
| 1238 | CH$_2$=CH | CH$_2$=CH | | |
| 1239 | CH$_3$ | CH$_2$=CH | | |
| 1240 | C$_2$H$_5$ | CH$_2$=CH | | |
| 1241 | n-C$_3$H$_7$ | CH$_2$=CH | | |
| 1242 | E-CH$_3$—CH=CH | CH$_2$=CH | | |
| 1243 | E-CH$_3$—CH=CH | E-CH$_3$—CH=CH | | |
| 1244 | CH$_3$ | CH$_3$O | | |
| 1245 | CH$_3$ | C$_2$H$_5$O | | |
| 1246 | CH$_3$ | n-C$_3$H$_7$O | | |
| 1247 | n-C$_3$H$_7$ | CH$_3$O | | |
| 1248 | n-C$_3$H$_7$ | C$_2$H$_5$O | | |
| 1249 | n-C$_3$H$_7$ | n-C$_3$H$_7$O | | |
| 1250 | n-C$_5$H$_{11}$ | n-C$_4$H$_9$O | | |
| 1251 | n-C$_4$H$_9$O | n-C$_5$H$_{11}$ | | |
| 1252 | CH$_3$O | CH$_3$O | | |
| 1253 | C$_2$H$_5$O | C$_2$H$_5$O | | |
| 1254 | n-C$_3$H$_7$O | n-C$_3$H$_7$O | | |

Note:
*values extrapolated from 10% solution in ZLI-4792 or ZLI-2857 (Δε).

Examples 1255 to 1286

The following are prepared analogously to Example 241 and Example 361a:

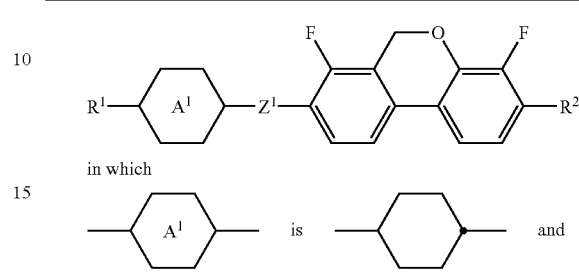

in which

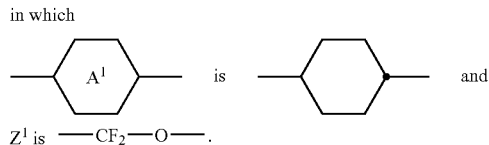 is and $Z^1$ is —CF$_2$—O—.

| No. | R$^1$ | R$^2$ | Phase sequence T/° C. | Δε* |
|---|---|---|---|---|
| 1255 | CH$_3$ | CH$_3$ | | |
| 1256 | CH$_3$ | C$_2$H$_5$ | | |
| 1257 | CH$_3$ | n-C$_3$H$_7$ | | |
| 1258 | C$_2$H$_5$ | CH$_3$ | | |
| 1259 | C$_2$H$_5$ | C$_2$H$_5$ | | |
| 1260 | C$_2$H$_5$ | n-C$_3$H$_7$ | | |
| 1261 | n-C$_3$H$_7$ | CH$_3$ | | |
| 1262 | n-C$_3$H$_7$ | C$_2$H$_5$ | | |
| 1263 | n-C$_3$H$_7$ | n-C$_3$H$_7$ | | |
| 1264 | n-C$_3$H$_7$ | n-C$_5$H$_{11}$ | | |
| 1265 | n-C$_5$H$_{11}$ | n-C$_3$H$_7$ | | |
| 1266 | n-C$_5$H$_{11}$ | n-C$_5$H$_{11}$ | | |
| 1267 | CH$_2$=CH | CH$_3$ | | |
| 1268 | CH$_2$=CH | C$_2$H$_5$ | | |
| 1269 | CH$_2$=CH | n-C$_3$H$_7$ | | |
| 1270 | CH$_2$=CH | CH$_2$=CH | | |
| 1271 | CH$_3$ | CH$_2$=CH | | |
| 1272 | C$_2$H$_5$ | CH$_2$=CH | | |
| 1273 | n-C$_3$H$_7$ | CH$_2$=CH | | |
| 1274 | E-CH$_3$—CH=CH | CH$_2$=CH | | |
| 1275 | E-CH$_3$—CH=CH | E-CH$_3$—CH=CH | | |
| 1276 | CH$_3$ | CH$_3$O | | |
| 1277 | CH$_3$ | C$_2$H$_5$O | | |
| 1278 | CH$_3$ | n-C$_3$H$_7$O | | |
| 1279 | n-C$_3$H$_7$ | CH$_3$O | | |
| 1280 | n-C$_3$H$_7$ | C$_2$H$_5$O | | |
| 1281 | n-C$_3$H$_7$ | n-C$_3$H$_7$O | | |
| 1252 | n-C$_5$H$_{11}$ | n-C$_4$H$_9$O | | |
| 1283 | n-C$_4$H$_9$O | n-C$_5$H$_{11}$ | | |
| 1284 | CH$_3$O | CH$_3$O | | |
| 1285 | C$_2$H$_5$O | C$_2$H$_5$O | | |
| 1286 | n-C$_3$H$_7$O | n-C$_3$H$_7$O | | |

Note:
*values extrapolated from 10% solution in ZLI-4792 or ZLI-2857 (Δε).

Examples 1287 to 1318

The following are prepared analogously to Example 241 and Example 361a:

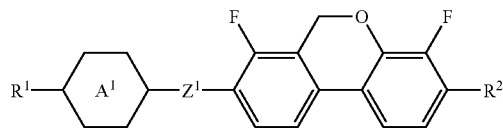

in which

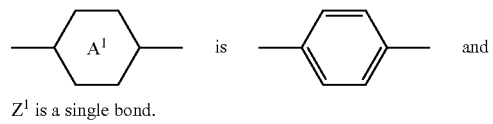 is ⎯⟨phenylene⟩⎯ and $Z^1$ is a single bond.

| No. | $R^1$ | $R^2$ | Phase sequence T/° C. | Δε* |
|---|---|---|---|---|
| 1287 | $CH_3$ | $CH_3$ | | |
| 1288 | $CH_3$ | $C_2H_5$ | | |
| 1289 | $CH_3$ | $n\text{-}C_3H_7$ | | |
| 1290 | $C_2H_5$ | $CH_3$ | | |
| 1291 | $C_2H_5$ | $C_2H_5$ | | |
| 1292 | $C_2H_5$ | $n\text{-}C_3H_7$ | | |
| 1293 | $n\text{-}C_3H_7$ | $CH_3$ | | |
| 1294 | $n\text{-}C_3H_7$ | $C_2H_5$ | | |
| 1295 | $n\text{-}C_3H_7$ | $n\text{-}C_3H_7$ | | |
| 1296 | $n\text{-}C_3H_7$ | $n\text{-}C_5H_{11}$ | | |
| 1297 | $n\text{-}C_5H_{11}$ | $n\text{-}C_3H_7$ | | |
| 1298 | $n\text{-}C_5H_{11}$ | $n\text{-}C_5H_{11}$ | | |
| 1299 | $CH_2{=}CH$ | $CH_3$ | | |
| 1300 | $CH_2{=}CH$ | $C_2H_5$ | | |
| 1301 | $CH_2{=}CH$ | $n\text{-}C_3H_7$ | | |
| 1302 | $CH_2{=}CH$ | $CH_2{=}CH$ | | |
| 1303 | $CH_3$ | $CH_2{=}CH$ | | |
| 1304 | $C_2H_5$ | $CH_2{=}CH$ | | |
| 1305 | $n\text{-}C_3H_7$ | $CH_2{=}CH$ | | |
| 1306 | $E\text{-}CH_3{-}CH{=}CH$ | $CH_2{=}CH$ | | |
| 1307 | $E\text{-}CH_3{-}CH{=}CH$ | $E\text{-}CH_3{-}CH{=}CH$ | | |
| 1308 | $CH_3$ | $CH_3O$ | | |
| 1309 | $CH_3$ | $C_2H_5O$ | | |
| 1310 | $CH_3$ | $n\text{-}C_3H_7O$ | | |
| 1311 | $n\text{-}C_3H_7$ | $CH_3O$ | | |
| 1312 | $n\text{-}C_3H_7$ | $C_2H_5O$ | | |
| 1313 | $n\text{-}C_3H_7$ | $n\text{-}C_3H_7O$ | | |
| 1314 | $n\text{-}C_5H_{11}$ | $n\text{-}C_4H_9O$ | | |
| 1315 | $n\text{-}C_4H_9O$ | $n\text{-}C_5H_{11}$ | | |
| 1316 | $CH_3O$ | $CH_3O$ | | |
| 1317 | $C_2H_5O$ | $C_2H_5O$ | | |
| 1318 | $n\text{-}C_3H_7O$ | $n\text{-}C_3H_7O$ | | |

Note:
*values extrapolated from 10% solution in ZLI-4792 or ZLI-2857 (Δε).

Examples 1319 to 1350

The following are prepared analogously to Example 241 and Example 361a:

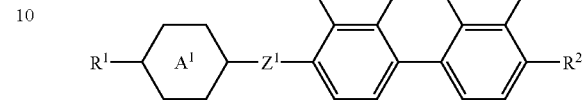

in which

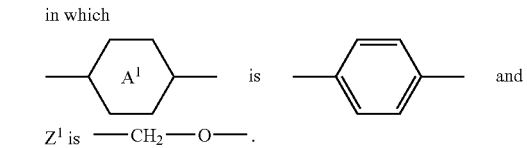 is ⎯⟨phenylene⟩⎯ and $Z^1$ is ⎯$CH_2$⎯$O$⎯.

| No. | $R^1$ | $R^2$ | Phase sequence T/° C. | Δε* |
|---|---|---|---|---|
| 1319 | $CH_3$ | $CH_3$ | | |
| 1320 | $CH_3$ | $C_2H_5$ | | |
| 1321 | $CH_3$ | $n\text{-}C_3H_7$ | | |
| 1322 | $C_2H_5$ | $CH_3$ | | |
| 1323 | $C_2H_5$ | $C_2H_5$ | | |
| 1324 | $C_2H_5$ | $n\text{-}C_3H_7$ | | |
| 1325 | $n\text{-}C_3H_7$ | $CH_3$ | | |
| 1326 | $n\text{-}C_3H_7$ | $C_2H_5$ | | |
| 1327 | $n\text{-}C_3H_7$ | $n\text{-}C_3H_7$ | | |
| 1328 | $n\text{-}C_3H_7$ | $n\text{-}C_5H_{11}$ | | |
| 1329 | $n\text{-}C_5H_{11}$ | $n\text{-}C_3H_7$ | | |
| 1330 | $n\text{-}C_5H_{11}$ | $n\text{-}C_5H_{11}$ | | |
| 1331 | $CH_2{=}CH$ | $CH_3$ | | |
| 1332 | $CH_2{=}CH$ | $C_2H_5$ | | |
| 1333 | $CH_2{=}CH$ | $n\text{-}C_3H_7$ | | |
| 1334 | $CH_2{=}CH$ | $CH_2{=}CH$ | | |
| 1335 | $CH_3$ | $CH_2{=}CH$ | | |
| 1336 | $C_2H_5$ | $CH_2{=}CH$ | | |
| 1337 | $n\text{-}C_3H_7$ | $CH_2{=}CH$ | | |
| 1338 | $E\text{-}CH_3{-}CH{=}CH$ | $CH_2{=}CH$ | | |
| 1339 | $E\text{-}CH_3{-}CH{=}CH$ | $E\text{-}CH_3{-}CH{=}CH$ | | |
| 1340 | $CH_3$ | $CH_3O$ | | |
| 1341 | $CH_3$ | $C_2H_5O$ | | |
| 1342 | $CH_3$ | $n\text{-}C_3H_7O$ | | |
| 1343 | $n\text{-}C_3H_7$ | $CH_3O$ | | |
| 1344 | $n\text{-}C_3H_7$ | $C_2H_5O$ | | |
| 1345 | $n\text{-}C_3H_7$ | $n\text{-}C_3H_7O$ | | |
| 1346 | $n\text{-}C_5H_{11}$ | $n\text{-}C_4H_9O$ | C 112 $S_A$ 149 I | −8.1 |
| 1347 | $n\text{-}C_4H_9O$ | $n\text{-}C_5H_{11}$ | | |
| 1348 | $CH_3O$ | $CH_3O$ | | |
| 1349 | $C_2H_5O$ | $C_2H_5O$ | | |
| 1350 | $n\text{-}C_3H_7O$ | $n\text{-}C_3H_7O$ | | |

Note:
*values extrapolated from 10% solution in ZLI-4792 or ZLI-2857 (Δε).

Examples 1351 to 1382

The following are prepared analogously to Example 241 and Example 361a:

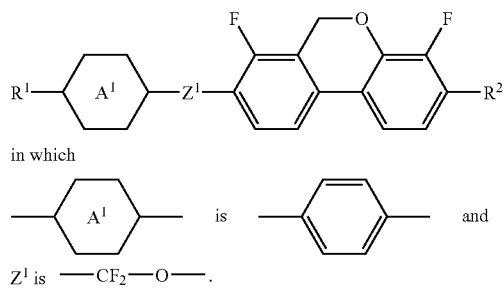

in which $A^1$ is —⟨phenyl⟩— and $Z^1$ is —CF$_2$—O—.

| No. | $R^1$ | $R^2$ | Phase sequence T/° C. | Δε* |
|---|---|---|---|---|
| 1351 | CH$_3$ | CH$_3$ | | |
| 1352 | CH$_3$ | C$_2$H$_5$ | | |
| 1353 | CH$_3$ | n-C$_3$H$_7$ | | |
| 1354 | C$_2$H$_5$ | CH$_3$ | | |
| 1355 | C$_2$H$_5$ | C$_2$H$_5$ | | |
| 1356 | C$_2$H$_5$ | n-C$_3$H$_7$ | | |
| 1357 | n-C$_3$H$_7$ | CH$_3$ | | |
| 1358 | n-C$_3$H$_7$ | C$_2$H$_5$ | | |
| 1359 | n-C$_3$H$_7$ | n-C$_3$H$_7$ | | |
| 1360 | n-C$_3$H$_7$ | n-C$_5$H$_{11}$ | | |
| 1361 | n-C$_5$H$_{11}$ | n-C$_3$H$_7$ | | |
| 1362 | n-C$_5$H$_{11}$ | n-C$_5$H$_{11}$ | | |
| 1363 | CH$_2$=CH | CH$_3$ | | |
| 1364 | CH$_2$=CH | C$_2$H$_5$ | | |
| 1365 | CH$_2$=CH | n-C$_3$H$_7$ | | |
| 1366 | CH$_2$=CH | CH$_2$=CH | | |
| 1367 | CH$_3$ | CH$_2$=CH | | |
| 1368 | C$_2$H$_5$ | CH$_2$=CH | | |
| 1369 | n-C$_3$H$_7$ | CH$_2$=CH | | |
| 1370 | E-CH$_3$—CH=CH | CH$_2$=CH | | |
| 1371 | E-CH$_3$—CH=CH | E-CH$_3$—CH=CH | | |
| 1372 | CH$_3$ | CH$_3$O | | |
| 1373 | CH$_3$ | C$_2$H$_5$O | | |
| 1374 | CH$_3$ | n-C$_3$H$_7$O | | |
| 1375 | n-C$_3$H$_7$ | CH$_3$O | | |
| 1376 | n-C$_3$H$_7$ | C$_2$H$_5$O | | |
| 1377 | n-C$_3$H$_7$ | n-C$_3$H$_7$O | | |
| 1378 | n-C$_5$H$_{11}$ | n-C$_4$H$_9$O | | |
| 1379 | n-C$_4$H$_9$O | n-C$_5$H$_{11}$ | | |
| 1380 | CH$_3$O | CH$_3$O | | |
| 1381 | C$_2$H$_5$O | C$_2$H$_5$O | | |
| 1382 | n-C$_3$H$_7$O | n-C$_3$H$_7$O | | |

Note:
*values extrapolated from 10% solution in ZLI-4792 or ZLI-2857 (Δε).

Examples 1383 to 1385

The following are prepared analogously to Example 241 and Example 361a:

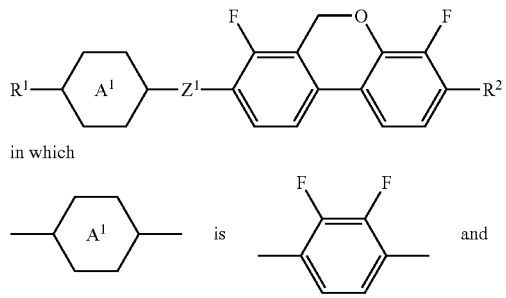

in which $A^1$ is —⟨2,3-difluorophenyl⟩— and $Z^1$ is a single bond.

| No. | $R^1$ | $R^2$ | Phase sequence T/° C. | Δε* |
|---|---|---|---|---|
| 1383 | CH$_3$ | CH$_3$ | | |
| 1384 | CH$_3$ | C$_2$H$_5$ | | |
| 1385 | CH$_3$ | n-C$_3$H$_7$ | | |
| 1386 | C$_2$H$_5$ | CH$_3$ | | |
| 1387 | C$_2$H$_5$ | C$_2$H$_5$ | | |
| 1388 | C$_2$H$_5$ | n-C$_3$H$_7$ | | |
| 1389 | n-C$_3$H$_7$ | CH$_3$ | | |
| 1390 | n-C$_3$H$_7$ | C$_2$H$_5$ | | |
| 1391 | n-C$_3$H$_7$ | n-C$_3$H$_7$ | | |
| 1392 | n-C$_3$H$_7$ | n-C$_5$H$_{11}$ | | |
| 1393 | n-C$_5$H$_{11}$ | n-C$_3$H$_7$ | | |
| 1394 | n-C$_5$H$_{11}$ | n-C$_5$H$_{11}$ | | |
| 1395 | CH$_2$=CH | CH$_3$ | | |
| 1396 | CH$_2$=CH | C$_2$H$_5$ | | |
| 1397 | CH$_2$=CH | n-C$_3$H$_7$ | | |
| 1398 | CH$_2$=CH | CH$_2$=CH | | |
| 1399 | CH$_3$ | CH$_2$=CH | | |
| 1400 | C$_2$H$_5$ | CH$_2$=CH | | |
| 1401 | n-C$_3$H$_7$ | CH$_2$=CH | | |
| 1402 | E-CH$_3$—CH=CH | CH$_2$=CH | | |
| 1403 | E-CH$_3$—CH=CH | E-CH$_3$—CH=CH | | |
| 1404 | CH$_3$ | CH$_3$O | | |
| 1405 | CH$_3$ | C$_2$H$_5$O | | |
| 1406 | CH$_3$ | n-C$_3$H$_7$O | | |
| 1407 | n-C$_3$H$_7$ | CH$_3$O | | |
| 1408 | n-C$_3$H$_7$ | C$_2$H$_5$O | | |
| 1409 | n-C$_3$H$_7$ | n-C$_3$H$_7$O | | |
| 1410 | n-C$_5$H$_{11}$ | n-C$_4$H$_9$O | | |
| 1411 | n-C$_4$H$_9$O | n-C$_5$H$_{11}$ | | |
| 1412 | CH$_3$O | CH$_3$O | | |
| 1413 | C$_2$H$_5$O | C$_2$H$_5$O | | |
| 1414 | n-C$_3$H$_7$O | n-C$_3$H$_7$O | | |

Note:
*values extrapolated from 10% solution in ZLI-4792 or ZLI-2857 (Δε).

Examples 1415 to 1446

The following are prepared analogously to Example 241 and Example 361a:

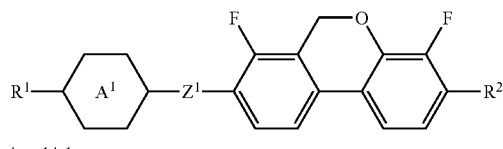

in which

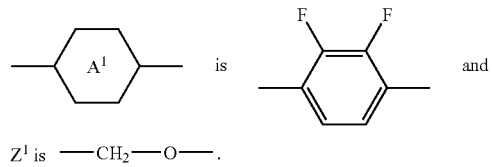

$Z^1$ is —CH$_2$—O—.

| No. | R$^1$ | R$^2$ | Phase sequence T/° C. | Δε* |
|---|---|---|---|---|
| 1415 | CH$_3$ | CH$_3$ | | |
| 1416 | CH$_3$ | C$_2$H$_5$ | | |
| 1417 | CH$_3$ | n-C$_3$H$_7$ | | |
| 1418 | C$_2$H$_5$ | CH$_3$ | | |
| 1419 | C$_2$H$_5$ | C$_2$H$_5$ | | |
| 1420 | C$_2$H$_5$ | n-C$_3$H$_7$ | | |
| 1421 | n-C$_3$H$_7$ | CH$_3$ | | |
| 1422 | n-C$_3$H$_7$ | C$_2$H$_5$ | | |
| 1423 | n-C$_3$H$_7$ | n-C$_3$H$_7$ | | |
| 1424 | n-C$_3$H$_7$ | n-C$_5$H$_{11}$ | | |
| 1425 | n-C$_5$H$_{11}$ | n-C$_3$H$_7$ | | |
| 1426 | n-C$_5$H$_{11}$ | n-C$_5$H$_{11}$ | | |
| 1427 | CH$_2$=CH | CH$_3$ | | |
| 1428 | CH$_2$=CH | C$_2$H$_5$ | | |
| 1429 | CH$_2$=CH | n-C$_3$H$_7$ | | |
| 1430 | CH$_2$=CH | CH$_2$=CH | | |
| 1431 | CH$_3$ | CH$_2$=CH | | |
| 1432 | C$_2$H$_5$ | CH$_2$=CH | | |
| 1433 | n-C$_3$H$_7$ | CH$_2$=CH | | |
| 1434 | E-CH$_3$—CH=CH | CH$_2$=CH | | |
| 1435 | E-CH$_3$—CH=CH | E-CH$_3$—CH=CH | | |
| 1436 | CH$_3$ | CH$_3$O | | |
| 1437 | CH$_3$ | C$_2$H$_5$O | | |
| 1438 | CH$_3$ | n-C$_3$H$_7$O | | |
| 1439 | n-C$_3$H$_7$ | CH$_3$O | | |
| 1440 | n-C$_3$H$_7$ | C$_2$H$_5$O | | |
| 1441 | n-C$_3$H$_7$ | n-C$_3$H$_7$O | | |
| 1442 | n-C$_5$H$_{11}$ | n-C$_4$H$_9$O | | |
| 1443 | n-C$_4$H$_9$O | n-C$_5$H$_{11}$ | | |
| 1444 | CH$_3$O | CH$_3$O | | |
| 1445 | C$_2$H$_5$O | C$_2$H$_5$O | | |
| 1446 | n-C$_3$H$_7$O | n-C$_3$H$_7$O | | |

Note:
*values extrapolated from 10% solution in ZLI-4792 or ZLI-2857 (Δε).

Examples 1447 to 1478

The following are prepared analogously to Example 241 and Example 361a:

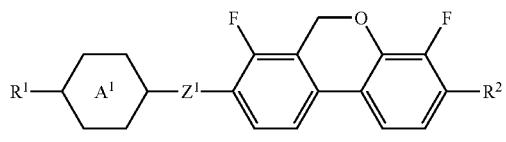

in which

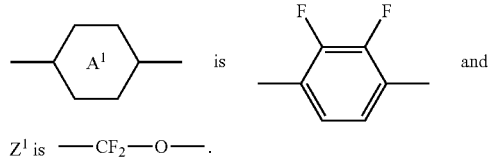

$Z^1$ is —CF$_2$—O—.

| No. | R$^1$ | R$^2$ | Phase sequence T/° C. | Δε* |
|---|---|---|---|---|
| 1447 | CH$_3$ | CH$_3$ | | |
| 1448 | CH$_3$ | C$_2$H$_5$ | | |
| 1449 | CH$_3$ | n-C$_3$H$_7$ | | |
| 1450 | C$_2$H$_5$ | CH$_3$ | | |
| 1451 | C$_2$H$_5$ | C$_2$H$_5$ | | |
| 1452 | C$_2$H$_5$ | n-C$_3$H$_7$ | | |
| 1453 | n-C$_3$H$_7$ | CH$_3$ | | |
| 1454 | n-C$_3$H$_7$ | C$_2$H$_5$ | | |
| 1455 | n-C$_3$H$_7$ | n-C$_3$H$_7$ | | |
| 1456 | n-C$_3$H$_7$ | n-C$_5$H$_{11}$ | | |
| 1457 | n-C$_5$H$_{11}$ | n-C$_3$H$_7$ | | |
| 1458 | n-C$_5$H$_{11}$ | n-C$_5$H$_{11}$ | | |
| 1459 | CH$_2$=CH | CH$_3$ | | |
| 1460 | CH$_2$=CH | C$_2$H$_5$ | | |
| 1461 | CH$_2$=CH | n-C$_3$H$_7$ | | |
| 1462 | CH$_2$=CH | CH$_2$=CH | | |
| 1463 | CH$_3$ | CH$_2$=CH | | |
| 1464 | C$_2$H$_5$ | CH$_2$=CH | | |
| 1465 | n-C$_3$H$_7$ | CH$_2$=CH | | |
| 1466 | E-CH$_3$—CH=CH | CH$_2$=CH | | |
| 1467 | E-CH$_3$—CH=CH | E-CH$_3$—CH=CH | | |
| 1468 | CH$_3$ | CH$_3$O | | |
| 1469 | CH$_3$ | C$_2$H$_5$O | | |
| 1470 | CH$_3$ | n-C$_3$H$_7$O | | |
| 1471 | n-C$_3$H$_7$ | CH$_3$O | | |
| 1472 | n-C$_3$H$_7$ | C$_2$H$_5$O | | |
| 1473 | n-C$_3$H$_7$ | n-C$_3$H$_7$O | | |
| 1474 | n-C$_5$H$_{11}$ | n-C$_4$H$_9$O | | |
| 1475 | n-C$_4$H$_9$O | n-C$_5$H$_{11}$ | | |
| 1476 | CH$_3$O | CH$_3$O | | |
| 1477 | C$_2$H$_5$O | C$_2$H$_5$O | | |
| 1478 | n-C$_3$H$_7$O | n-C$_3$H$_7$O | | |

Note:
*values extrapolated from 10% solution in ZLI-4792 or ZLI-2857 (Δε).

Mixture Examples

Liquid-crystalline mixtures are prepared and their applicational properties are investigated.

Example M-1

A liquid-crystal mixture having the composition indicated in the following table was prepared and investigated. It has the properties likewise shown in the table.

| Compound # | Abbreviation | Conc./% by wt. | Physical properties | |
|---|---|---|---|---|
| 1 | PCH-301 | 9.0 | T(N, I) = | 65.9° C. |
| 2 | PCH-302 | 9.0 | $\epsilon_\perp$(20° C., 1 kHz) > | 6.1 |
| 3 | CCH-301 | 29.7 | $\Delta\epsilon$(20° C., 1 kHz) > | −2.3 |
| 4 | CCN-47 | 9.9 | | |
| 5 | CCN-55 | 9.0 | | |
| 6 | CBC-33F | 4.5 | | |
| 7 | CBC-53F | 4.5 | | |
| 8 | CBC-55F | 4.5 | | |
| 9 | CBC-33 | 4.5 | | |
| 10 | CBC-53 | 5.4 | | |
| 11 | BFFO-3-5FF | 10.0 | | |
| Σ | | 100.0 | | |

The liquid-crystal medium has very good applicational properties.

Example M-2

A liquid-crystal mixture having the composition indicated in the following table was prepared and investigated. It has the properties likewise shown in the table.

| Compound # | Abbreviation | Conc./% by wt. | Physical properties | |
|---|---|---|---|---|
| 1 | PCH-301 | 9.0 | T(N, I) = | 76.9° C. |
| 2 | PCH-302 | 9.0 | $\epsilon_\perp$(20° C., 1 kHz) > | 5.4 |
| 3 | CCH-301 | 29.7 | $\Delta\epsilon$(20° C., 1 kHz) > | −1.9 |
| 4 | CCN-47 | 9.9 | | |
| 5 | CCN-55 | 9.0 | | |
| 6 | CBC-33F | 4.5 | | |
| 7 | CBC-53F | 4.5 | | |
| 8 | CBC-55F | 4.5 | | |
| 9 | CBC-33 | 4.5 | | |
| 10 | CBC-53 | 5.4 | | |
| 11 | BHHO-3O-5FF | 10.0 | | |
| Σ | | 100.0 | | |

The liquid-crystal medium has very good applicational properties.

Example M-3

The mixture shown in the following table is prepared and investigated.

| Compound # | Abbreviation | Conc./% by wt. | Physical properties | |
|---|---|---|---|---|
| 1 | PCH-304FF | 16.0 | T(N, I) = | 70° C. |
| 2 | PCH-502FF | 8.0 | $\Delta$n(20° C., 589 nm) = | 0.100 |
| 3 | PCH-504FF | 14.0 | $\Delta\epsilon$(20° C., 1 kHz) > | −4.5 |
| 4 | CCP-302FF | 14.0 | | |
| 5 | CCP-502FF | 12.0 | | |
| 6 | CCH-35 | 6.0 | | |
| 7 | CC-3-V1 | 8.0 | | |
| 8 | CCP-V-1 | 8.0 | | |
| 9 | BCH-32 | 8.0 | | |
| 10 | BFFO-3-5FF | 3.0 | | |
| 11 | BHHO-20-5FF | 3.0 | | |
| Σ | | 100.0 | | |

The liquid-crystal medium has excellent applicational properties.

Example M-4

The mixture shown in the following table is prepared and investigated.

| Compound # | Abbreviation | Conc./% by wt. | Physical properties | |
|---|---|---|---|---|
| 1 | PCH-304FF | 7.0 | T(N, I) = | 95.5° C. |
| 2 | CCP-402FF | 2.0 | $\Delta$n (20° C., 589 nm) = | 0.128 |
| 3 | CCP-303FF | 7.0 | $\Delta\epsilon$ (20° C., 1 kHz) > | −3.2 |
| 4 | BCH-202FF | 11.0 | $k_1$ (20° C.) = | 16.0 pN |
| 5 | BCH-302FF | 11.0 | $k_1/k_3$ (20° C.) = | 0.94 |
| 6 | PYP-2-3 | 10.0 | $\gamma_1$ (20° C.) = | 154 mPa·s |
| 7 | PYP-2-4 | 10.0 | $t_{store}$ (−20° C.) > | 1,000 h |
| 8 | CC-4-V | 10.0 | $V_0$ (20° C.) = | 2.28 V |
| 9 | CC-5-V | 10.0 | | |
| 10 | CC-3-V1 | 10.0 | | |
| 11 | CCP-V-1 | 2.0 | | |
| 12 | CCH-34 | 5.0 | | |
| 13 | C-BHHO-5-04FF | 3.0 | | |
| Σ | | 100.0 | | |

The liquid-crystal medium has excellent applicational properties, as is evident, for example, in comparison with the following comparative example (CM-1).

Comparative Example CM-1

The mixture shown in the following table, which comprises no compound according to the invention, is prepared and investigated.

| Composition | | | | |
|---|---|---|---|---|
| Compound # | Abbreviation | Conc./% by wt. | Physical properties | |
| 1 | PCH-304FF | 12.0 | T(N, I) = | 96° C. |
| 2 | PCH-502FF | 10.0 | Δn (20° C., 589 nm) = | 0.126 |
| 3 | BCH-202FF | 12.0 | Δε (20° C., 1 kHz) > | −3.1 |
| 4 | BCH-302FF | 13.0 | $k_1$ (20° C.) = | 15.0 pN |
| 5 | PYP-2-3 | 8.0 | $k_1/k_3$ (20° C.) = | 1.09 |
| 6 | PYP-2-4 | 8.0 | $γ_1$ (20° C.) = | 169 mPa·s |
| 7 | CC-4-V | 13.0 | $t_{store}$ (−20° C.) > | 1,000 h |
| 8 | CC-3-V1 | 9.0 | $V_0$ (20° C.) = | 2.42 V |
| 9 | CCP-V-1 | 10.0 | | |
| 10 | CCPC-33 | 3.0 | | |
| 11 | CCPC-34 | 3.0 | | |
| Σ | | 100.0 | | |

The liquid-crystal medium has similar values for the clearing point, the birefringence and the dielectric anisotropy to the medium of Example 4. However, it has significantly higher rotational viscosity and at the same time a higher threshold voltage and consequently has clearly inferior applicational properties.

Example M-5

The mixture shown in the following table is prepared and investigated.

| Composition | | | | |
|---|---|---|---|---|
| Compound # | Abbreviation | Conc./% by wt. | Physical properties | |
| 1 | PCH-304FF | 5.0 | T(N, I) = | 95.5° C. |
| 2 | PCH-502FF | 3.0 | Δn (20° C., 589 nm) = | 0.129 |
| 3 | CCP-303FF | 10.0 | Δε (20° C., 1 kHz) > | −3.8 |
| 4 | BCH-202FF | 11.0 | $k_1$ (20° C.) = | 15.7 pN |
| 5 | BCH-302FF | 11.0 | $k_1/k_3$ (20° C.) = | 0.97 |
| 6 | PYP-2-3 | 6.0 | $γ_1$ (20° C.) = | 173 mPa·s |
| 7 | PYP-2-4 | 14.0 | $t_{store}$ (−20° C.) > | 1,000 h |
| 8 | CC-4-V | 15.0 | $V_0$ (20° C.) = | 2.10 V |
| 9 | CC-3-V1 | 12.0 | | |
| 10 | CCH-34 | 6.0 | | |
| 11 | C-BHHO-5-04FF | 7.0 | | |
| Σ | | 100.0 | | |

The liquid-crystal medium has excellent applicational properties, as is evident, for example, in comparison with the following comparative example (CM-2).

Comparative Example CM-2

The mixture shown in the following table, which comprises no compound according to the invention, is prepared and investigated.

| Composition | | | | |
|---|---|---|---|---|
| Compound # | Abbreviation | Conc./% by wt. | Physical properties | |
| 1 | PCH-304FF | 9.0 | T(N, I) = | 96° C. |
| 2 | PCH-502FF | 5.0 | Δn (20° C., 589 nm) = | 0.1127 |
| 3 | CCP-302FF | 8.0 | Δε (20° C., 1 kHz) > | −3.7 |
| 4 | CCP-402FF | 9.0 | $k_1$ (20° C.) = | 16.3 pN |
| 5 | BCH-2-02FF | 12.0 | $k_1/k_3$ (20° C.) = | 0.97 |
| 6 | BCH-3-02FF | 12.0 | $γ_1$ (20° C.) = | 179 mPa·s |
| 7 | PYP-2-3 | 9.0 | $t_{store}$ (−20° C.) = | 950 h |
| 8 | PYP-2-4 | 9.0 | $V_0$ (20° C.) = | 2.19 V |
| 9 | CC-4-V | 13.0 | | |
| 10 | CC-3-V1 | 11.0 | | |
| 11 | CCH-35 | 2.0 | | |
| Σ | | 100.0 | | |

The liquid-crystal medium has similar values for the clearing point, the birefringence and the dielectric anisotropy to the medium of Example 5. However, it has significantly higher rotational viscosity and at the same time a higher threshold voltage and consequently has less suitable applicational properties.

The invention claimed is:

1. A compound of formula I

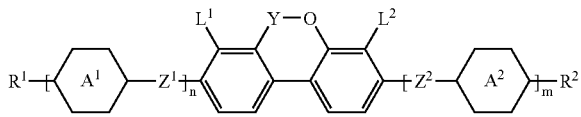

I wherein

Y is —CO—, —CS—, —CH$_2$—, —CF$_2$— or —CHF—,

L$^1$ and L$^2$ are each, independently of one another, H, F, Cl or —CN,

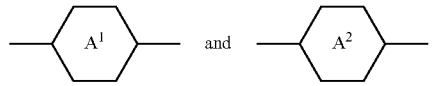

are each, independently of one another, and, if present more than once, also independently of one another, (a) a trans-1,4-cyclohexylene radical, in which, one or two non-adjacent CH$_2$ groups are optionally replaced by —O— and/or —S—, (b) a 1,4-cyclohexenylene radical, (c) a 1,4-phenylene radical, in which, one or two non-adjacent CH groups are optionally replaced by N, or (d) 1,4-bicyclo[2.2.2]octylene, 1,3-bicyclo[1.1.1]pentylene, spiro[3.3]heptane-2,4-diyl, piperidine-1,4-diyl, naphthalene-2,6-diyl, decahydronaphthalene-2,6-diyl or 1,2,3,4-tetrahydronaphthalene-2,6-diyl, R[1] and R[2] are each, independently of one another, H, halogen, —CN, —SCN, —SF$_5$, —CF$_3$, —CHF$_2$, —CH$_2$F, —OCF$_3$, —OCHF$_2$, or an alkyl group having 1 to 15 carbon atoms which is monosubstituted by CN or CF$_3$ or at least monosubstituted by halogen, and in which one or more CH$_2$ groups each, independently of one another, are optionally replaced by —O—, —S—, —CH=CH—, —CF=CF—, —CF=CH—, —CH=CF—,

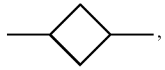

—CO—, —CO—O—, —O—CO— or —O—CO—O— in such a way that neither O nor S atoms are linked directly to one another, Z[1] and Z[2] are each, independently of one another, —CH$_2$—CH$_2$—, —CF$_2$—CF$_2$—, —CF$_2$—CH$_2$—, —CH$_2$—CF$_2$—, —CH=CH—, —CF=CF—, —CF=CH—, —CH=CF—, —C≡C—, —COO—, —OCO—, —CH$_2$O—, —OCH$_2$—, —CF$_2$O—, or —OCF$_2$—, or a combination of two of these groups, where no two O atoms are bonded to one another, and n and m are each 0, 1 or 2, where n+m is 0, 1, 2 or 3, with the proviso that, if Y is —CO—, at least one of L[1] and L[2] is not H.

2. A compound according to claim 1, which is of formula I-1a, I-1b, I-2a, I-2b, I-3a or I-3b I-1a
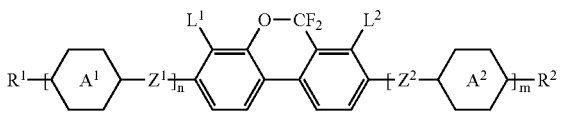

I-1b

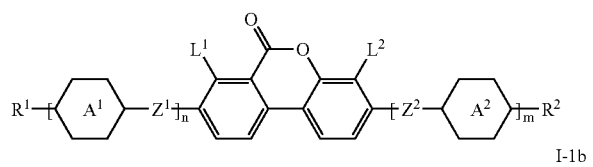

I-2a

I-2b

I-3a

-continued

I-3b
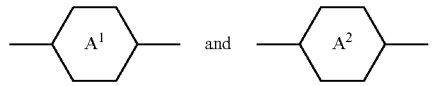

wherein

L[1] and L[2] are each, independently of one another, H, F, Cl or —CN,

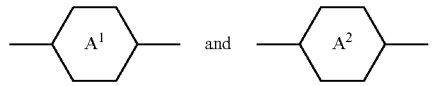

are each, independently of one another, and, if present more than once, also independently of one another, (a) a trans-1,4-cyclohexylene radical, in which, one or two non-adjacent CH$_2$ groups are optionally replaced by —O— and/or —S—, (b) a 1,4-cyclohexenylene radical, (c) a 1,4-phenylene radical, in which, one or two non-adjacent CH groups are optionally replaced by N, or (d) 1,4-bicyclo[2.2.2]octylene, 1,3-bicyclo[1.1.1]pentylene, spiro[3.3]heptane-2,4-diyl, piperidine-1,4-diyl, naphthalene-2,6-diyl, decahydronaphthalene-2,6-diyl or 1,2,3,4-tetrahydronaphthalene-2,6-diyl, R[1] and R[2] are each, independently of one another, H, halogen, —CN, —SCN, —SF$_5$, —CF$_3$, —CHF$_2$, —CH$_2$F, —OCF$_3$, —OCHF$_2$, or an alkyl group having 1 to 15 carbon atoms which is monosubstituted by CN or CF$_3$ or at least monosubstituted by halogen, and in which one or more CH$_2$ groups each, independently of one another, are optionally replaced by —O—, —S—, —CH=CH—, —CF=CF—, —CF=CH—, —CH=CF—,

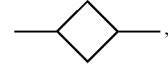

—CO—, —CO—O—, —O—CO— or —O—CO—O— in such a way that neither O nor S atoms are linked directly to one another, Z[1] and Z[2] are each, independently of one another, —CH$_2$—CH$_2$—, —CF$_2$—CF$_2$—, —CF$_2$—CH$_2$—, —CH$_2$—CF$_2$—, —CH=CH—, —CF=CF—, —CF=CH—, —CH=CF—, —C≡C—, —COO—, —OCO—, —CH$_2$O—, —OCH$_2$—, —CF$_2$O—, or —OCF$_2$—, or a combination of two of these groups, where no two O atoms are bonded to one another, and n and m are each 0, 1 or 2, where n+m is 0, 1, 2 or 3.

3. A compound according to claim 1, wherein Y is —CF$_2$—.

4. A compound according to claim 1, wherein L[1] and L[2] are both F.

5. A compound according to claim 1, wherein Z[1] and Z[2] are both a single bond.

6. A liquid-crystal medium, comprising one or more compounds of claim 1.

7. A liquid-crystal medium according to claim 6, comprising one or more dielectrically negative compound(s) of formula II

II wherein $R^{21}$ and $R^{22}$ are each, independently of one another, H, halogen, —CN, —SCN, —SF$_5$, —CF$_3$, —CHF$_2$, —CH$_2$F, —OCF$_3$, —OCHF$_2$, or an alkyl group having 1 to 15 carbon atoms which is monosubstituted by CN or CF$_3$ or at least monosubstituted by halogen, and in which one or more CH$_2$ groups each, independently of one another, are optionally replaced by —O—, —S—, —CH=CH—, —CF=CF—, —CF=CH—, —CH=CF—,

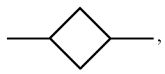

—CO—, —CO—O—, —O—CO— or —O—CO—O— in such a way that neither O nor S atoms are linked directly to one another, $Z^{21}$ and $Z^{22}$ are each, independently of one another, —CH$_2$—CH$_2$—, —CF$_2$—CF$_2$—, —CF$_2$—CH$_2$—, —CH$_2$—CF$_2$—, —CH=CH—, —CF=CF—, —CF=CH—, —CH=CF—, —C≡C—, —COO—, —OCO—, —CH$_2$O—, —OCH$_2$—, —CF$_2$O—, or —COF$_2$—, or a combination of two of these groups, where no two O atoms are bonded to one another,

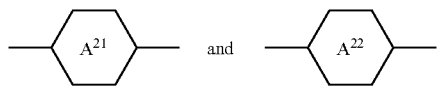

are each, independently of one another,

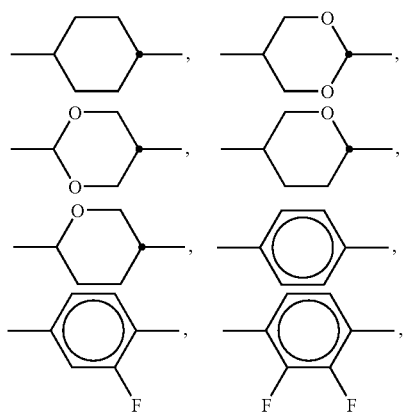

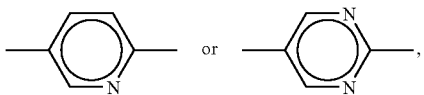

$L^1$ and $L^2$ are both C—F or one of the two is N and the other is C—F, and

I is 0 or 1.

8. A liquid-crystal medium according to claim 6, comprising one or more compound(s) of formula II-1

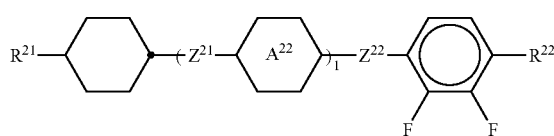

II-1 wherein $R^{21}$ and $R^{22}$ are each, independently of one another, H, halogen, —CN, —SCN, —SF$_5$, —CF$_3$, —CHF$_2$, —CH$_2$F, —OCF$_3$, —OCHF$_2$, or an alkyl group having 1 to 15 carbon atoms which is monosubstituted by CN or CF$_3$ or at least monosubstituted by halogen, and in which one or more CH$_2$ groups each, independently of one another, are optionally replaced by —O—, —S—, —CH=CH—, —CF=CF—, —CF=CH—, —CH=CF—,

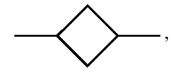

—CO—, —CO—O—, —O—CO— or —O—CO—O— in such a way that neither O nor S atoms are linked directly to one another, $Z^{21}$ and $Z^{22}$ are each, independently of one another, —CH$_2$—CH$_2$—, —CF$_2$—CF$_2$—, —CF$_2$—CH$_2$—, —CH$_2$—CF$_2$—, —CH=CH—, —CF=CF—, —CF=CH—, —CH=CF—, —C≡C—, —COO—, —OCO—, —CH$_2$O—, —OCH$_2$—, —CF$_2$O—, or —OCF$_2$—, or a combination of two of these groups, where no two O atoms are bonded to one another,

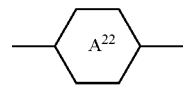

is

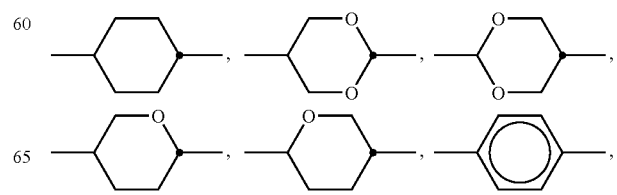

-continued

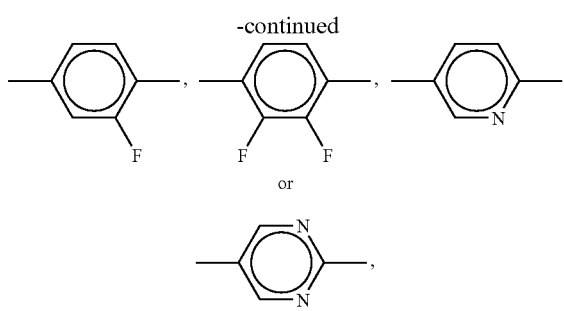

and l is 0 or 1.

9. An electro-optical display containing a liquid-crystal medium according to claim 6.

10. A display according to claim 9, which is a VAN LCD.

11. A compound according to claim 2, wherein $L^1$ and $L^2$ are both F.

12. A compound according to claim 2, wherein $Z^1$ and $Z^2$ are both a single bond.

13. A liquid-crystal medium, comprising one or more compounds of claim 2.

14. An electro-optical display containing a liquid-crystal medium according to claim 7.

15. A display according to claim 14, which is a VAN LCD.

16. An electro-optical display containing a liquid-crystal medium according to claim 8.

17. A display according to claim 6, which is a VAN LCD.

18. An electro-optical display containing a liquid-crystal medium according to claim 13.

19. A display according to claim 18, which is a VAN LCD.

20. A liquid-crystal medium, comprising one or more compounds of claim 1, wherein $L^1$ and $L^2$ are both F and $Z^1$ and $Z^2$ are both a single bond.

* * * * *

UNITED STATES PATENT AND TRADEMARK OFFICE
CERTIFICATE OF CORRECTION

PATENT NO. : 7,326,447 B2 Page 1 of 1
APPLICATION NO. : 10/546801
DATED : February 5, 2008
INVENTOR(S) : Andreas Taugerbeck It is certified that error appears in the above-identified patent and that said Letters Patent is hereby corrected as shown below:

Column 143, line 40 claim 7 reads "–COF$_2$-", should read -- –OCF$_2$- --

Signed and Sealed this

Eighth Day of July, 2008

JON W. DUDAS
*Director of the United States Patent and Trademark Office*